US008562973B2

(12) United States Patent
Edinger et al.

(10) Patent No.: US 8,562,973 B2
(45) Date of Patent: Oct. 22, 2013

(54) TREATMENT OF SARCOIDOSIS USING PLACENTAL STEM CELLS

(75) Inventors: James W. Edinger, Belford, NJ (US);
Steven Alan Fischkoff, Short Hills, NJ (US); Aleksandar Francki, Annandale, NJ (US); Vladimir Jankovic, New York, NY (US); Bitao Liang, Closter, NJ (US); Philippe Martin, Hoboken, NJ (US); Cynthia Ray, Branchburg, NJ (US); Xiaokui Zhang, Livingston, NJ (US)

(73) Assignee: Anthrogenesis Corporation, Warren, NJ (US)

(*) Notice: Subject to any disclaimer, the term of this patent is extended or adjusted under 35 U.S.C. 154(b) by 175 days.

(21) Appl. No.: 13/081,422

(22) Filed: Apr. 6, 2011

(65) Prior Publication Data

US 2011/0311491 A1    Dec. 22, 2011

Related U.S. Application Data

(60) Provisional application No. 61/322,272, filed on Apr. 8, 2010.

(51) Int. Cl.
C12C 7/04    (2006.01)

(52) U.S. Cl.
USPC ............................. 424/93.7; 424/583

(58) Field of Classification Search
USPC ................................. 424/93.7, 583
See application file for complete search history.

(56) References Cited

U.S. PATENT DOCUMENTS

| | | |
|---|---|---|
| 3,862,002 A | 1/1975 | Sanders |
| 4,798,824 A | 1/1989 | Belzer et al. |
| 4,829,000 A | 5/1989 | Kleinman et al. |
| 5,004,681 A | 4/1991 | Boyse et al. |
| 5,192,553 A | 3/1993 | Boyse et al. |
| 5,197,985 A | 3/1993 | Caplan et al. |
| 5,226,914 A | 7/1993 | Caplan et al. |
| 5,272,071 A | 12/1993 | Chappel |
| 5,284,766 A | 2/1994 | Okano et al. |
| 5,372,581 A | 12/1994 | Anderson |
| 5,415,665 A | 5/1995 | Hessel et al. |
| 5,426,098 A | 6/1995 | Carlino |
| 5,437,994 A | 8/1995 | Emerson et al. |
| 5,443,950 A | 8/1995 | Naughton et al. |
| 5,460,964 A | 10/1995 | McGlave et al. |
| 5,464,764 A | 11/1995 | Capecchi et al. |
| 5,486,359 A | 1/1996 | Caplan et al. |
| 5,487,992 A | 1/1996 | Capecchi et al. |
| 5,516,532 A | 5/1996 | Atala et al. |
| 5,552,267 A | 9/1996 | Stern et al. |
| 5,580,777 A | 12/1996 | Bernard |
| 5,591,625 A | 1/1997 | Gerson et al. |
| 5,605,822 A | 2/1997 | Emerson et al. |
| 5,613,982 A | 3/1997 | Goldstein |
| 5,627,059 A | 5/1997 | Capecchi et al. |
| 5,635,386 A | 6/1997 | Palsson et al. |
| 5,635,387 A | 6/1997 | Fei et al. |
| 5,643,741 A | 7/1997 | Tsukamoto et al. |
| 5,646,043 A | 7/1997 | Emerson et al. |
| 5,654,186 A | 8/1997 | Cerami et al. |
| 5,654,381 A | 8/1997 | Hrkach et al. |
| 5,665,557 A | 9/1997 | Murray et al. |
| 5,668,104 A | 9/1997 | Nakahata et al. |
| 5,670,147 A | 9/1997 | Emerson et al. |
| 5,670,351 A | 9/1997 | Emerson et al. |
| 5,672,346 A | 9/1997 | Srour et al. |
| 5,677,139 A | 10/1997 | Johnson |
| 5,709,854 A | 1/1998 | Griffith-Cima et al. |
| 5,716,616 A | 2/1998 | Prockop et al. |
| 5,716,794 A | 2/1998 | Tjota et al. |
| 5,716,827 A | 2/1998 | Tsukamoto |
| 5,733,541 A | 3/1998 | Taichman et al. |
| 5,733,542 A | 3/1998 | Haynesworth et al. |
| 5,736,396 A | 4/1998 | Bruder et al. |
| 5,744,361 A | 4/1998 | Hoffman et al. |
| 5,750,397 A | 5/1998 | Tsukamoto et al. |
| 5,763,197 A | 6/1998 | Tsukamoto et al. |
| 5,763,266 A | 6/1998 | Palsson et al. |
| 5,800,539 A | 9/1998 | Waller |
| 5,806,529 A | 9/1998 | Reisner et al. |
| 5,807,686 A | 9/1998 | Wagner et al. |

(Continued)

FOREIGN PATENT DOCUMENTS

| | | |
|---|---|---|
| CN | 1407088 | 4/2003 |
| CN | 1548529 | 5/2003 |

(Continued)

OTHER PUBLICATIONS

Gould, Karen et al. Dermatologic Manifestations of Sarcoidosis. Medscape Reference: Drugs, Diseases, and Procedures. Downloaded from the Medscape websites on Nov. 27, 2012: <http://emedicine.medscape.com/article/1123970-overview#aw2aab6b8>.*

Mayo Clinic. Hypothyroidism. Downloaded from the Mayo Clinic website on Mar. 20, 2013: <http://www.mayoclinic.com/health/hypothyroidism/DS00353>.*

Agency for Toxic Substances and Disease Registry (ATSDR). What Is Cancer?. Downloaded from the ATSDR website on Mar. 20, 2013: <http://www.atsdr.cdc.gov/com/cancer.pdf>.*

Blaney, Greg. Vitamin D Metabolites as Clinical Markers in Autoimmune and Chronic Disease. Contemporary Challenges in Autoimmunity. Pages 384-390.*

American Society for Reproductive Medicine. Patient Fact Sheet: Hyperprolactemia. Downloaded from the ASRM website on Mar. 20, 2013: <http://www.reproductivefacts.org/uploadedFiles/ASRM_Content/Resources/Patient_Resources/Fact_Sheets_and_Info_Booklets/Prolactin_Excess.pdf>.*

(Continued)

Primary Examiner — Susan Hanley
Assistant Examiner — Nghi Nguyen
(74) Attorney, Agent, or Firm — Jones Day

(57) ABSTRACT

Methods of treating individuals having sarcoidosis or a sarcoidosis-related disease or disorder using placental cells are described. Also describe are kits comprising placental stem cells or a composition thereof that can be used in methods of treating sarcoidosis or a sarcoidosis-related disease or disorder.

23 Claims, No Drawings

(56) References Cited

U.S. PATENT DOCUMENTS

| | | |
|---|---|---|
| 5,811,094 A | 9/1998 | Caplan et al. |
| 5,827,735 A | 10/1998 | Young et al. |
| 5,827,740 A | 10/1998 | Pittenger |
| 5,827,742 A | 10/1998 | Scadden |
| 5,837,539 A | 11/1998 | Caplan et al. |
| 5,849,553 A | 12/1998 | Anderson et al. |
| 5,851,984 A | 12/1998 | Matthews et al. |
| 5,855,619 A | 1/1999 | Caplan et al. |
| 5,858,782 A | 1/1999 | Long et al. |
| 5,866,414 A | 2/1999 | Badylak et al. |
| 5,874,301 A | 2/1999 | Keller et al. |
| 5,877,299 A | 3/1999 | Thomas et al. |
| 5,879,318 A | 3/1999 | Van Der Heiden et al. |
| 5,879,940 A | 3/1999 | Torok-Storb et al. |
| 5,902,741 A | 5/1999 | Purchio et al. |
| 5,905,041 A | 5/1999 | Beug et al. |
| 5,906,934 A | 5/1999 | Grande et al. |
| 5,908,782 A | 6/1999 | Marshak et al. |
| 5,908,784 A | 6/1999 | Johnstone et al. |
| 5,914,108 A | 6/1999 | Tsukamoto et al. |
| 5,914,268 A | 6/1999 | Keller et al. |
| 5,916,202 A | 6/1999 | Haswell |
| 5,919,176 A | 7/1999 | Kuypers et al. |
| 5,919,702 A | 7/1999 | Purchio et al. |
| 5,922,597 A | 7/1999 | Verfaillie et al. |
| 5,925,567 A | 7/1999 | Kraus et al. |
| 5,928,214 A | 7/1999 | Rubinstein et al. |
| 5,928,947 A | 7/1999 | Anderson et al. |
| 5,942,225 A | 8/1999 | Bruder et al. |
| 5,942,496 A | 8/1999 | Bonadio et al. |
| 5,958,767 A | 9/1999 | Snyder et al. |
| 5,962,325 A | 10/1999 | Naughton et al. |
| 5,968,829 A | 10/1999 | Carpenter |
| 5,969,105 A | 10/1999 | Feng et al. |
| 5,993,429 A | 11/1999 | Kuypers et al. |
| 5,997,860 A | 12/1999 | Bauer et al. |
| 6,001,654 A | 12/1999 | Anderson et al. |
| 6,010,696 A | 1/2000 | Caplan et al. |
| 6,011,000 A | 1/2000 | Faller et al. |
| 6,020,469 A | 2/2000 | Hershenson |
| 6,022,540 A | 2/2000 | Bruder et al. |
| 6,022,743 A | 2/2000 | Naughton et al. |
| 6,022,848 A | 2/2000 | Kozlov et al. |
| 6,030,836 A | 2/2000 | Thiede |
| 6,057,123 A | 5/2000 | Craig et al. |
| 6,059,968 A | 5/2000 | Wolf, Jr. |
| 6,077,708 A | 6/2000 | Collins et al. |
| 6,087,113 A | 7/2000 | Caplan et al. |
| 6,093,531 A | 7/2000 | Bjornson et al. |
| 6,110,739 A | 8/2000 | Keller et al. |
| 6,127,135 A | 10/2000 | Hill et al. |
| 6,146,888 A | 11/2000 | Smith et al. |
| 6,174,333 B1 | 1/2001 | Kadiyala et al. |
| 6,179,819 B1 | 1/2001 | Haswel |
| 6,184,035 B1 | 2/2001 | Csete et al. |
| 6,190,368 B1 | 2/2001 | Kuypers et al. |
| 6,214,369 B1 | 4/2001 | Grande et al. |
| 6,224,860 B1 | 5/2001 | Brown |
| 6,225,119 B1 | 5/2001 | Qasba et al. |
| 6,227,202 B1 | 5/2001 | Mataparkar |
| 6,231,880 B1 | 5/2001 | Perrine |
| 6,239,157 B1 | 5/2001 | Mbalaviele et al. |
| 6,248,587 B1 | 6/2001 | Rodgers et al. |
| 6,251,383 B1 | 6/2001 | Upadhyay et al. |
| 6,255,112 B1 | 7/2001 | Thiede et al. |
| 6,261,549 B1 | 7/2001 | Fernandez et al. |
| 6,280,718 B1 | 8/2001 | Kaufman et al. |
| 6,281,012 B1 | 8/2001 | McIntosh et al. |
| 6,291,240 B1 | 9/2001 | Mansbridge |
| 6,300,314 B1 | 10/2001 | Wallner et al. |
| 6,306,575 B1 | 10/2001 | Thomas et al. |
| 6,312,950 B1 | 11/2001 | Ohmura et al. |
| 6,322,784 B1 | 11/2001 | Pittenger et al. |
| 6,326,019 B1 | 12/2001 | Tseng |
| 6,326,198 B1 | 12/2001 | Emerson et al. |
| 6,328,765 B1 | 12/2001 | Hardwick et al. |
| 6,328,960 B1 | 12/2001 | McIntosh et al. |
| 6,333,029 B1 | 12/2001 | Vyakamam et al. |
| 6,335,195 B1 | 1/2002 | Rodgers et al. |
| 6,337,387 B1 | 1/2002 | Sakano et al. |
| 6,338,942 B2 | 1/2002 | Kraus et al. |
| 6,355,239 B1 | 3/2002 | Bruder et al. |
| 6,355,699 B1 | 3/2002 | Vyakarnam et al. |
| 6,368,636 B1 | 4/2002 | McIntosh et al. |
| 6,379,953 B1 | 4/2002 | Bruder et al. |
| 6,384,105 B1 | 5/2002 | He |
| 6,387,367 B1 | 5/2002 | Davis-Sproul et al. |
| 6,387,369 B1 | 5/2002 | Pittenger et al. |
| 6,461,645 B1 | 10/2002 | Boyse et al. |
| 6,497,875 B1 | 12/2002 | Sorrell et al. |
| 6,528,245 B2 | 3/2003 | Sanchez-Ramos et al. |
| 6,534,084 B1 | 3/2003 | Vyakamam et al. |
| 6,541,024 B1 | 4/2003 | Kadiyala et al. |
| 6,548,299 B1 | 4/2003 | Pykett |
| 6,645,731 B2 | 11/2003 | Terstappen et al. |
| 6,685,936 B2 | 2/2004 | McIntosh et al. |
| 6,709,864 B1 | 3/2004 | Pittenger et al. |
| 6,753,181 B2 | 6/2004 | Atala et al. |
| 6,797,269 B2 | 9/2004 | Mosca et al. |
| 6,835,377 B2 | 12/2004 | Goldberg et al. |
| 6,863,900 B2 | 3/2005 | Kadiyala et al. |
| 6,875,430 B2 | 4/2005 | McIntosh et al. |
| 6,875,607 B1 | 4/2005 | Reubinoff et al. |
| 6,916,655 B2 | 7/2005 | Yasumoto |
| 7,029,666 B2 | 4/2006 | Bruder et al. |
| 7,045,148 B2 | 5/2006 | Hariri |
| 7,091,353 B2 | 8/2006 | Robarge et al. |
| 7,147,626 B2 | 12/2006 | Goodman et al. |
| 7,153,500 B2 | 12/2006 | Qasba et al. |
| 7,244,759 B2 | 7/2007 | Muller et al. |
| 7,255,879 B2 | 8/2007 | Hariri |
| 7,311,904 B2 | 12/2007 | Hariri |
| 7,311,905 B2 | 12/2007 | Hariri |
| 7,468,276 B2 | 12/2008 | Hariri |
| 7,498,171 B2 | 3/2009 | Hariri et al. |
| 7,638,141 B2 | 12/2009 | Hariri |
| 7,642,091 B2 | 1/2010 | Lee et al. |
| 7,682,803 B2 | 3/2010 | Paludan et al. |
| 7,700,090 B2 | 4/2010 | Heidaran et al. |
| 7,909,806 B2 | 3/2011 | Goodman |
| 7,914,779 B2 | 3/2011 | Hariri |
| 7,928,280 B2 | 4/2011 | Hariri et al. |
| 7,976,836 B2 | 7/2011 | Hariri |
| 7,993,918 B2 | 8/2011 | Paludan et al. |
| 8,057,788 B2 | 11/2011 | Hariri |
| 8,057,789 B2 | 11/2011 | Hariri |
| 8,071,135 B2 | 12/2011 | Liu et al. |
| 8,071,376 B2 | 12/2011 | Heidaran |
| 8,105,634 B2 | 1/2012 | Liu et al. |
| 8,202,703 B2 | 6/2012 | Edinger et al. |
| 8,263,065 B2 | 9/2012 | Hariri et al. |
| 2001/0005591 A1 | 6/2001 | Qasba et al. |
| 2001/0038836 A1 | 11/2001 | During et al. |
| 2001/0044124 A1 | 11/2001 | Bacus |
| 2002/0028510 A1 | 3/2002 | Sanberg et al. |
| 2002/0059106 A1 | 5/2002 | Tani |
| 2002/0061300 A1 | 5/2002 | Gokcen |
| 2002/0086005 A1 | 7/2002 | Chiu et al. |
| 2002/0102239 A1 | 8/2002 | Koopmans |
| 2002/0110544 A1 | 8/2002 | Goldberg et al. |
| 2002/0123141 A1 | 9/2002 | Hariri |
| 2002/0132343 A1 | 9/2002 | Lum |
| 2002/0160510 A1 | 10/2002 | Hariri |
| 2003/0007954 A1 | 1/2003 | Naughton et al. |
| 2003/0032179 A1 | 2/2003 | Hariri |
| 2003/0044976 A1 | 3/2003 | Dominko et al. |
| 2003/0044977 A1 | 3/2003 | Sakuragawa et al. |
| 2003/0045552 A1 | 3/2003 | Robarge et al. |
| 2003/0059414 A1 | 3/2003 | Ho et al. |
| 2003/0068306 A1 | 4/2003 | Dilber |
| 2003/0096841 A1 | 5/2003 | Robarge et al. |
| 2003/0152558 A1 | 8/2003 | Luft |
| 2003/0161818 A1 | 8/2003 | Weiss et al. |
| 2003/0180269 A1 | 9/2003 | Hariri |

(56) References Cited

U.S. PATENT DOCUMENTS

| | | |
|---|---|---|
| 2003/0187515 A1 | 10/2003 | Hariri |
| 2003/0235090 A1 | 12/2003 | Lee |
| 2003/0235563 A1 | 12/2003 | Strom et al. |
| 2003/0235909 A1 | 12/2003 | Hariri |
| 2004/0018617 A1 | 1/2004 | Hwang |
| 2004/0028660 A1 | 2/2004 | Hariri et al. |
| 2004/0048372 A1 | 3/2004 | Hariri |
| 2004/0048796 A1 | 3/2004 | Hariri et al. |
| 2004/0107453 A1 | 6/2004 | Furcht et al. |
| 2004/0136967 A1 | 7/2004 | Weiss et al. |
| 2004/0161419 A1 | 8/2004 | Strom et al. |
| 2004/0166097 A1 | 8/2004 | Prockop |
| 2004/0171147 A1 | 9/2004 | Hariri |
| 2004/0176434 A1 | 9/2004 | Bennett et al. |
| 2004/0180040 A1 | 9/2004 | Phillips et al. |
| 2004/0219136 A1 | 11/2004 | Hariri |
| 2004/0229351 A1 | 11/2004 | Rodriguez |
| 2004/0241144 A1 | 12/2004 | Kaps et al. |
| 2005/0019865 A1 | 1/2005 | Kihm et al. |
| 2005/0019908 A1 | 1/2005 | Hariri |
| 2005/0032209 A1 | 2/2005 | Messina et al. |
| 2005/0037491 A1 | 2/2005 | Mistry et al. |
| 2005/0042595 A1 | 2/2005 | Haas |
| 2005/0054093 A1 | 3/2005 | Haas |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0058641 A1 | 3/2005 | Siemionow |
| 2005/0074435 A1 | 4/2005 | Casper |
| 2005/0085543 A1 | 4/2005 | Wallimann et al. |
| 2005/0089513 A1 | 4/2005 | Sakuragawa et al. |
| 2005/0112104 A1 | 5/2005 | Pittenger et al. |
| 2005/0118147 A1 | 6/2005 | Oh |
| 2005/0118712 A1 | 6/2005 | Tsai et al. |
| 2005/0118715 A1 | 6/2005 | Hariri et al. |
| 2005/0124003 A1 | 6/2005 | Atala et al. |
| 2005/0142118 A1 | 6/2005 | Wernet |
| 2005/0143420 A1 | 6/2005 | Moutouh-de Parseval et al. |
| 2005/0148034 A1 | 7/2005 | Hariri et al. |
| 2005/0148074 A1 | 7/2005 | Davies et al. |
| 2005/0176139 A1 | 8/2005 | Chen et al. |
| 2005/0181502 A1 | 8/2005 | Furcht et al. |
| 2005/0186182 A1 | 8/2005 | Deisher et al. |
| 2005/0233452 A1 | 10/2005 | Ho et al. |
| 2005/0239897 A1 | 10/2005 | Pittenger et al. |
| 2005/0266391 A1 | 12/2005 | Bennett et al. |
| 2005/0272148 A1 | 12/2005 | Hariri |
| 2005/0276792 A1 | 12/2005 | Kaminski et al. |
| 2005/0282272 A1 | 12/2005 | Bhatia et al. |
| 2005/0283844 A1 | 12/2005 | Furcht et al. |
| 2006/0004043 A1 | 1/2006 | Bhagwat et al. |
| 2006/0008450 A1 | 1/2006 | Verfaillie et al. |
| 2006/0024280 A1 | 2/2006 | West |
| 2006/0060494 A1 | 3/2006 | Goodman et al. |
| 2006/0078993 A1 | 4/2006 | Phan et al. |
| 2006/0122179 A1 | 6/2006 | Zeldis et al. |
| 2006/0128012 A1 | 6/2006 | Arinzeh et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0205771 A1 | 9/2006 | Noble et al. |
| 2006/0222634 A1 | 10/2006 | Clarke et al. |
| 2006/0223177 A1 | 10/2006 | Harris et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2006/0263337 A1 | 11/2006 | Maziarz et al. |
| 2006/0281178 A1 | 12/2006 | Sakuragawa et al. |
| 2007/0009494 A1 | 1/2007 | Mistry et al. |
| 2007/0014771 A1 | 1/2007 | Mistry et al. |
| 2007/0020225 A1 | 1/2007 | Abramson et al. |
| 2007/0021704 A1 | 1/2007 | Hariri et al. |
| 2007/0021762 A1 | 1/2007 | Liu et al. |
| 2007/0031384 A1 | 2/2007 | Atala et al. |
| 2007/0036767 A1 | 2/2007 | Mistry et al. |
| 2007/0038298 A1 | 2/2007 | Sulner et al. |
| 2007/0041954 A1 | 2/2007 | Ichim |
| 2007/0043328 A1 | 2/2007 | Goodman et al. |
| 2007/0053888 A1 | 3/2007 | Hariri |
| 2007/0077652 A1 | 4/2007 | Peled et al. |
| 2007/0092497 A1 | 4/2007 | Hariri |
| 2007/0092967 A1 | 4/2007 | Han et al. |
| 2007/0116682 A1 | 5/2007 | Atala et al. |
| 2007/0122903 A1 | 5/2007 | Rezania et al. |
| 2007/0134210 A1 | 6/2007 | Heidaran |
| 2007/0141700 A1 | 6/2007 | Harmon |
| 2007/0160588 A1 | 7/2007 | Kihm |
| 2007/0190034 A1 | 8/2007 | Paludan et al. |
| 2007/0190042 A1 | 8/2007 | Edinger et al. |
| 2007/0190649 A1 | 8/2007 | Gage |
| 2007/0224174 A1 | 9/2007 | Kang |
| 2007/0253931 A1 | 11/2007 | Varney et al. |
| 2007/0258963 A1 | 11/2007 | Danilkovitch et al. |
| 2007/0264269 A1 | 11/2007 | Harmon et al. |
| 2007/0275362 A1 | 11/2007 | Edinger et al. |
| 2007/0287176 A1 | 12/2007 | Rezania |
| 2007/0292399 A1 | 12/2007 | Heidaran et al. |
| 2007/0292910 A1 | 12/2007 | Heidaran et al. |
| 2008/0032401 A1 | 2/2008 | Edinger et al. |
| 2008/0044392 A1 | 2/2008 | Kues et al. |
| 2008/0044848 A1 | 2/2008 | Heidaran |
| 2008/0050347 A1 | 2/2008 | Ichim |
| 2008/0050814 A1 | 2/2008 | Allickson |
| 2008/0064098 A1 | 3/2008 | Allickson |
| 2008/0069895 A1 | 3/2008 | Liu et al. |
| 2008/0095749 A1 | 4/2008 | Aggarwal et al. |
| 2008/0131410 A1 | 6/2008 | Hariri |
| 2008/0131522 A1 | 6/2008 | Liu et al. |
| 2008/0131966 A1 | 6/2008 | Hariri |
| 2008/0145934 A1 | 6/2008 | Harris et al. |
| 2008/0152624 A1 | 6/2008 | Paludan et al. |
| 2008/0152629 A1 | 6/2008 | Edinger et al. |
| 2008/0159998 A1 | 7/2008 | Ichim |
| 2008/0166328 A1 | 7/2008 | Harmon et al. |
| 2008/0175824 A1 | 7/2008 | Heidaran et al. |
| 2008/0181935 A1 | 7/2008 | Bhatia et al. |
| 2008/0181967 A1 | 7/2008 | Liu et al. |
| 2008/0206343 A1 | 8/2008 | Edinger et al. |
| 2008/0208158 A1 | 8/2008 | Goodman et al. |
| 2008/0213227 A1 | 9/2008 | Aggarwal et al. |
| 2008/0213228 A1 | 9/2008 | Edinger et al. |
| 2008/0226595 A1 | 9/2008 | Edinger et al. |
| 2008/0226612 A1 | 9/2008 | Treves et al. |
| 2008/0248005 A1 | 10/2008 | Phan |
| 2008/0254005 A1 | 10/2008 | Riordan et al. |
| 2008/0254538 A1 | 10/2008 | Messina et al. |
| 2008/0260694 A1 | 10/2008 | Gronthos et al. |
| 2008/0260703 A1 | 10/2008 | Riordan et al. |
| 2008/0260704 A1 | 10/2008 | Riordan et al. |
| 2008/0274087 A1 | 11/2008 | Li et al. |
| 2008/0279956 A1 | 11/2008 | Lin |
| 2008/0286249 A1 | 11/2008 | Varney et al. |
| 2008/0286267 A1 | 11/2008 | Sing et al. |
| 2008/0292597 A1 | 11/2008 | Steenblock |
| 2008/0299090 A1 | 12/2008 | Weiss et al. |
| 2008/0305148 A1 | 12/2008 | Fu |
| 2008/0311087 A1 | 12/2008 | Gosiewska et al. |
| 2009/0004738 A1 | 1/2009 | Merchav et al. |
| 2009/0016999 A1 | 1/2009 | Cohen et al. |
| 2009/0053182 A1 | 2/2009 | Ichim et al. |
| 2009/0053805 A1 | 2/2009 | Hariri |
| 2009/0074728 A1 | 3/2009 | Gronthos et al. |
| 2009/0074731 A1 | 3/2009 | Librach et al. |
| 2009/0075381 A1 | 3/2009 | Clarke et al. |
| 2009/0081171 A1 | 3/2009 | Fu et al. |
| 2009/0092653 A1 | 4/2009 | Colter et al. |
| 2009/0104158 A1 | 4/2009 | Young et al. |
| 2009/0104163 A1 | 4/2009 | Deans et al. |

(56) References Cited

U.S. PATENT DOCUMENTS

| | | |
|---|---|---|
| 2009/0104164 A1 | 4/2009 | Zhang et al. |
| 2009/0123437 A1 | 5/2009 | Takebe |
| 2009/0124007 A1 | 5/2009 | Cho |
| 2009/0136457 A1 | 5/2009 | Sing et al. |
| 2009/0136471 A1 | 5/2009 | Heidaran et al. |
| 2009/0142831 A1 | 6/2009 | Hariri |
| 2009/0149371 A1 | 6/2009 | Mistry et al. |
| 2009/0169522 A1 | 7/2009 | Danilkovitch et al. |
| 2009/0169597 A1 | 7/2009 | Brown et al. |
| 2009/0170200 A1 | 7/2009 | Yeh et al. |
| 2009/0186006 A1 | 7/2009 | Murphy |
| 2009/0202479 A1 | 8/2009 | Shi et al. |
| 2009/0208463 A1 | 8/2009 | Pittenger et al. |
| 2009/0214484 A1 | 8/2009 | Mironov |
| 2009/0214493 A1 | 8/2009 | Pittenger et al. |
| 2009/0220464 A1 | 9/2009 | Aggarwal et al. |
| 2009/0226406 A1 | 9/2009 | Hariri |
| 2009/0232781 A1 | 9/2009 | Fu |
| 2009/0232782 A1 | 9/2009 | Fu |
| 2009/0238801 A1 | 9/2009 | Woodbury et al. |
| 2009/0252710 A1 | 10/2009 | Zhang et al. |
| 2009/0257989 A1 | 10/2009 | Vanguri et al. |
| 2009/0263361 A1 | 10/2009 | Lee et al. |
| 2009/0274665 A1 | 11/2009 | Akabutu et al. |
| 2009/0280093 A1 | 11/2009 | Friedlander |
| 2009/0285842 A1 | 11/2009 | Davies et al. |
| 2009/0291061 A1 | 11/2009 | Riordan et al. |
| 2009/0304639 A1 | 12/2009 | Yokoo et al. |
| 2009/0305406 A1 | 12/2009 | Pytlik et al. |
| 2009/0311223 A1 | 12/2009 | Ichim |
| 2009/0311782 A1 | 12/2009 | Chiou et al. |
| 2009/0324609 A1 | 12/2009 | Lodie et al. |
| 2010/0008890 A1 | 1/2010 | Mays et al. |
| 2010/0008992 A1 | 1/2010 | Ichim |
| 2010/0015705 A1 | 1/2010 | Vodyanyk et al. |
| 2010/0015712 A1 | 1/2010 | Skuragawa |
| 2010/0021434 A1 | 1/2010 | Melamed et al. |
| 2010/0028306 A1 | 2/2010 | Clarke et al. |
| 2010/0028997 A1 | 2/2010 | Lin |
| 2010/0047213 A1 | 2/2010 | Zeitlin et al. |
| 2010/0047214 A1 | 2/2010 | Abramson et al. |
| 2010/0047351 A1 | 2/2010 | Zeitlin et al. |
| 2010/0105132 A1 | 4/2010 | Totey et al. |
| 2010/0120015 A1 | 5/2010 | Hariri |
| 2010/0124569 A1 | 5/2010 | Abbot |
| 2010/0143312 A1* | 6/2010 | Hariri et al. .............. 424/93.7 |
| 2010/0172830 A1 | 7/2010 | Heidaran |
| 2010/0183571 A1 | 7/2010 | Paludan et al. |
| 2010/0260847 A1 | 10/2010 | Hariri |
| 2010/0291679 A1 | 11/2010 | Edinger et al. |
| 2010/0297689 A1 | 11/2010 | Edinger et al. |
| 2010/0311036 A1 | 12/2010 | He |
| 2010/0323446 A1 | 12/2010 | Barnett |
| 2011/0003387 A1 | 1/2011 | Abbot et al. |
| 2011/0206645 A1 | 8/2011 | Zhang et al. |
| 2011/0217271 A1 | 9/2011 | Hariri |
| 2011/0217272 A1 | 9/2011 | Hariri |
| 2011/0223141 A1 | 9/2011 | Hariri |
| 2011/0250182 A1 | 10/2011 | Abbot |
| 2011/0250185 A1 | 10/2011 | Paludan et al. |
| 2011/0280843 A1 | 11/2011 | Edinger et al. |
| 2011/0280845 A1 | 11/2011 | Edinger et al. |
| 2011/0280849 A1 | 11/2011 | Zhang et al. |
| 2011/0318401 A1 | 12/2011 | Hariri et al. |
| 2012/0020936 A1 | 1/2012 | Hariri |
| 2012/0034195 A1 | 2/2012 | Hariri |
| 2012/0058089 A1 | 3/2012 | Hariri |
| 2012/0121550 A1 | 5/2012 | Heidaran |
| 2012/0148553 A1 | 6/2012 | Hariri et al. |
| 2012/0171161 A1 | 7/2012 | Abramson et al. |
| 2012/0171180 A1 | 7/2012 | Abramson et al. |
| 2012/0171295 A1 | 7/2012 | Abramson et al. |
| 2012/0230959 A1 | 9/2012 | Abbot et al. |
| 2012/0269774 A1* | 10/2012 | Ichim et al. .............. 424/93.7 |
| 2012/0328583 A1 | 12/2012 | Herzberg et al. |

FOREIGN PATENT DOCUMENTS

| | | |
|---|---|---|
| CN | 1786154 | 6/2006 |
| EP | 0333328 | 9/1989 |
| EP | 0529751 | 3/1993 |
| EP | 0552380 | 7/1993 |
| EP | 1264877 | 12/2002 |
| EP | 1288293 | 3/2003 |
| EP | 1384775 | 1/2004 |
| EP | 1405649 | 4/2004 |
| EP | 1535994 | 6/2005 |
| EP | 1775341 | 4/2007 |
| JP | 2003235549 | 12/2002 |
| JP | 2005151907 | 11/2003 |
| WO | WO 90/11354 | 10/1990 |
| WO | WO 91/01140 | 2/1991 |
| WO | WO 91/06666 | 5/1991 |
| WO | WO 91/06667 | 5/1991 |
| WO | WO 93/04169 | 3/1993 |
| WO | WO 95/22611 | 8/1995 |
| WO | WO 96/34035 | 12/1996 |
| WO | WO 96/39101 | 12/1996 |
| WO | WO 98/37903 | 9/1998 |
| WO | WO 99/03973 | 1/1999 |
| WO | WO 99/64566 | 12/1999 |
| WO | WO 00/17325 | 3/2000 |
| WO | WO 00/27999 | 5/2000 |
| WO | WO 00/38762 | 7/2000 |
| WO | WO 00/73421 | 12/2000 |
| WO | WO 01/93909 | 12/2001 |
| WO | WO 02/46373 | 6/2002 |
| WO | WO 02/059106 | 8/2002 |
| WO | WO 02/063962 | 8/2002 |
| WO | WO 02/064083 | 8/2002 |
| WO | WO 02/064755 | 8/2002 |
| WO | WO 02/097052 | 12/2002 |
| WO | WO 03/042405 | 5/2003 |
| WO | WO 03/068937 | 8/2003 |
| WO | WO 03/086373 | 10/2003 |
| WO | WO 03/087333 | 10/2003 |
| WO | WO 03/087392 | 10/2003 |
| WO | WO 03/089619 | 10/2003 |
| WO | WO 03/102151 | 12/2003 |
| WO | WO 2004/035064 | 4/2004 |
| WO | WO 2004/047770 | 6/2004 |
| WO | WO 2004/071283 | 8/2004 |
| WO | WO 2004/087896 | 10/2004 |
| WO | WO 2005/042703 | 5/2005 |
| WO | WO 2005/097190 | 10/2005 |
| WO | WO 2005/105992 | 11/2005 |
| WO | WO 2005/055929 | 1/2006 |
| WO | WO 2006/015214 | 2/2006 |
| WO | WO 2006/111706 | 10/2006 |
| WO | WO 2006/117889 | 11/2006 |
| WO | WO 2007/024441 | 3/2007 |
| WO | WO 2007/047465 | 4/2007 |
| WO | WO 2007/047468 | 4/2007 |
| WO | WO 2007/056578 | 5/2007 |
| WO | WO 2007/071048 | 6/2007 |
| WO | WO 2007/073552 | 6/2007 |
| WO | WO 2007/079183 | 7/2007 |
| WO | WO 2007/087292 | 8/2007 |
| WO | WO 2007/087293 | 8/2007 |
| WO | WO 2007/124594 | 11/2007 |
| WO | WO 2007/136673 | 11/2007 |
| WO | WO 2007/141657 | 12/2007 |
| WO | WO 2008/019148 | 2/2008 |
| WO | WO 2008/036374 | 3/2008 |
| WO | WO 2008/036447 | 3/2008 |
| WO | WO 2008/051568 | 5/2008 |
| WO | WO 2008/060541 | 5/2008 |
| WO | WO 2008/100497 | 8/2008 |
| WO | WO 2008/148105 | 12/2008 |
| WO | WO 2008/152640 | 12/2008 |
| WO | WO 2008/156659 | 12/2008 |
| WO | WO 2009/007979 | 1/2009 |
| WO | WO 2009/028870 | 3/2009 |
| WO | WO 2009/035612 | 3/2009 |
| WO | WO 2009/037690 | 3/2009 |

(56) References Cited

FOREIGN PATENT DOCUMENTS

| | | |
|---|---|---|
| WO | WO 2009/045360 | 4/2009 |
| WO | WO 2009/046346 | 4/2009 |
| WO | WO 2009/046377 | 4/2009 |
| WO | WO 2009/052132 | 4/2009 |
| WO | WO 2009/134532 | 11/2009 |
| WO | WO 2009/144720 | 12/2009 |
| WO | WO 2010/021714 | 2/2010 |
| WO | WO 2012/009422 | 1/2012 |
| WO | WO 2013/012698 | 1/2013 |

OTHER PUBLICATIONS

U.S. Appl. No. 13/473,509, filed May 16, 2012, Edinger et al.
U.S. Appl. No. 13/480,370, filed May 24, 2012, Edinger et al.
U.S. Appl. No. 13/542,269, filed Jul. 5, 2012, Seehra et al.
U.S. Appl. No. 13/584,612, filed Aug. 13, 2012, Hariri et al.
U.S. Appl. No. 13/610,375, filed Sep. 11, 2012, Bhatia et al.
U.S. Appl. No. 13/650,803, filed Oct. 12, 2012, Heidaran et al.
U.S. Appl. No. 13/654,191, filed Oct. 17, 2012, Heidaran et al.
U.S. Appl. No. 13/711,331, filed Dec. 11, 2012, Hariri et al.
U.S. Appl. No. 13/727,217, filed Dec. 26, 2012, Hariri et al.
Abe, "Therapeutic Potential of Neurotrophic Factors and Neural Stem Cells Against Ischemic Brain Injury," Journal of Cerebral Blood Flow and Metabolism, Raven Press, Ltd., New York, 20(10): 1393-1408 (2000).
Abkowitz, "Can Human Hematopoietic Stem Cells Become Skin, Gut, or Liver Cells?" N. Engl. J. Med. 346(10):770-2 (2002).
Aboagye-Mathiesen et al., "Isolation and Characterization of Human Placental Trophoblast Subpopulations from First-Trimester Chorionic Villi," Clinical and Diagnostic Laboratory Immunology 3(1):14-22 (1996).
Addison, et al., "Metabolism of Prednisolone by the Isolated Perfused Human Placental Lobule," J. Ster. Biochem. Mol. Biol., 39(1):83-90 (1991).
Aggarwal, et al., "Human Mesenchymal Stem Cells Modulate Allogeneic Immune Cell Responses," Blood 105(4):1815-22 (2005).
Alviano, et al., "Term amniotic membrane is a high throughput source for multipotent mesenchymal stem cells with the ability to differentiate into endothelial cells in vitro," BMC Developmental Biology, vol. 7, No. 1, Feb. 2007.
Anker In't P, et al., "Isolation of Mesenchymal Stem Cells of Fetal or Maternal Origin from Human Placenta," Stem Cells 22: 1338-45 (2004).
Anseth et aL., J. Control Release 78(1-3): 199-209 (2002).
Aplin, "Implantation, trophoblast Differentiation and Haemochorial Placentation: Mechanistic Evidence in vivo and in vitro," Journal of Cell Science 99:681-692 (1991).
Ashihara, et al., "Successful Peripheral Blood Stem Cell Transplantation for Myelodysplastic Syndrome," Bone Marrow Transplantation 24(12): 1343-1345 (1999).
Bailo, et al., "Engraftment Potential of Human Amnion and Chorion Cells Derived from Term Placenta," Transplantation 78:1439-1448 (2004).
Ballin, et al., "Autologous Umbilical Cord Blood Transfusion," Arch. Dis. Child Fetal Neonatal. Ed. 73(3):F181-F183 (1995).
Barlogie et al., "High-dose therapy immunomodulatory drugs in multiple myeloma," Seminars in Oncology, 2002, 29 (6):26-33.
Barlow et al., "Comparison of Human Placenta- and Bone Marrow-Derived Multipotent Mesenchymal Stem Cells," Stem Cells and Development 17:1095-1108 (2008).
Barry et al., Birth Defect Research (Part C) 69:250-256, (2003).
Barry et al., "The Monoclonal Antibody SH-2, Raised Against Human Mesenchymal Stem Cells, Recognizes an Epitope on Endoglin (CD105)," Osiris Therapeutics Inc., 2001 Aliceanna Street, Baltimore, MD 21231, Biochemical and Biophysical Research Communications 265:134-139 (1999).
Barry, "Where do all the placentas go?" Canadian Journal of Infection Control 9(1):8-10 (1994).
Bartlett et al., "Phase I study to determine the safety, tolerability and immunostimulatory activity of thalidomide analogue CC-5013 in patients with metastatic malignant melanoma and other advanced cancers," British Journal of Cancer, 2004, 90:955-961.
Battula et al., "Prospective Isolation and Characterization of Mesenchymal Stem Cells from Human Placenta Using a Firzzled-9-Specific Monoclonal Antibody," Differentiation 76:326-336 (2008).
Belvedere, et al., "Increased Blood Volume and CD34(+)CD38(−) Progenitor Cell Recovery Using a Novel Umbilical Cord Blood Collection System," Stem Cells 18(4):245-251 (2000).
Bernardeschi et al., 2003, J. Exp. Clin. Cancer Res. 22(4):129-133.
Bersinger, et al., "Effect of Late Pregnancy Serum on the Synthesis and Release of Pregnancy Proteins by the Perfused Human Term Placenta," Reprod. Fertil. Dev. 4:585-588 (1992).
Bertolini, et al., "Retrovirus-Mediated Transfer of the Multidrug Resistance Gene into Human Haemopoietic Progenitor Cells." Haemolotol. 88:318-324 (1994).
Bloxam et al., "Culture of Syncytiotrophoblast for the Study of Human Placental Transfer. Part I: Isolation and Purification of Cytotrophoblast," Placenta 18:93-98 (1997).
Bloxam, "Human Placental Trophoblast Culture: One-Sided and Two-Sided Models," Proceedings of the Nutrition Society 50:349-354 (1991).
Bossolasco et al., "Molecular and phenotypic characterization of human amniotic fluid cells and their differentiation potential," Cell Research 16:329-336 (2006).
Bullen et al., "Two-Sided Culture of Human Placental Trophoblast. Morphology, Immunocytochemistry and Permeability Properties," Placenta 11:431-450 (1990).
Campagnoli, et al., "Identification of Mesenchymal Stem/Progenitor Cells in Human First-Trimester Fetal Blood, Liver, and Bone Marrow." Blood 98(8):2396-402 (2001).
Caniggia et al., "Oxygen and Placental Development During the First Trimester: Implications for the Pathophysiology of Pre-Eclampsia," PubMed, Placenta 21(Suppl A):S25-30 (2000).
Caplan, "The Mesengenic Process," Clin. Plast. Surg. 21(3):429-435 (1994).
Carter, et al., "Characterization of MSC Potential to Treat GVHD Using Molecular Markers Linked to MSC-Mediated Immunosuppression in Vitro," Blood, 106(11) part 2, Abstract No. 4322, 160B (2005).
Celgene Corporation, "Celgene expands clinical development program for Revimid™. Five additional trials of Revimid initiated in hematological and solid tumor cancers," Press Release, Jun. 2002.
Celgene Corporation, "Initial Phase I solid tumor data on Celgene's lead IMiD™, Revimid™," Press Release, Jun. 2001.
Cester et al., "Cation Transport Across Cultured Trophoblast Membrane in Preeclampsia," Clin. And Exper. Hyper. In Pregnancy, B11(1):59-69 (1992).
Chang, et al., "Placenta-Derived Multipotent Cells Exhibit Immunosuppressive Properties That Are Enhanced in the Presence of Interferon-gamma," Stem Cells 24:2466-2477 (2006).
Chao, et al., "Stem Cell Transplantation (Cord Blood Transplants)." American Society of Hematology p. 354-371 (2004).
Chen, et al. "Intravaneous Administration of Human Umbilical Cord Reduces Behavioral Deficits after Stroke in Rats," Stroke 32(11): 2682-2688 (2001).
Chen, et al., "The Potential for the Use of Mononuclear Cells from Human Umbilical Cord Blood in the Treatment of Amyotrophic Lateral Sclerosis is SOD1 Mice," J. Med. 31(1-2):21-30 (2000).
Chen, et al., "Therapeutic Benefit of Intravenous Administration of Bone Marrow Stromal Cells after Cerebral Ischemia in Rats," Stroke, 32(4):1005-11 (2001).
Chies et al., "Sickle Cell Disease: A Chronic Inflammatory Condition," Medical Hypotheses 57(1):46-50 (2001).
Chin, et al., "Enhanced Interferon Production and Lymphokine-Activated Cytotoxicity of Human Placental Cells," Cellular Immunology 113:1-9 (1988).
Clark et al., "Placental Trophoblast from Successful Human Pregnancies Expresses the Tolerance Signaling Molecule, CD200 (OX-2)" Am. J. Reprod. Immunol., 50(3):187-195 (2003).
Conget et al., "Phenotypical and functional properties of human bone marrow mesenchymal progenitor cells" Journal of Cellular Physiology 181:67-73 (1999).

(56) References Cited

OTHER PUBLICATIONS

Contractor, et al., "A comparison of the effects of different perfusion regimens on the structure of the isolated human placental lobule," Cell Tissue Res. 237:609-617 (1984).
Cosma, et al., "Use and Application of Stem Cells in Toxicology," SOT 2003 Annual Meeting, p. 4, Abstract 19 (2003).
Cotte et al., "Preparation of Highly Purified Cytotrophoblast from Human Placenta with Subsequent Modulation to Form Syncytiotrophoblast in Monolayer Cultures," In Vitro 16(8):639-646 (1980).
Czarneski, et al., "Effects of Cord Blood Transfer on the Hematopoietic Recovery Following Sublethal Irradiation in MRL lpr/lpr Mice," Proc. Soc. Exp. Biol. Med. 220(2):79-87 (1999).
D'Amato et al., 2001, "Mechanism of action of thalidomide and 3-aminothalidomide in multiple myeloma," Semin. Oncol. 28:597-601.
Dalgleish, et al., "New thalidomide analogues; anti-cancer, anti-angiogenic and immunostimulatory," *British Journal of Cancer*, 2001, 85 (1)25.
Dallas, et al., "Enhanced T Cell Reconstitution by Hematopoietic Progenitors Expanded ex vivo Using The Notch Ligand Delta1," Blood 109:3579-3587 (2007).
Davani, et al., "Mesenchymal Progenitor Cells Differentiate into an Endothelial Phenotype, Enhance Vascular Density, and Improve Heart Function in a Rat Cellular Cardiomyoplasty Model," Circulation 108[suppl II]:II-253-II-258 (2003).
Davies, et al. "Thalidomide and Immunomodulatory Derivatives Augment Natural Killer Cell Cytotoxicity in Multiple Myeloma," Blood 98(1):210-216 (2001).
Davies, et al., "Engraftment and Survival After Unrelated-Donor Bone Marrow Transplantation: A Report from the National Marrow Donor Program," Blood, 96(13): 4096-4102, (2000).
Davila, et al., "Use and Application of Stem Cells in Toxicology," Toxicological Sciences 79:214-223 (2004).
De Coppi, et al., "Amniotic Fluid and Chorionic Villi Derived Human Stem Cells for the Engineering of Tissues in Vivo." The Journal of Urology, vol. 171, No. 4, Supplement, Saturday, May 8, p. 21, Abstract 81 (2004).
De Coppi, et al., "Human Embryonic and Fetal Stem-Cell Isolation from Amniotic Fluid and Placenta for Tissue Reconstruction." Urology and Reproductive Surgery, vol. 195, No. 3S, Sep. 2002, p. S93.
De Coppi, et al., "Human fetal stem cell isolation from amniotic fluid for tissue reconstruction," J. Urology 167(4 Supp.) 85 (Abstract 338) (2002).
De Coppi, et al., "Pluripotent Stem Cells Derived from Human Chronic Villi and Amniotic Fluid for Tissue Engineering Applications." Experimental Biology/UPS Meeting Abstracts, A1366, Abstract 781.7 (2005).
De Flippo, et al., "Total Penile Urethra Replacement with Autologous Cell-Seeded Collagen Matrices." Urology and Reproductive Surgery, vol. 195, No. 3S, Sep. 2002, p. S95.
De Wynter, et al., "CD34+AC133+ Cells Isolated from Cord Blood are Highly Enriched in Long-Term Culture-Initiating Cells, NOD/SCID-Repopulating Cells and Dendritic Cell Progenitors," Stem Cells 16(6):387-396 (1998).
Delrome et al., Blood 111:2631-2635, Online Dec. 17, 2007 (2008).
Denison et al., "Cytokine Secretion by human fetal membranes, decidua and placenta at term" Human Reproduction 13(12):3560-3565 (1998).
Dominici, et al., "Minimal Criteria for Defining Multipotent Mesenchymal Stromal Cells. The International Society for Cellular Therapy Position Statement," Cytotherapy 8(4):315-317 (2006).
Drake, et al., "Human Placental Cytotrophoblasts Attract Monocytes and CD56 (Bright) Natural Killer Cells Via the Actions of Monocyte Inflammatory Protein 1Alpha," J. Exp. Med. 193(10):1199-1212 (2001).
Dushnik-Levinson, et al., "Embryogenesis in vitro: study of differentiation of embryonic stem cells." Biol Neonate. 67(2):77-83 (1995).

Elchalal, et al., "Postpartum Umbilical Cord Blood Collection for Transplantation: a Comparison of Three Methods," Am. J. of Obstetrics & Gyn. 182(1 Pt 1):227-232 (2000).
Ende, "Berashis Cells in Human Umbilical Cord Blood Vs. Embryonic Stem Cells," J. Med. 33(1-4):167-171 (2002).
Ende, "Collection of Umbilical Cord Blood for Transplantation," Blood 80(6):1623-1624 (1992).
Ende, "The Feasibility of Using Blood Bank Stored (4° C) Cord Blood, Unmatched for HLA for Marrow Transplantation," Am. Clin. Pathol. 111:773-781 (1999).
Ende, et al., "Human Umbilical Cord Blood Cells Amerliorate Alzheimer's Disease in Transgenic Mice," J. Med. 32(3-4):241-7 (2001).
Ende, et al., "Human Umbilical Cord Blood Cells Ameliorate Huntington's Disease in Transgenic Mice," J. Med. 32(3-4):231-240 (2001).
Ende, et., "Human Umbilical Cord Blood Effect on SOD Mice (Amyotrophic Lateral Sclerosis)," Life Sci. 67(1):53-59 (2000).
Ende, et al., "Parkinson's Disease Mice and Human Umbilical Cord Blood," Journal of Medicine 33(1-4):173-180 (2002).
Ende, et al., "Pooled Umbilical Cord Blood as a Possible Universal Donor for Marrow Reconstitution and Use in Nuclear Accidents," Life Sci. 69:1531-1539 (2001).
Ende, et al., "The Effect of Human Cord Blood on SJL/J Mice After Chemoablation and Irradiation and Its Possible Clinical Significance," Immunol. Invest. 24(6):999-1012 (1995).
Erices, et al., "Mesenchymal Progenitor Cells in Human Umbilical Cord Blood," Br. J. Haemotol. 109(1):235-242 Abstract (2000).
Evans, "Stem Cell Therapy: Moving towards Reality," Am. J. Obstet. Gynecol. 194:662-663 (2006).
Fasouliotis, et al., "Human umbilical cord blood banking and transplantation: a state of the art," Eur. J. Obstet. Gynecol. Reprod. Biol. 90(1):13-25 (2000).
Fisher et al., "Adhesive and Degradatie Properties of Human Placental Cytotrophoblast Cells in Vitro," Journal od Cell Biology 109:891-902 (1989).
Frank H G, et al., "Cell culture models of human trophoblast: primary culture of trophoblast—a workshop report." Placent Apr. 2001, vol. 22 Suppl A, pp. S107-S109, XP002443188 ISSN: 0143-4004 (Apr. 2001).
Genbacev et al., "Regulation of Human Placental Development by Oxygen Tension," 277(5332):1669-1672 (1997).
Gluckman, et al., "Cord Blood Heamatopoietic Stem Cells: Biology and Transplantation," In: Hematology, American Society of Hematology Education Program Book p. 1-14 (1998).
Gluckman, et al., "Results of Unrelated Umbilical Cord Blood Hematipoeietic Stem Cell Transplant," Transfusion Cinique et Biologique 8(3):146-154 (2001).
Greenwood et al., "Membrane Potential Difference and Intracellular Cation Concentrations in Human Placental Trophoblast Cells in Culture," Journal of Physiology 492.3:629-640 (1996).
Hadjantonakis, et al., "The Stem Cells of Early Embryos," Differentiation 68:159-166 (2001).
Hamada, et al., "Mesenchymal Stem Cells (MSC) as Therapeutic Cytoreagents for Gene Therapy," Cancer Sci 96:149-156 (2005).
Harbacheuski, et al., "Placenta Derived Adherent Cells (PDACs) Supress Tumor Cells of Diverse Origin." Blood 108(11):288 (2006).
Harun et al., "Cytotrophoblast Stem Cell Lines Derived from Human Embyonic Stem Cells and Their Capacityt o Mimic Invasive Implantation Events," Human Reproduction, Oxford University Press, pp. 1-10 (2006).
Hattori et al., "Molecular Cloning of Adipocyte-Derived Leucine Aminopeptidase Highly Related to Placental Leucine Aminopeptidase/Oxytocinase," J. Biochem. 125(5):931-938 (1999).
Hatzopoulos, et al. "Isolation and characterization of endothelial progenitor cells from mouse embryos," Development. 125(8):1457-68 (1998).
Heidaran, Disclosure Document No. 457045 for "A Method or Process for the Treatment of Degenerative Conditions or Cancer Employing Custom Fabricated Organ Tissue Grafts Using Cells Isolated, Expanded, and Stored at Birth", 15 pages, stamped received by OIPE on May 28, 1999, paper dated May 13, 1999.

(56) References Cited

OTHER PUBLICATIONS

Herrera, et al., "Mesenchymal Stem Cells Contribute to the Renal Repair of Acute Tubular Epithelial Injury,"• Int. J. Mol. Med., 2004: 14(6):1035-41.
Himori, et al., Chemotherapeutic susceptibility of human bone marrow progenitor cells and human myelogenous leukemia cells (HL-60) in co-culture: preliminary report. Int J Cell Cloning. 2(4):254-62 (1984).
Hirano et al., "CD9 is Expressied in Extravillous Trophoblasts in Association with Integrin α3 and integrin α5," Molecular Human Reproduction 5(2):162-167 (1999).
Hirashima, et al. "Maturation of embryonic stem cells into endothelial cells in an in vitro model of vasculogenesis," Blood. 93(4):1253-63 (1999).
Hoek R M, et al., "Down-regulation of the macrophage lineage though interaction with OX2 (CD200)" Science, American Association for the ADvancement of Science, US, vol. 290, No. 5497, Dec. 1, 2000, pp. 1768-1771, XP002263649 ISSN:0036-8075.
Hoshimaru et al., Proc. Natl. Acad. Sci. USA 93:1518-1523 (1996).
Hows, "Status of Umbilical Cord Blood Transplantation in the Year 2001," J Clin Pathol 54(6):428-434 (2001).
Hoynowski, et al., "Characterization and Differentiation of Equine Umbilical Cord-Derived Matrix Cells,"• Biochemical and Biophysical Research Communications, 2007; 362:347-53.
Huss, "Isolation of Primary and Immortalized CD34—Hematopoietic and Mesenchymal Stem Cells from Various Sources," Stem Cells 18:1-9 (2000).
Huss, "Perspectives on the Morphology and Biology of CD34—Negative Stem Cells," J. Hematother. Stem. Cell Res. 9(6):783-793 (2000).
Igura, et al., "Isolation and Characterization of Mesencymal Progenitor Cells from Chorionic Villi of Human Placenta," Cytotherapy 6(6): 543-553 (2004).
Ino et al., "Expression of Placental Leucine Aminopeptidase and Adipoctye-Derived Leucine Aminopeptidase in Human Normal and Malignant Invasive Trophoblastic Cells" Laboratory Investigation 83(12):1799-1809 (2003).
Iwasaki, "Recent Advances in the Treatment of Graft-Versus-Host Disease,"• Clin. Med. Res., 2004; 2(4):243-52.
Jaiswal, et al., "Osteogenic Differentiation of Purified, Culture-Expanded Human Mesenchymal Stem Cells in vitro," J. Cell Biochem. 64(2):295-312 (1997).
James et al., "Cytotrophobast Differentiation in the First Trimester of Pregnancy: Evidence for Separate Progenitros of Extravillous Trophoblasts and Syncytiotrophoblast," Reproduction 130:95-130 (2005).
Jiang et al., "Hypoxia Prevents Induction of Aromatase Expression in Human Trophoblast Cells in Culture: Potential Nihibitory Role of the Hypoxia-Inducible Transcription Factor Mash-2 (Mammalian Achaete-Scute Homologous Protein-20," Molecular Endocrinology 14(10):1661-1673 (2000).
Joggerst et al., "Stem Cell Therapy for Cardiac Repair: Benefits and Barriers," Expert Rev. Mol. Med. 11(e20):1-19 (2009).
Jones et al., "Isolation and Characterization of Bone Marrow Multipotential Mesenchymal Progenitor Cells," Arthritis Rheum. 46(12):3349-3360 (2002).
Jones et al., "Ultrastructure of the Normal Human Placenta," Electron Microsc. 4:129-178 (1991).
Kao et al., "The Human Villous Cytotrophoblast: Interactions with Extracellular Matrix Proteins, Endocrine Function, and Cytoplasmic Differentiation in the Absence of Syncytium Formation," Developmental Biology 130:693-702 (1988).
Kato et al., "Discordant Secretion of Placental Protein Hormones in Differentiating Trophoblasts in Vitro," Journal of Clinical Endocrinology and Metabolism 68(4):814-820 (1989).
Kaufmann et al., "Extravillous Trophoblast in the Human Placenta," Trophoblast Research 10:21-65 (1997).
Kavalerchik E et al. "Chronic myeloid leukemia stem cells," J Clin Oncol 26:2911-2915(2008).
Kawata et al., "Transcriptional Control of HLA-A,B,C Antigen in Human Placental Cytotrophoblast Isolated Using Trophoblast- and HLA-Specific Monoclonal Antibodies and the Fluorescence-Activated Cell Sorter," J. Exp. Med. 160(3):633-51 (1984).
Kliman et al., "Purification, Characterization, and In Vitro Differentiation of Cytotropholblasts from Human Term Placentae," Endocrinology 118(4):1567-1582 (1986).
Koc, et al., "Rapid Hematopoietic Recovery After Coinfusion of Autologous-Blood Stem Cells and Culture-Expanded Marrow Mesenchymal Stem Cells in Advanced Breast Cancer Patients Receiving High-Dose Chemotherapy," J Clin Oncol 18:307-316 (2000).
Koh, et al., "Parthenolgenetically Derived Stem Cells for Urologic Reconstruction." The Journal of Urology, vol. 171, No. 4, Supplement, Saturday, May 8, 2004, p. 21, Abstract 81.
Korbling, et al., "Hepatocytes and Epithelial Cells of Donor Origin in Recipients of Peripheral-Blood Stem Cells," N. Engl. J. Med. 346(10):738-746 (2002).
Kurtzberg, "Placental Bood as a Source of Hmatopoietic Sem Cells for Transplantation into Unrelated Recipients," N. Engl. J. Med. 335:157-166 (1996).
Landon et al., "The Effects of Ethanol Methotrexate and Diphenylhydantoin on [$^{14}$C] Leucine Incorporation by Human Trophoblast Cells Cultured In Vitro," British Journal of Obstetrics and Gynaecology 94:252-255 (1987).
Lapchak et al., Expert Opin. Emerging Drugs 12:389-406 (2007).
Law, E., et al., Stem Cell Symposium, State of New Jersey Commission on Science & Technology 2005 (Abstract).
Lazarus, et al., "Cotransplantation of HLA-Identical Sibling Culture-Expanded Mesenchymal Stem Cells and Hematopoietic Stem Cells in Hematologic Malignancy Patients," Biol Blood Marrow Transplant, 11(5):389-398 (2005).
Le Blanc et al., "Treatment of Severe Acute Graft-Versus-Host Disease With Third Party Haploidentical Mesenchvmal Stem Cells,"• Lancet, 363(9419):1439-41 (2004).
Lebkowski, et al., "Serum and Plasma Levels of FGF-2 and VEGF in Healthy Blood Donors," Cancer J. 7(Suppl 2):S83-S93 (2001).
Leblanc et al., "Immunomodulatory drug costimulates T cells via the B7-CD28 pathway," *Blood*, 2004, 103:1787-1790, *American Society of Hematology*.
Leonard, et al., "The Role of ABC Transporters in Clinical Practice," Oncologist. 8:411-424 (2003).
Li et al., "Mesenchymal Stem Cells Derived from Human Placenta Suppress Allogenic Umbilical Cord Blood Lymphocyte Proliferation." Cell Res. 15: 539-547 (2005).
Li et al., Br. J. Haematology 138(6):802-811 (2007).
Lin, et al. "Murine CD200(+)CK7(+) trophoblasts in a poly (I:C)-induced embryo resorption model." Reproduction (Cambridge), vol. 130, No. 4, pp. 529-537, XP002443406 ISSN: 1470-1626 (2005).
Lipinski et al., "Human Trophoblast Cell-Surface Antigen Defined by Monoclonal Antibodies," Proc. Natl. Acad. Sci. USA, Medical Sciences 78(8):5147-5150 (1981).
Loke et al., "Identification of Cytotrophoblast Colonies in Cultures of Human Placental Cells Using Monoclonal Antibodies," Placenta 7:221-231 (1986).
Lorkowski, et al., "ABCG Subfamily of Human ATP-Binding Cassette Proteins," Pure Appl. Chem. 74(11):2057-2081 (2002).
Lowy, et al. "Isolation of transforming DNA: cloning the hamster aprt gene," Cell. 22(3):817-23 (1980).
Ma et al., "Development of an in vitro Human Placenta Model by the Cultivation of Human Trophoblasts in a Fiber-Based Bioreactor System," Tissue Engineering 5, 91-102 (1999).
Ma et al. "Human Umbilical Cord Wharton's Jelly-Derived Mesenchymal Stem Cells Differentiation into Nerve-Like Cells," Chinese Med. Jour., 118(23):1987-1993 (2005).
Mackay, et al., "Chondrogenic Differentiation of Cultured Human Mesenchymal Stem Cells from Marrow," Tissue Engineering 4(4):415-28 (1998).
Malek et al. "Lack of transport of erythropoietin across the human placenta as studied by an in vitro perfusion system," European Journal of Physiology 427:157-161 (1994).

(56) References Cited

OTHER PUBLICATIONS

Marmont, "New Horizons in the Treatment of Autoimmune Diseases: Immunoablation and Stem Cell Transplantation," Ann. Rev. Medicine 51:115-134 (2000).
McMaster et al, "Human Placental HLA-G Expression is Restricted to Differentiated Cytotrophoblasts," J. Immunol. 154(8):3771-3778 (1995).
Melchner, et al., "Human Placental Conditioned Medium Reverses Apparent Commitment to Differentiation of Human Promyelocytic Leukemia Cells (HL60)," Blood 66(6):1469-1472 (1985).
Melnik, et al., "Evaluation of Eluants from Batch Separations of CD34(+) Cells from Human Cord Blood Using a Commercial, Immunomagnetic Cell Separation System," Biotechnol. Prog. 17(5):907-916 (2001).
Miki et al., "Isolation of Multipotent Stem Cells from Placenta." AASLD Abstracts, Hepatology, Abstract 279, p. 290A (Oct. 2003).
Miki et al., "Production of Hepatocytes from Human Amniotic Stem Cells." Hepatology, Abstract 20, vol. 36, No. 4, Pt. 2 (2002).
Miki et al., "Stem Cell Characteristics of Amniotic Epithelial Cells." Stem Cells Express, published online Aug. 9, 2005; doi:10.1634/stemcells:2004-0357 (2005).
Minguell, et al., "Mesenchymal Stem Cells," Exp. Biol. Med. 226:507-520 (2001).
Moore, et al., "A Simple Perfusion Technique for Isolation of Maternal Intervillous Blood Mononuclear Cells from Human Placentae," J. Immunol. Methods 209(1):93-104 (1997).
Moreau et al., "Myofibroblastic Stromal Cells Isolated From Human Bone Marrow Indue the Proliferation of Both Early Myeloid and B-Lymphoid Cells," Blood 82:2396-2405 (1993).
Moreira et al., "Thalidomide Exerts its Inhibitory Action on Tumor Necrosis Factoraby Enhancing mRNA Degradation," J. Expr. Med. 177: 1675-1680 (1993).
Morgan et al., "Human Placental Cell Culture," Biochemical Society Transactions 12 (1984).
Morgan et al., "Long-Term Culture of Human Trophoblast Cells," British Journal of Obstetrics and Gynaecology 92:84-92 (1985).
Morigi, et al., "Mesenchymal Stem Cells are Renotropic, Helping to Repair the Kidney and Improve Function in Acute Renal Failure," J. Am. Soc. Nephrol., 15(7):1794-1804 (2004).
Morishima, et al., "The Clinical Significance of Human Leukocyte Antigen (HLA) Allele Compatibility in Patients Receiving a Marrow Transplant from Serologically HLA-A, HLA-B, and HLA-DR Matched Unrelated Donors," Blood, 2002; 99(11):4200-06.
Morrish et al., "Epidermal Growth Factor Induces Differentiation and Secretion of Human Chorionic Gonadotropin and Placental Lactogen in Normal Human Placenta," Journal of Clinical Endocrinology and Metabolism 65(6):1282-1290 (1987).
Morrish et al., "In Vitro Cultured Human Term Cytotrophoblast: A Model for Normal Primary Epitehlial Cells Demonstrating a Spontaneous Differentiation Programme that Requires EGF for Extensive Development of Syncytium," Placenta 18: 577-585 (1997).
Muhlemann, et al., "Cytomegalovirus in the Perfused Human Term Placenta in vitro," Placenta 16:367-373 (1995).
Myllynen "In Search of Models for Hepatic and Placental Pharmacokinetics," [Dissertation] University of Oulu, (2003).
Nagayama et al., "Immunological reconstitution after cord blood transplantation for an adult patient", Bone Marrow Transplantation 24: 211-213 (1999).
Ninichuk, et al., "Multipotent Mesenchymal Stem Cells Reduce Interstitial Fibrosis but do not Delay Progression of Chronic Kidney Disease in Collagen4a3-Deficient Mice," Kidney Int., 2006; 70(1):121-29.
Nishishita, et al., "A Potential Pro-Angiogenic Cell Therapy with Human Placenta-Derived Mesenchymal Cells," Biochem. Biophys. Res. Commun. 325(1):24-31 (2004).
Noort, et al., "Mesenchymal Stem Cells Promote Engraftment of Human Umbilical Cord Blood-Derived CD34+ Cells in NOD/SCID Mice," Experimental Hematology 30(8):870-878 (2002).
Notice of Opposition by Farmindustria S.A. to corresponding claims filed in Peru; English translation Jan. 18, 2008.

Oda et al., "Trophoblast Stem Cells," Methods in Enxymology 419(15):387-400 (2006).
Paludan, et al., "Immune Suppression by Placenta Derived Adherent Cells (PDAC) Correlate with Monocyte Chemoattractant Protein-1 and 1L-2 Secretion," Blood 108(11) Part II, p. 48B (2006) (abstract only).
Paludan, et al., "Placental Derived Stem Cells (PDAC) Suppress the Allo-MLR and the EBV Regression Assay," http://www.call4abstract.com/hem/finalpreview.php?absnum=552996 (2006).
Pande et al., "Isolation and Culture of Hamster Ectoplacental Cone Trophoblasts: an In Vitro Study on the Cell Types and Their Growth Pattern," Cell Prolif. 29:163-171 (1996).
Panepucci, et al., "Comparison of Gene Expression of Umbilical Cord Vein and Bone Marrow-Derived Mesenchvmal Stem Cells," Stem Cells, 2004; 22(7):1263-78.
Papaioannou, et al., "Stem Cells from Early Mammalian Embryos" Stem Cells Handbook:19-31 (2004).
Parolini, et al., "Concise Review: Isolation and Characterization of Cells from Human Term Placenta: Outcome of the First International Workshop on Placenta Derived Stem Cells," Stem Cells 26(2):300-311 (2008).
Pellegrini, et al., "FADD and Caspase-8 Are Required for Cytokine-Induced Proliferation of Hemopoietic Progenitor Cells," Blood 106(5):1581-1589 (2005).
Pera, et al., "Human Embryonic Stem Cells," J. Cell. Sci. 113:5-10 (2000).
Petroff et al., "Isolation and Culture of Term Human Trophoblast Cells," Methods in Molecular Medicine, Placenta and Trophoblast, 1(16):203-217 (2006).
Pinho-Ribeiro et al., "Human Umbilical Cord Blood Cells in Infarcted Rats," Braz. J. Med. Biol. Res. 43(3):290-296 (2010).
Pittenger et al., "Multilineage Potential of Adult Human Mesenchymal Stem Cells," Science 284(5411):143-147 (1999).
Pluristem. Pluristem Therapeutics Receives DSMB Approval to Advance to Final Dose Level with PLX-PAD [online] Mar. 2, 2010 [retrieved Jun. 22, 2011], Available on the Internet: <URL:http://www.pluristem.com/index.php?option=com_content&view=article&id=148:march-2&catid=5:2010>.
Portmann-Lanz, et al., "Placental Mesenchymal Stem Cells as Potential Autologous Graft for Pre- and Perinatal Neuroregeneration" Am. J. Obstet Gynecol. 194:664-673 (2006).
Potgens et al., "Human Trophoblast Contains an Intracellular Protein Reactive with and Antibody against CD133-A Novel Marker for Trophoblast," Placenta 22:639-645 (2001).
Potgens et al., "Monoclonal Antibody CD133-2 (AC141) Against Hematopoeietic Stem Cell Antigen CD133 Shows Crossactivity with Cytokeratin 18," Journal of Histochemistry & Cytochemistry 50(8):1131-1134 (2002).
Pountos, et al., "Mesenchymal Stem Cell Tissue Engineering: Techniques for Isolation, Expansion and Application," Injury Int. J. Care Injured, 2007; 38(Supp. 4):S23-33.
Quinn et al., "Mouse Trophoblast Stem Cells," Methods in Molecular Medicine 121(1):125-148 (2005).
Rachmilewitz et al., "Intermediate Cells During Cytotrphoblast Differentiation in Vitro," Cell Growth & Differentiation 4:395-402 (1993).
Reyes, et al., "Purification and ex vivo Expansion of Postnatal Human Marrow Mesodermanl Progenitor Cells," Blood 98(9):2615-2625 (2001).
Reyes, et al., Origin of endothelial progenitors in human postnatal bone marrow.J Clin Invest. 109(3):337-46 (2002).
Rielland et al., "Trophoblast Stem Cell Derivation, Cross-species Comparison and Use of Nuclear Transfer: New Tools to Study Trophoblast Growth and Differentiation," Developmental Biology 322:1-10 (2008).
Rong-Hao et al., "Establishment and Characterization of a Cytotrophoblast Cell Line From Normal Placenta of Human Origin," Human Reproduction 11(6):1328-1333 (1996).
Rossant, "Stem Cells from the Mammalian Blastocyst," Stem Cell 19:477-482 (2001).
Roth, et al., "Human Placental Cytotrophoblats Produce the Immunosuppressive Cytokine Interliukin 10," J. Exp. Med. 184(2):539-548 (1996).

(56) References Cited

OTHER PUBLICATIONS

Rubinstein, et al., "Processing and Cryopreservation of Placental/Umbilical Cord Blood for Unrelated Bone Marrow Reconstitution," Proc. Natl. Acad. Sci. USA 92:10119-10122 (1995).
Russo, "Fighting Darwin's Battles. Symposium Marks Evolutionist Victory, Anti-Evolution Growth" The Scientist 15:6 (2001).
Sakuragawa, et al., "Expression of markers for both neuronal and glial cells in human amniotic epithelial cells," Neuroscience Letters 209:9-12 (1996).
Sakuragawa, et al., "Human amniotic epithelial cells are promising transgene carriers for allogeneic cell transplantation into liver," J. Hum. Genet. 45:171-176 (2000).
Sapin, "Esterification of Vitamin A by the Human Placenta Involves Villous Mesenchymal Fibrlboasts," pediatric Research 48(4):565-572 (2000).
Saric et al., "An IFN-γ-induced Aminopeptidase in the ER, ERAP I, Trims Precursors to MHC Class I-presented Peptides," Nature Immunology 3(12):1169-1176 (2002).
Schulz et al., "Human Embryonic Stem Cells as Models for Trophoblast Differentiation," Placenta 29(Suppl A):S10-S16 (2008).
Schutz, et al., "Isolation and Cultivation of Endothelial Cells Derived from Human Placenta," Eur. J. Cell Biol. 395-401 (1996).
Schwab, "Fast and Reliable Culture Method for Cells from 8-10 Week Trophoblast Tissue," Lancet 323:1082 (1984).
Semenov et al. "Multipotent mesenchymal stem cells from human placenta: critical parameters for isolation and maintenance of stemness after isolation" American Journal of Obstetrics & Gynecolocy 202:193.e1-13 (2010).
Seyfried et al., J. Neurosurg. 104:313-318 (2006).
Shamblott, et al., "Derivation of Pluripotent Stem Cells from Cultured Human Primordial Germ Cells," Proc. Natl. Acad. Sci. USA 95(23):13726-13731 (1998).
Sherley, "Asymmetric Cell Kinetics Genes: The Key to Expansion of Adult Stem Cells in Culture", Stem Cell 20:561-72 (2002).
Shuto, et al., "Dexamethasone Stimulates Osteoclast-Like Cell Formation by Inhibiting Granulocyte-Macrophage Colony-Stimulating Factor Production in Mouse Bone Marrow Cultures," Endocrinology 134:1121-1126 (1994).
Sikkema-Raddatz, "Four Years' Cytogenetic Experience with the Culture of Chorionic Villi," Prenatal Diagnosis 20:950-955 (2000).
Sirchia, et al., "Placental/Umbilical Cord Blood Transplantation," Haematologica 84:738-747 (1999).
Slager, Transforming growth factor-beta in the early mouse embryo: implications for the regulation of muscle formation and implantation. Dev Genet. 14(3):212-24 (1993).
Soma, "Human Trophoblast in Tissue Culture," Obstetrics and Gynaecology 18(6):704-718 (1961).
Soncini, et al., "Isolation and Characterization of Mesenchymal Cells from Human Fetal Membranes," J. Tissue Eng. Regen. Med. (2007) 1:296-305.
Stanworth, et al., "Stem Cells: Progress in Research and Edging towards the Clinical Setting," Clin. Med. 1(5):378-382 (2001).
Stromberg et al., "Isolation of Functional Human Trophoblast Cells and Their Partial Characterization in Primary Cell Culture," In Vitro 14(7):631-638 (1978).
Sudo, et al., "Mesenchymal Progenitors Able to Differentiate into Osteogenic, Chondrogenic, and/or Adipogenic Cells in Vitro Are Present in Most Primary Fibroblast-Like Cell Populations," Stem Cells, 25: 1610-1617, Publically available Mar. 29, 2007.
Sunderland et al., "HLA A, B, C Antigens Are Expressed on Nonvillous Trophoblast of the Early Human Placenta," Journal of Immunology 127(6):2614-2615 (1981).
Tarrade et al., "Characterization of Human Villous and Extravillous Trophoblasts Isolated from First Trimester Placenta," Laboratory Investigation 81(9):1199-1211 (2001).
Thomson, et al., Embryonic stem cell lines derived from human blastocysts. Science. 282 (5391): 1145-1147 (1998).
Toma et al., "Human Mesenchymal Stem Cells Differentiate to a Cardiomyocyte Phenotype in the Adult Murine Heart," Circulation 105:93-98 (2002).
Truman et al., "Human Placental Cytotrophoblast Cells: Identification and Culture," Arch Gynecol. Obstet. 246:39-49 (1989).
Truman et al., "The Effects of Substrate and Epidermal Growth Factor on Human Placental Trophoblast Cells in Culture," In Vitro Cellular & Developmental Biology 22(9):525-528 (1986).
Turner, et al., "A modified Harvest Technique for Cord Blood Hematopoietic Stem Cells," Bone Marrow Transplantation 10:89-91 (1992).
Ulloa-Montoya, et al., "Culture Systems for Pluripotent Stem Cells," Journal of Bioscience and Bioengineering, 2005; 100(1):12-27.
Viacord, Umblicical cord blood can save lives (Informational brochure), Boston: ViaCell CENTR-BRO R1 Oct. 2001.
Wang et al., "Enhanced Recovery of Hematopoietic Progenitor and Stem Cells from Cultivated, Postpartum Human Placenta," Blood 98(11/1):183a Abstract No. 769 (2001).
Wang et al., "Mesenchymal Stem/Progenitor Cells in Human Cord Blood as Support for Ex Vivo Expansion of CD34+ Hematopoietic Stem Cells and for Chondrogenic Differentiation," Haematologica 89(7):837-844 (2004).
Wang et al., Biomaterials 24(22):3969-80 (2003).
Watanabe et al, "Multilineage Potential of Human Placenta-Derived Mesenchymal Cells," Blood 100(11):517a, Abstract 2022 (2002).
Wiesmann, et al., "Effects of Caspase Inhibitors on Hematopoietic Engraftment After Short-Term Culture," Cell. Transplant. 11(4):351-358 (2002).
Xu et al., "BMP4 Initiates Human Embryonic Stem Cell Differentiation to Trophoblast," Nature Biology 20:1261-1264 (2002).
Xu et al., "High Sensitivity of Megakaryocytic Progenitor Cells Contained in Placental/Umbilical Cord Blood to the Stresses During Cryopreservation," Bone Marrow Transplantation 34: 537-543 (2004).
Xu et al., "Feeder-free growth of undifferentiated human embryonic stem cells" Nature Biotechnology 19:971-974 (2001).
Ye et al., "Recovery of Placental-Derived Adherent Cells with Mesenchymal Stem Cell Characteristics," Blood 98(11):147b Abstract No. 4260 (2001).
Yeger et al., "Enzymatic Isolation of Human Trophoblast and Culture on Various Substrates: Comparison of First Trimester with Term Trophoblast," Placenta 10:137-151 (1989).
Yen et al, "Isolation of multipotent cells from human term placenta" Stem Cells (Dayton, Ohio) 2005, vol. 23(1):3-9, XP002443187 ISSN: 1065-5099 (Jan. 2005).
Yin et al., "AC133, a novel marker for human hematopoietic stem and progenitor cells" Blood 90(12):5002-5012 (1997).
Young, et al., "Human Pluripotent and Progenitor Cells Display Cell Surface Cluster Differentiation Markers CD10, CD13, CD56, and MHC class-I," Proc Soc Exp Biol Med. 221(1):63-71 (1999).
Young, et al., "Use of Mesenchymal Stem Cells in a Collagen Matrix for Achilles Tendon Repair," 16:4:406-413 (1998).
Yui et al., "Functional, Long-term Cultures of Human Term Trophoblasts Purified by Column-elimination of CD9 Expressing Cells," Placenta 15:231-246 (1994).
Zhang, et al., "Comparison of Mesenchymal Stem Cells from Human Placenta and Bone Marrow," Chinese Medical Journal, 117(6):882-87 (2004).
Zhang, et al., "Efficient Adena-Associated Virus-Mediated Gene Expression in Human Placenta-Derived Mesenchvmal Cells," Microbiol. Immunol. 47(1):109-16 (2003).
Zhang, et al., "Human Placenta-Derived Mesenchymal Progenitor Cells Support Culture Expansion of Long-Term Culture-Initiating Cells from Cord Blood CD34+ Cells." Exp. Hematol. 32(7): 657-664 (2004).
Zhao, et al., "Microscopic Investigation of Erythrocyte Deformation Dynamics," Biorheology 43(6):747-65 (2006).

* cited by examiner

TREATMENT OF SARCOIDOSIS USING PLACENTAL STEM CELLS

This application claims the benefit of U.S. Provisional Patent Application Ser. No. 61/322,272, filed Apr. 8, 2010, which is incorporated by reference herein in its entirety.

1. FIELD

Provided herein are isolated placental cells (e.g., placental stem cells), populations of the placental stem cells, and methods of using the same to treat sarcoidosis or a sarcoidosis-related disease, disorder or condition, for example, systemic sarcoidosis, cutaneous sarcoidosis, Löfgren's syndrome, neurosarcoidosis, pulmonary sarcoidosis, cardiac sarcoidosis, ocular sarcoidosis, or sarcoidosis with the involvement of other organs or tissues.

2. BACKGROUND

Sarcoidosis, also called sarcoid disease or Besnier-Boeck disease, is a multisystem granulomatous inflammatory disease that can affect a variety of organs (e.g., lungs, skin, heart, eyes, liver, nervous system, kidneys, or musculoskeletal system). The etiology of sarcoidosis has remained unknown, though it has been linked to alterations in the immune response after exposure to an environmental, occupational, or infectious agent in genetically susceptible individuals.

Steroid therapy (e.g., corticosteroids such as prednisone) has been the standard treatment for sarcoidosis. However, the use of corticosteroids has a number of drawbacks. For example, certain patients do not respond to steroid therapy. In addition, corticosteroids have several serious side effects, and their use is typically limited to progressive or severe conditions. Accordingly, there exists a need for new methods of treating sarcoidosis, using, for example, human placental stem cells.

3. SUMMARY

In one aspect, provided herein are methods of treating, managing, ameliorating or preventing sarcoidosis, or one or more sarcoidosis-related diseases, disorders and/or conditions, e.g., associated with, resulting in or caused by sarcoidosis. Also provided herein are kits for use in the treatment of sarcoidosis, or a disease, disorder or condition caused by, or relating to, sarcoidosis.

In one embodiment, provided herein is a method of treating an individual having sarcoidosis, or a sarcoidosis-related disease, disorder or condition, comprising administering to the individual a therapeutically effective amount of tissue culture plastic-adherent placental cells, e.g., placental multipotent cells or placental stem cells, also referred to herein as PDACs (placenta derived adherent cells, e.g., the placenta-derived adherent cells described in Section 4.2, below), or culture medium conditioned by PDACs (e.g., placental stem cells), in an amount and for a time sufficient for detectable improvement of one or more symptoms of sarcoidosis, or said disease, disorder or condition.

In another aspect, provided herein is the use of placental cells (e.g., placental stem cells) in the manufacture of a medicament for treating, managing, ameliorating or preventing sarcoidosis or diseases, disorders and/or conditions caused by, or relating to, sarcoidosis.

In another embodiment, provided herein are kits comprising PDACs or a therapeutic cell composition thereof, which can be prepared in a pharmaceutically acceptable form, for example by mixing with a pharmaceutically acceptable carrier, and an applicator, along with instructions for use.

In certain embodiments, the method comprises administering placental cells (e.g., placental stem cells) to said individual in an amount and for a time sufficient for detectable improvement of one or more symptoms of said sarcoidosis or said disease or disorder, as compared to the individual prior to administration of said placental stem cells.

In certain embodiments, said therapeutically effective amount of placental cells reduces, e.g., detectably reduces, the number of, or degree of severity of, or reduces the rate of increase in the number of, or degree of severity, said one or more symptoms in said individual, e.g., and/or detectable improvement, of one or more symptoms of sarcoidosis or sarcoidosis-related diseases, disorders or conditions. In specific embodiments, said therapeutically effective amount of placental cells reduces, e.g., detectably reduces, the number of, or degree of severity of, or reduces the rate of increase in the number of, or degree of severity, one or more granulomas in said individual. In one embodiment, said therapeutically effective amount is an amount that results in a detectable improvement in at least one symptom of said sarcoidosis.

In one specific embodiment, said sarcoidosis is systemic sarcoidosis, and said symptoms comprise one ore more of formation of granulomas, fatigue, weight loss, fever, aches, pains, arthritis, dry eyes, swelling of the knees, blurry vision, shortness of breath, cough or skin lesions.

In another specific embodiment, said sarcoidosis is cutaneous sarcoidosis, and said symptoms comprise a skin lesion. In a more specific embodiment, said cutaneous sarcoidosis comprises one or more of annular sarcoidosis, erythrodermic sarcoidosis, ichthyosiform sarcoidosis, hypopigmented sarcoidosis, morpheaform sarcoidosis, mucosal sarcoidosis, papular sarcoid, scar sarcoid, subcutaneous sarcoidosis or ulcerative sarcoidosis. In a more specific embodiment, said skin lesion comprises one or more of erythema nodosum, nummular eczema, erythema multiforme, calcinosis cutis and pruritus, lupus pernio, skin plaques, maculopapular eruptions, nodular lesions deeper in the skin or infiltration of old scars.

In another specific embodiment, said sarcoidosis is Löfgren's syndrome, and said symptoms comprise one or more of erythema nodosum, bilateral hilar denopathy, arthritis, arthralgias or fever. In another specific embodiment, said sarcoidosis is neurosarcoidosis, and said symptoms comprise one or more of formation of granulomas in the nervous system, headache, confusion, malaise or facial paralysis. In another specific embodiment, said sarcoidosis is pulmonary sarcoidosis, and said symptoms comprise one or more of cough, shortness of breath, chest pain, a feeling of tightness in the chest, hoarseness, nasal obstruction and recurrent or persistent sinusitis. In another specific embodiment, said sarcoidosis is cardiac sarcoidosis, and said symptoms comprise one or more of chest pain, palpitations, congestive heart failure, pericarditis or papillary muscle dysfunction, shortness of breath, ankle swelling, irregular heart beat or sudden death. In another specific embodiment, said sarcoidosis is ocular sarcoidosis, and said symptoms comprise one or more of red or watery eyes, granulomatous uvetis, iris nodules, retinochoroiditis, conjunctivitis, lacrimal gland involvement or proptosis. In another specific embodiment, said sarcoidosis is sarcoidosis with the involvement of other organs or tissues, e.g., sarcoidosis with musculoskeletal, hepatic, hematologic, psychiatric, renal, splenic, nasal sinus, oral, gastric or intestinal, endocrine, pleural or reproductive involvement. In another specific embodiment, said sarcoidosis is sarcoidosis of one or more organs or tissues other than pulmonary tissues or organs. In a more specific embodiment, said sarcoidosis is sarcoidosis of one or more organs or tissues other than the lungs.

In certain embodiments, the method of treatment comprises administering at least about $1\times10^7$, $5\times10^7$, $1\times10^8$, $5\times10^8$, $1\times10^9$, $5\times10^9$, or $1\times10^{10}$ placental cells to said individual. In another specific embodiment, said placental cells have been proliferated in vitro for no more than 2, 3, 4, 5, 6, 7, 8, 9, 10, 11, 12, 13, 14, 15, 16, 17, 18, 19, 20, 21, 22, 23, 24, 25, 26, 27, 28, 29 or 30 population doublings. In another embodiment of any of the embodiments herein, said placental cells have been cryopreserved and thawed prior to said administering.

In certain embodiments of any of the above methods, said placental cells are adherent to tissue culture plastic and are $CD34^-$, $CD10^+$, $CD105^+$ and $CD200^+$ as detected by flow cytometry. In a specific embodiment, the placental cells have the capacity to differentiate into osteogenic or chondrogenic cells. In another embodiment, said placental cells are adherent to tissue culture plastic; $CD34^-$, $CD10^+$, $CD105^+$ and $CD200^+$ as detected by flow cytometry; and have the capacity to differentiate into cells having one or more characteristics of osteogenic or chondrogenic cells, e.g., characteristics of osteocytes or chondrocytes. In other embodiments, the placental cells additionally have the ability to differentiate into cells having one or more characteristics of neural cells or neurogenic cells, e.g., characteristics of neurons; one or more characteristics of glial cells, e.g., characteristics of glia or astrocytes; one or more characteristics of adipocytic cells, e.g., characteristics of adipocytes; one or more characteristics of pancreatic cells; and/or one or more characteristics of cardiac cells.

In another embodiment, said placental cells are $CD34^-$, $CD10^+$, $CD105^+$ and $CD200^+$, and one or more of $CD38^-$, $CD45^-$, $CD80^-$, $CD86^-$, $CD133^-$, HLA-DR,DP,DQ$^-$, SSEA3$^-$, SSEA4$^-$, $CD29^-$, $CD44^+$, $CD73^+$, $CD90^+$, $CD105^+$, HLA-A,B,C$^+$, PDL1$^+$, ABC-p$^+$, and/or OCT-4$^+$, as detected by flow cytometry and/or RT-PCR. In another embodiment, said placental cells are $CD34^-$, $CD45^-$, $CD10^+$, $CD90^+$, $CD105^+$ and $CD200^+$, as detected by flow cytometry. In another embodiment, said placental cells are $CD34^-$, $CD45^-$, $CD10^+$, $CD80^-$, $CD86^-$, $CD90^+$, $CD105^+$ and $CD200^+$, as detected by flow cytometry. In another embodiment, said placental cells are $CD34^-$, $CD45^-$, $CD10^+$, $CD80^-$, $CD86^-$, $CD90^+$, $CD105^+$ and $CD200^+$, and additionally one or more of $CD29^+$, $CD38^-$, $CD44^+$, $CD54^+$, SH3$^-$ or SH4$^+$, as detected by flow cytometry. In another embodiment, said placental cells are $CD34^-$, $CD38^-$, $CD45^-$, $CD10^+$, $CD29^+$, $CD44^+$, $CD54^+$, $CD73^+$, $CD80^-$, $CD86^-$, $CD90^+$, $CD105^-$, and $CD200^+$ as detected by flow cytometry.

In another embodiment, said $CD34^-$, $CD10^+$, $CD105^+$ and $CD200^+$ placental cells are additionally one or more of $CD117^-$, $CD133^-$, KDR$^-$ (VEGFR2$^-$), HLA-A,B,C$^+$, HLA-DP,DQ,DR$^-$, or Programmed Death-1 Ligand (PDL1)$^+$, or any combination thereof. In another specific embodiment, said placental cells are $CD34^-$, $CD38^-$, $CD45^-$, $CD10^+$, $CD29^+$, $CD44^+$, $CD54^+$, $CD73^+$, $CD80^-$, $CD86^-$, $CD90^+$, $CD105^+$, $CD117^-$, $CD133^-$, $CD200^+$, KDR$^-$ (VEGFR2), HLA-A,B,C$^-$, HLA-DP,DQ,DR, or Programmed Death-1 Ligand (PDL1)$^+$, as detected by flow cytometry.

In another embodiment, any of the placental cells described herein are additionally ABC-p$^+$, as detected by flow cytometry, or OCT-4$^+$ (POU5F1$^+$), e.g., as determined by RT-PCR, wherein ABC-p is a placenta-specific ABC transporter protein (also known as breast cancer resistance protein (BCRP) and as mitoxantrone resistance protein (MXR)). In another embodiment, any of the placental cells described herein are additionally SSEA3$^-$ or SSEA4$^-$, e.g., as determined by flow cytometry, wherein SSEA3 is Stage Specific Embryonic Antigen 3, and SSEA4 is Stage Specific Embryonic Antigen 4. In another embodiment, any of the placental cells described herein are additionally SSEA3$^-$ and SSEA4$^-$.

In another embodiment of the methods described herein, any of the placental cells described herein are additionally one or more of MHC-I$^+$ (e.g., HLA-A,B,C$^+$), MHC-II$^-$ (e.g., HLA-DP,DQ,DR$^-$) or HLA-G$^-$. In another embodiment, any of the placental cells described herein are additionally each of MHC-I$^+$ (e.g., HLA-A,B,C$^+$), MHC-II$^-$ (e.g., HLA-DP,DQ, DR$^-$) and HLA-G$^-$, as detected by flow cytometry.

In another embodiment, the $CD34^-$, $CD10^+$, $CD105^+$, $CD200^+$ cells are additionally one or more of $CD29^+$, $CD38^-$, $CD44^+$, $CD54^-$, $CD80^-$, $CD86^-$, SH3$^+$ or SH4$^+$. In another embodiment, the cells are additionally $CD44^+$. In another embodiment, the $CD34^-$, $CD10^+$, $CD105^+$, $CD200^+$ placental cells are additionally one or more of $CD13^+$, $CD29^+$, $CD33^+$, $CD38^-$, $CD44^+$, $CD45^-$, $CD54^+$, $CD62E^-$, $CD62L^-$, $CD62P^-$, SH3$^+$ (CD73$^+$), SH4$^+$ (CD73$^+$), $CD80^-$, $CD86^-$, $CD90^+$, SH2$^+$ (CD105$^+$), CD106/VCAM$^+$, $CD117^-$, CD144/VE-cadherin$^{low}$, CD184/CXCR4$^-$, $CD133^-$, OCT-4$^+$, SSEA3$^-$, SSEA4$^-$, ABC-p$^+$, KDR (VEGFR2$^-$), HLA-A,B,C$^+$, HLA-DP,DQ,DR$^-$, HLA-G$^-$, or Programmed Death-1 Ligand (PDL1)$^+$, or any combination thereof. In another embodiment, the $CD34^-$, $CD10^+$, $CD105^+$, $CD200^+$ placental cells are additionally $CD13^+$, $CD29^+$, $CD33^+$, $CD38^-$, $CD44^+$, $CD45^-$, $CD54$/ICAM$^-$, $CD62E^-$, $CD62L^-$, $CD62P^-$, SH3$^+$ (CD73$^+$), SH4$^-$ (CD73$^+$), $CD80^-$, $CD86^-$, $CD90^+$, SH2$^-$ (CD105$^+$), CD106/VCAM$^+$, $CD117^-$, CD144/VE-cadherin$^{dim}$, CD184/CXCR4$^-$, $CD133^-$, OCT-4$^-$, SSEA3$^-$, SSEA4$^-$, ABC-p$^+$, KDR (VEGFR2$^-$), HLA-A,B,C$^+$, HLA-DP,DQ,DR$^-$, HLA-G$^-$, and Programmed Death-1 Ligand (PDL1)$^+$, as detected by flow cytometry.

In other embodiments of the methods disclosed herein, the isolated placental cells are $CD200^+$ and HLA-G$^-$; $CD73^+$, $CD105^+$, and $CD200^+$; $CD200^-$ and OCT-4$^+$; $CD73^+$, $CD105^+$ and HLA-G$^-$; $CD73^+$ and $CD105^+$; or OCT-4$^+$; or any combination thereof, as detected by flow cytometry.

In certain embodiments of the methods disclosed herein, the isolated placental cells are one or more of $CD10^+$, $CD29^+$, $CD34^-$, $CD38^-$, $CD44^+$, $CD45^-$, $CD54^+$, $CD90^+$, SH2$^+$, SH3$^+$, SH4$^+$, SSEA3$^-$, SSEA4$^-$, OCT-4$^+$, MHC-I$^+$ or ABC-p$^+$, where ABC-p is a placenta-specific ABC transporter protein (also known as breast cancer resistance protein (BCRP) and as mitoxantrone resistance protein (MXR)). In another embodiment, the isolated placental cells are $CD10^-$, $CD29^+$, $CD34^-$, $CD38^-$, $CD44^+$, $CD45^-$, $CD54^+$, $CD90^+$, SH2$^+$, SH3$^+$, SH4$^+$, SSEA3$^-$, SSEA4$^-$, and OCT-4$^+$. In another embodiment, the isolated placental cells are $CD10^+$, $CD29^+$, $CD34^-$, $CD38^-$, $CD45^-$, $CD54^+$, SH2$^+$, SH3$^+$, and SH4$^+$. In another embodiment, the isolated placental cells are $CD10^+$, $CD29^+$, $CD34^-$, $CD38^-$, $CD45^-$, $CD54^+$, SH2$^+$, SH3$^+$, SH4$^+$ and OCT-4$^-$. In another embodiment, the isolated placental cells are $CD10^+$, $CD29^+$, $CD34^-$, $CD38^-$, $CD44^+$, $CD45^-$, $CD54^+$, $CD90^+$, MHC-1$^-$, SH2$^+$, SH3$^+$, SH4$^+$. In another embodiment, the isolated placental cells are OCT-4$^+$ and ABC-p$^+$. In another embodiment, the isolated placental cells are SH2$^+$, SH3$^+$, SH4$^+$ and OCT-4$^+$. In another embodiment, the isolated placental cells are OCT-4$^+$, $CD34^-$, SSEA3$^-$, and SSEA4$^-$. In a specific embodiment, said OCT-4$^+$, $CD34^-$, SSEA3$^-$, and SSEA4$^-$ cells are additionally $CD10^+$, $CD29^+$, $CD34^-$, $CD44^+$, $CD45^-$, $CD54^+$, $CD90^-$, SH2$^+$, SH3$^+$, and SH4$^-$. In another embodiment, the isolated placental cells are OCT-4$^+$ and $CD34^-$, and either SH3$^+$ or SH4$^-$. In another embodiment, the isolated placental cells are $CD34^-$ and either $CD10^+$, $CD29^+$, $CD44^+$, $CD54^+$, $CD90^+$, or OCT-4$^+$. In certain embodiments, the isolated placental cells are CD10+, CD34−, CD105+ and CD200+.

In another embodiment, the isolated placental cells useful in the methods described herein are one or more of CD10+, CD29−, CD44+, CD45−, CD54/ICAM−, CD62-E−, CD62-L−, CD62-P−, CD80−, CD86−, CD103−, CD104−, CD105+, CD106+/VCAM+, CD144/VE-cadherin$^{dim}$, CD184/CXCR4−, β2-microglobulin$^{dim}$, MHC-I$^{dim}$, MHC-II−, HLA-G$^{dim}$, and/or PDL1$^{dim}$. In certain embodiments, such placental cells are at least CD29− and CD54−. In another embodiment, such isolated placental cells are at least CD44+ and CD106+. In another embodiment, such isolated placental cells are at least CD29+.

In certain embodiments of any of the above characteristics, expression of the cellular marker (e.g., cluster of differentiation or immunogenic marker) is determined by flow cytometry. In certain other embodiments, expression of the cellular marker is determined by RT-PCR.

In another embodiment, said placental cells useful in the methods disclosed herein, e.g., said CD10+, CD34−, CD105+, CD200+ cells, express one or more genes at a detectably higher level than an equivalent number of bone marrow-derived mesenchymal stem cells, wherein said one or more genes are one or more of ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, and ZC3H12A, and wherein said bone marrow-derived mesenchymal stem cells have undergone a number of passages in culture equivalent to the number of passages said isolated placental cells have undergone. In certain embodiments, said expression of said one ore more genes is determined, e.g., by RT-PCR or microarray analysis, e.g, using a U133-A microarray (Affymetrix). In another embodiment, said isolated placental cells express said one or more genes when cultured for, e.g., anywhere from about 3 to about 35 population doublings, in a medium comprising 60% DMEM-LG (e.g., from Gibco) and 40% MCDB-201 (e.g., from Sigma); 2% fetal calf serum (e.g., from Hyclone Labs.); 1× insulin-transferrin-selenium (ITS); 1× linoleic acid-bovine serum albumin (LA-BSA); $10^{-9}$ M dexamethasone (e.g., from Sigma); $10^{-4}$ M ascorbic acid 2-phosphate (e.g., from Sigma); epidermal growth factor 10 ng/mL (e.g., from R&D Systems); and platelet-derived growth factor (PDGF-BB) 10 ng/mL (e.g., from R&D Systems). In another embodiment, said isolated placental cells express said one or more genes when cultured for from about 3 to about 35 population doublings in a medium comprising 60% DMEM-LG (e.g., from Gibco) and 40% MCDB-201 (e.g., from Sigma); 2% fetal calf serum (e.g., from Hyclone Labs.); 1× insulin-transferrin-selenium (ITS); 1× linoleic acid-bovine serum albumin (LA-BSA); $10^{-9}$ M dexamethasone (e.g., from Sigma); $10^{-4}$ M ascorbic acid 2-phosphate (Sigma); epidermal growth factor 10 ng/mL (e.g., from R&D Systems); and platelet-derived growth factor (PDGF-BB) 10 ng/mL (e.g., from R&D Systems).

In some embodiments, the placental cells express CD200 and do not express HLA-G, or express CD73, CD 105, and CD200, or express CD200 and OCT-4, or express CD73 and CD105 and do not express HLA-G, or express CD73 and CD105 and facilitate the formation of one or more embryoid-like bodies in a population of placental cells comprising said stem cell when said population is cultured under conditions that allow for the formation of an embryoid-like body, or express OCT-4 and facilitate the formation of one or more embryoid-like bodies in a population of placental cells comprising said stem cell when said population is cultured under conditions that allow for the formation of an embryoid-like body.

In certain embodiments, the placental cells express CD200 and ARTS1 (aminopeptidase regulator of type 1 tumor necrosis factor); ARTS-1 and LRAP (leukocyte-derived arginine aminopeptidase); IL6 (interleukin-6) and TGFB2 (transforming growth factor, beta 2); IL6 and KRT18 (keratin 18); IER3 (immediate early response 3), MEST (mesoderm specific transcript homolog) and TGFB2; CD200 and IER3; CD200 and IL6; CD200 and KRT18; CD200 and LRAP; CD200 and MEST; CD200 and NFE2L3 (nuclear factor (erythroid-derived 2)-like 3); or CD200 and TGFB2 at a detectably higher level than an equivalent number of bone marrow-derived mesenchymal stem cells (BM-MSCs) wherein said bone marrow-derived mesenchymal stem cells have undergone a number of passages in culture equivalent to the number of passages said isolated placental cells have undergone. In other embodiments, the placental cells express ARTS-1, CD200, IL6 and LRAP; ARTS-1, IL6, TGFB2, IER3, KRT18 and MEST; CD200, IER3, IL6, KRT18, LRAP, MEST, NFE2L3, and TGFB2; ARTS-1, CD200, IER3, IL6, KRT18, LRAP, MEST, NFE2L3, and TGFB2; or IER3, MEST and TGFB2 at a detectably higher level than an equivalent number of bone marrow-derived mesenchymal stem cells BM-MSCs, wherein said bone marrow-derived mesenchymal stem cells have undergone a number of passages in culture equivalent to the number of passages said isolated placental cells have undergone.

In various embodiments, said isolated placental cells useful in the methods disclosed herein, e.g., placental stem cells or placental multipotent cells, are contained within a population of cells, at least 10%, 15%, 20%, 25%, 30%, 35%, 40%, 45%, 50%, 55%, 60%, 65%, 70%, 75%, 80%, 85%, 90%, 95%, 98% or 99% of the cells of which are said isolated placental cells. In certain other embodiments, the placental cells in said population of cells are substantially free of cells having a maternal genotype; e.g., at least 40%, 45%, 50%, 55%, 60%, 65%, 70%, 75%, 80%, 85%, 90%, 95%, 98% or 99% of the placental cells in said population have a fetal genotype, i.e., are fetal in origin. In certain other embodiments, the population of cells comprising said placental cells are substantially free of cells having a maternal genotype; e.g., at least 40%, 45%, 50%, 55%, 60%, 65%, 70%, 75%, 80%, 85%, 90%, 95%, 98% or 99% of the cells in said population have a fetal genotype, i.e., are fetal in origin. In certain other embodiments, the population of cells comprising said placental cells comprise cells having a maternal genotype; e.g., at least 10%, 15%, 20%, 25%, 30%, 35%, 40%, 45%, 50%, 55%, 60%, 65%, 70%, 75%, 80%, 85%, 90%, 95%, 98% or 99% of the cells in said population have a maternal genotype, i.e., are maternal in origin.

In an embodiment of any of the embodiments of placental cells (e.g., PDACs) herein, the placental cells facilitate the formation of one or more embryoid-like bodies in a population of placental cells comprising said isolated placental cells when said population is cultured under conditions that allow the formation of an embryoid-like body e.g., culture under proliferation conditions).

In certain embodiments of any of the placental cells disclosed herein, the cells are human.

In certain embodiments, any of the placental cells, e.g., placental stem cells or placental multipotent cells described herein, are autologous to a recipient. In certain other embodiments, any of the placental cells, e.g., placental stem cells or placental multipotent cells described herein, are heterologous to a recipient.

In certain embodiments, the placental cells are cryopreserved prior to said administering. In another embodiment, said isolated placental cells are obtained from a placental cell bank (e.g., a PDAC bank).

In any of the above embodiments of isolated placental cells, the isolated placental cells generally do not differentiate during culturing in growth medium, i.e., medium formulated to promote proliferation, e.g., during proliferation in growth medium. In another embodiment, said isolated placental cells do not require a feeder layer in order to proliferate. In another embodiment, said isolated placental cells do not differentiate in culture solely as the result of culture in the absence of a feeder cell layer.

In certain embodiments, said isolated placental cells are obtained by perfusion of a post-partum placenta that has been drained of blood and perfused to remove residual blood; drained of blood but not perfused to remove residual blood; or neither drained of blood nor perfused to remove residual blood. In another specific embodiment, said isolated placental cells are obtained by physical and/or enzymatic disruption of placental tissue.

Cell surface, molecular and genetic markers of placental cells, useful in the methods provided herein, are described in detail in Section 4.2, below.

In specific embodiments, said individual to whom placental stem cells are administered is additionally administered one or more of a second therapy (e.g., second therapeutic agent), wherein said second therapy (e.g., second therapeutic agent) comprises anti-inflammatory agents, steroids, immune suppressants, antibiotics, TNF-α inhibitors (e.g., infliximab, adalimumab), PDE-4 inhibitors (e.g., apremiliast), IL-12 inhibitors, IL-23 inhibitors, aviptadil, IFN-γ inhibitors, or antimalarials (e.g., chloroquine or hydroxychloroquine).

Examples of anti-inflammatory drugs useful in the treatment of sarcoidosis, or sarcoidosis-related diseases, disorders or conditions include, but are not limited to, mesalamine, 5-ASA (5-aminosalicylic acid) agents (e.g., ASACOL® (mesalamine, delayed-release), DIPENTUM (Osalazine), PENTASA® (mesalamine controlled-release)), sulfasalazine (a combination of 5-ASA and sulfapyridine), anti-inflammatory antibodies (e.g., Infliximab (REMICADE®)), and the like. Examples of steroids useful in the treatment of sarcoidosis, or sarcoidosis-related diseases, disorders or conditions include, but are not limited to, cortisone, hydrocortisone, predisone, methylprednisone, and the like. Typically, as practiced in the art, the dosage of steroid is first delivered in a relatively large dose, followed by smaller dosages as inflammation subsides. Examples of immune suppressants useful in the treatment of sarcoidosis, or sarcoidosis-related diseases or disorders include, but are not limited to, cyclosporine A, 6-mercaptopurine or azathioprine. Any antibiotic can be used in the treatment of Crohn's disease, including, e.g., ampicillin, sulfonamide, cephalosporin, tetracycline, and/or metronidazole. In another specific embodiment, the second therapy is an administration of porcine whipworms, e.g., ova of *Trichuris suis*.

In another embodiment, administration of placental cells (e.g., PDACs), or therapeutic compositions comprising such cells, to an individual in need thereof, can be accomplished, for local or systemic administration, by transplantation, implantation (e.g., of the cells themselves or the cells as part of a matrix-cell combination), injection (e.g., directly to the site of the disease or condition, for example, directly to an granuloma), infusion, delivery via catheter, or any other means known in the art for providing cell therapy. In other embodiment, placental cells (e.g., PDACs), or therapeutic compositions comprising such cells can be delivered to an individual by intravenous, intraarterial, intraperitoneal, intraventricular, intraurethral, intrasternal, intracranial, intramuscular, intrasynovial, intraocular, intravitreal (e.g., where there is an ocular involvement), intracerebral, intracerebroventricular (e.g., where there is a neurologic or brain involvement), intracardiac (e.g., where there is a cardiac involvement), intrathecal, intraosseous infusion, intravesical, and transdermal, intracisternal, epidural, subcutaneous administration.

In specific embodiments, the placental cells are administered locally, e.g., directly into, or adjacent to (e.g., within 1-5 cm of) one or more damaged tissues caused by, or relating to, sarcoidosis. In specific embodiments, the placental cells are administered intralesionally, e.g., directly into, or adjacent to (e.g., within 1-5 cm of) one or more lesions or granulomas caused by, or relating to, sarcoidosis. In certain embodiments, the placental cells are administered in combination with a matrix, e.g., an injectable matrix. In certain other embodiments, placental cells are administered to an individual having a sarcoidosis-related disease or disorder in combination with a solid matrix, e.g., a bone substitute, a matrix or bone substitute described in Section 4.7.4, below.

In another specific embodiment of the methods described above, said isolated placental cells are administered by bolus injection. In another specific embodiment, said isolated placental cells are administered by intravenous infusion. In a specific embodiment, said intravenous infusion is intravenous infusion over about 1 to about 8 hours. In another specific embodiment, said isolated placental cells are administered intracranially. In another specific embodiment, said isolated placental cells are administered intraperitoneally. In another specific embodiment, said isolated placental cells are administered intra-arterially. In another specific embodiment of the method of treatment, said isolated placental cells are administered intramuscularly, intradermally, subcutaneously, or intraocularly.

In another embodiment of the methods described above, said isolated placental cells are administered by surgical implantation into said individual of a composition of matter comprising said isolated placental cells. In a specific embodiment, said composition of matter is a matrix or scaffold. In another specific embodiment, said matrix or scaffold is a hydrogel. In another specific embodiment, said matrix or scaffold is a decellularized tissue. In another specific embodiment, said matrix or scaffold is a synthetic biodegradable composition. In another specific embodiment, said matrix or scaffold is a foam.

In another specific embodiment of the methods described above, said isolated placental cells are administered once to said individual. In another specific embodiment, said isolated placental cells are administered to said individual in two or more separate administrations. In another specific embodiment, said administering comprises administering between about $1 \times 10^4$ and $1 \times 10^5$ isolated placental cells, e.g., placental cells per kilogram of said individual. In another specific embodiment, said administering comprises administering between about $1 \times 10^5$ and $1 \times 10^6$ isolated placental cells per kilogram of said individual. In another specific embodiment, said administering comprises administering between about $1 \times 10^6$ and $1 \times 10^7$ isolated placental cells per kilogram of said individual. In another specific embodiment, said administering comprises administering between about $1 \times 10^7$ and $1 \times 10^8$ isolated placental cells per kilogram of said individual. In other specific embodiments, said administering comprises administering between about $1 \times 10^6$ and about $2 \times 10^6$ isolated placental cells per kilogram of said individual; between about $2 \times 10^6$ and about $3 \times 10^6$ isolated placental cells per kilogram of said individual; between about $3 \times 10^6$ and about $4 \times 10^6$ isolated placental cells per kilogram of said individual; between about $4 \times 10^6$ and about $5 \times 10^6$ isolated placental cells per kilogram of said individual; between about $5 \times 10^6$ and about $6 \times 10^6$ isolated placental cells per kilogram of said individual; between about $6 \times 10^6$ and about $7 \times 10^6$ isolated placental cells per kilogram of said individual; between about $7 \times 10^6$ and about $8 \times 10^6$ isolated placental cells per kilogram of said individual; between about $8 \times 10^6$ and about $9 \times 10^6$ isolated placental cells per kilogram of said individual; or between about $9 \times 10^6$ and about $1 \times 10^7$ isolated placental cells per kilogram of said individual. In another specific embodiment, said administering comprises administering between about $1 \times 10^7$ and about $2 \times 10^7$ isolated placental cells per kilogram of said individual to said individual. In another specific embodiment, said administering comprises administering between about $1.3 \times 10^7$ and about $1.5 \times 10^7$ isolated placental cells per kilogram of said individual to said individual. In another specific embodiment, said administering comprises administering up to about $3 \times 10^7$ isolated placental cells per kilogram of said individual to said individual. In a specific embodiment, said administering comprises administering between about $5 \times 10^6$ and about $2 \times 10^7$ isolated placental cells to said individual. In another specific embodiment, said administering comprises administering about $150 \times 10^6$ isolated placental cells in about 20 milliliters of solution to said individual.

In a specific embodiment, said administering comprises administering between about $5 \times 10^6$ and about $2 \times 10^7$ isolated placental cells to said individual, wherein said cells are contained in a solution comprising 10% dextran, e.g., dextran-40, 5% human serum albumin, and optionally an immunosuppressant.

In another specific embodiment, said administering comprises administering between about $5 \times 10^7$ and $3 \times 10^9$ isolated placental cells intravenously. In specific embodiments, said administering comprises administering about $9 \times 10^8$ isolated placental cells or about $1.8 \times 10^9$ isolated placental cells intravenously. In another specific embodiment, said administering comprises administering between about $5 \times 10^7$ and $1 \times 10^8$ isolated placental cells intralesionally. In another specific embodiment, said administering comprises administering about $9 \times 10^7$ isolated placental cells intralesionally.

3.1 Definitions

As used herein, the term "about," when referring to a stated numeric value, indicates a value within plus or minus 10% of the stated numeric value.

As used herein, the term "SH2" refers to an antibody that binds an epitope on the cellular marker CD105. Thus, cells that are referred to as SH2$^+$ are CD105$^+$.

As used herein, the terms "SH3" and SH4" refer to antibodies that bind epitopes present on the cellular marker CD73. Thus, cells that are referred to as SH3$^+$ and/or SH4$^+$ are CD73$^+$.

A placenta has the genotype of the fetus that develops within it, but is also in close physical contact with maternal tissues during gestation. As such, as used herein, the term "fetal genotype" means the genotype of the fetus, e.g., the genotype of the fetus associated with the placenta from which particular isolated placental cells, as described herein, are obtained, as opposed to the genotype of the mother that carried the fetus. As used herein, the term "maternal genotype" means the genotype of the mother that carried the fetus, e.g., the fetus associated with the placenta from which particular isolated placental cells, as described herein, are obtained.

As used herein, the term "granuloma" refers to a ball-like collection of immune cells formed as a result of inflammatory reaction, for instance, when the immune system attempts to eliminate substances (e.g., infectious organisms such as bacteria and fungi as well as other materials such as keratin, suture fragments and vegetable particles) that it perceives as foreign but is unable to eliminate.

As used herein, the term "isolated cell," e.g., "isolated placental cell," "isolated placental stem cell," and the like, means a cell that is substantially separated from other, different cells of the tissue, e.g., placenta, from which the stem cell is derived. A cell is "isolated" if at least 50%, 60%, 70%, 80%, 90%, 95%, or at least 99% of the cells, e.g., non-stem cells, with which the stem cell is naturally associated, or stem cells displaying a different marker profile, are removed from the stem cell, e.g., during collection and/or culture of the stem cell.

As used herein, "multipotent," when referring to a cell, means that the cell has the ability to differentiate into some, but not necessarily all, types of cells of the body, or into cells having characteristics of some, but not all, types of cells of the body, or into cells of one or more of the three germ layers. In certain embodiments, for example, an isolated placental cell (PDAC), as described in Section 4.2, below, that has the capacity to differentiate into a cell having characteristics of neurogenic, chondrogenic and/or osteogenic cells is a multipotent cell.

As used herein, the term "population of isolated cells" means a population of cells that is substantially separated from other cells of a tissue, e.g., placenta, from which the population of cells is derived.

As used herein, the term "placental cell" refers to a stem cell or progenitor cell that is isolated from a mammalian placenta, e.g., as described in Section 4.2, below, or cultured from cells isolated from a mammalian placenta, also referred to herein as "PDACs," either as a primary isolated or a cultured cell, regardless of the number of passages after a primary culture. In certain embodiments, the term "placental cells" as used herein does not, however, refer to, and the placental cells used in the methods provided herein are not, however, trophoblasts, cytotrophoblasts, syncitiotrophoblasts, angioblasts, hemangioblasts, embryonic germ cells, embryonic stem cells, cells obtained from an inner cell mass of a blastocyst, or cells obtained from a gonadal ridge of a late embryo, e.g., an embryonic germ cell. A cell is considered a "stem cell" if the cell displays attributes of a stem cell, e.g., a marker or gene expression profile associated with one or more types of stem cells; the ability to replicate at least 10-40 times in culture, and the ability to differentiate into cells displaying characteristics of differentiated cells of one or more of the three germ layers. Unless otherwise noted herein, the term "placental" includes the umbilical cord. The isolated placental cells disclosed herein, in certain embodiments, differentiate in vitro under differentiating conditions, differentiate in vivo, or both.

As used herein, a placental cell is "positive" for a particular marker when that marker is detectable above background. Detection of a particular marker can, for example, be accomplished either by use of antibodies, or by oligonucleotide probes or primers based on the sequence of the gene or mRNA encoding the marker. For example, a placental cell is positive for, e.g., CD73 because CD73 is detectable on placental cells in an amount detectably greater than background (in comparison to, e.g., an isotype control). A cell is also positive for a marker when that marker can be used to distinguish the cell from at least one other cell type, or can be used to select or isolate the cell when present or expressed by the cell. In the context of, e.g., antibody-mediated detection, "positive," as an indication a particular cell surface marker is present, means that the marker is detectable using an antibody, e.g., a fluorescently-labeled antibody, specific for that marker; "positive" also refers to a cell exhibiting the marker in an amount that produces a signal, e.g., in a cytometer, that is detectably above background. For example, a cell is "CD200$^+$" where the cell is detectably labeled with an antibody specific to CD200, and the signal from the antibody is detectably higher than that of a control (e.g., background or an isotype control). Conversely, "negative" in the same context means that the cell surface marker is not detectable using an antibody specific for that marker compared a control (e.g., background or an isotype control). For example, a cell is "CD34$^-$" where the cell is not reproducibly detectably labeled with an antibody specific to CD34 to a greater degree than a control (e.g., background or an isotype control). Markers not detected, or not detectable, using antibodies are determined to be positive or negative in a similar manner, using an appropriate control. For example, a cell or population of cells can be determined to be OCT-4$^+$ if the amount of OCT-4 RNA detected in RNA from the cell or population of cells is detectably greater than background as determined, e.g., by a method of detecting RNA such as RT-PCR, slot blots, etc. Unless otherwise noted herein, cluster of differentiation ("CD") markers are detected using antibodies. In certain embodiments, OCT-4 is determined to be present, and a cell is "OCT-4$^+$" if OCT-4 is detectable using RT-PCR.

As used herein, the designation "low," when referring to the expression of a marker detectable in flow cytometry, means that the marker is expressed by fewer than 10% of cells tested, or that fluorescence attributable to the marker in, e.g., flow cytometry, is less than 1 log above background.

As used herein, "treat" encompasses the remediation of, improvement of, lessening of the severity of, or reduction in the time course of, a disease, disorder or condition (e.g,. sarcpodpsos), or any parameter or symptom thereof.

4. DETAILED DESCRIPTION

4.1 Treatment of Sarcoidosis or Diseases, Disorders or Conditions Caused by, or Relating to, Sarcoidosis Provided herein are methods of treating sarcoidosis or diseases or disorders caused by, or relating to, sarcoidosis comprising administering an effective amount of tissue culture plastic-adherent placental stem cells, e.g., PDACs, as described in Section 4.2, below. Methods for the treatment of such individuals, and for the administration of such stem cells, alone or in combination with other therapies, are discussed in detail below.

4.1.1 Sarcoidosis

Sarcoidosis is a multisystem granulomatous inflammatory disease. The disease is typically characterized by the formation of small, granular inflammatory lesions or granulomas (e.g., non-caseating granulomas) in a variety of organs, and/or the presence of immune responses (e.g., presence of CD4$^+$ T lymphocytes and macrophages) in affected tissues or organs. Granulomatous inflammation may be attributed to the accumulation of monocytes, macrophages, a pronounced Th1 response and activated T-lymphocytes, with elevated production of TNF-α, IL-2, IL-12, IFN-γ, IL-1, IL-6 or IL-15.

Sarcoidosis can be systemic (e.g., systemic sarcoidosis) or local (e.g., localized sarcoid-like reactions). Granulomas can appear in almost any organ, and most often appear in the lungs or the lymph nodes. Other common sites include the liver, spleen, skin and eyes. The involvement of a specific organ may be mild or severe, self-limited or chronic, and limited or wide-ranging in extent. Symptoms usually appear gradually but can occasionally appear suddenly. The common symptoms experienced by sarcoidosis patients comprise fatigue, shortness of breath, cough that will not go away, skin lesions or skin rashes on face, arms, or shins, inflammation of the eyes, weight loss, night sweats, dyspnea, cough, chest discomfort, crackles. malaise, weakness, anorexia, weight loss, or fever. Other symptoms include, for example, enlarged lymph glands (armpit lump), enlarged liver, enlarged spleen, dry mouth or nosebleed. Symptoms of different types of sarcoidosis are described below.

The clinical course generally varies. In some embodiments, sarcoidosis can be asymptomatic. In other embodiments, a tissue or organ can remained inflamed or become scarred or fibrotic if one or more granulomas in the tissue or organ do not heal. In still other embodiments, sarcoidosis can result in a debilitating chronic condition that may lead to death (e.g., irreversible pulmonary fibrosis).

Thus, in one aspect, the PDACs, populations of such cells, and populations of cells comprising PDACs, provided herein can be used to treat individuals exhibiting sarcoidosis, or one or more diseases, disorders or conditions caused by, or relating to, sarcoidosis. In a specific embodiment, provided herein is a method of treating an individual having sarcoidosis, comprising administering to the individual isolated placental cells, a population of isolated placental cells, or a population of cells comprising isolated placental cells, wherein said administration results in the detectable reduction of progression, detectable lessening of worsening, and/or detectable improvement, of one or more symptoms of said sarcoidosis. In a specific embodiment, said therapeutically effective amount of placental cells reduces, e.g., detectably reduces, the number of, or degree of severity of, or reduces the rate of increase in the number of, or degree of severity, one or more granulomas in said individual. In another specific embodiment, said therapeutically effective amount of placental cells reduces, e.g., detectably reduces, the number of, or reduces the rate of increase in the number of, monocytes, macrophages, or activated T-lymphocytes. In another specific embodiment, said therapeutically effective amount of placental cells reduces, e.g., detectably reduces, the level of, or reduces the rate of increase in the level of, one or more TNF-α, IL-2, IL-12, IFN-γ, IL-1, IL-6, IL-15, or Th1 response in said individual.

In certain embodiments, said sarcoidosis is one or more of systemic sarcoidosis, cutaneous sarcoidosis, Löfgren's syndrome, neurosarcoidosis, pulmonary sarcoidosis, cardiac sarcoidosis, ocular sarcoidosis, hepatic sarcoidosis, musculoskeletal sarcoidosis, renal sarcoidosis, or sarcoidosis with the involvement of other organs or tissues.

Systemic sarcoidosis—is sarcoidosis with multiple organ involvement. In one embodiment, provided herein is a method of treating an individual having systemic sarcoidosis, comprising administering to the individual isolated placental cells, a population of isolated placental cells, or a population of cells comprising isolated placental cells, wherein said administration results in the detectable reduction of progression, detectable lessening of worsening, and/or detectable improvement, of one or more symptoms of said systemic sarcoidosis. In some embodiments, said one or more symptoms of systemic sarcoidosis comprise non-specific general symptoms such as weight loss, fatigue, loss of appetite, fever, chills, night sweats, formation of granulomas, fatigue, aches, pains or arthritis.

In other embodiments, systemic sarcoidosis can present with specific symptoms related to a particular organ affected (e.g., dry eyes, swelling of the knees, blurry vision, shortness of breath, cough, skin lesions such as rashes etc.). In specific embodiments, said specific symptom is one or more of a pulmonary, pulmonary lymphatic, musculoskeletal, hepatic, joint, hematologic, dermatologic, ocular, psychiatric, neurological, renal, splenic, neurologic, nasal sinus, cardiac, bone, oral, gastric, intestinal, endocrine, pleural or reproductive symptom.

Cutaneous sarcoidosis—is a complication of sarcoidosis with skin involvement. In another embodiment, provided herein is a method of treating an individual having cutaneous sarcoidosis, comprising administering to the individual isolated placental cells, a population of isolated placental cells, or a population of cells comprising isolated placental cells, wherein said administration results in the detectable reduction of progression, detectable lessening of worsening, and/or detectable improvement, of one or more symptoms of said cutaneous sarcoidosis. In certain embodiments, the cutaneous sarcoidosis comprises annular sarcoidosis, erythrodermic sarcoidosis, ichthyosiform sarcoidosis, hypopigmented sarcoidosis, morpheaform sarcoidosis, mucosal sarcoidosis, papular sarcoid, scar sarcoid, subcutaneous sarcoidosis and ulcerative sarcoidosis. In some embodiments, the one or more symptoms of cutaneous sarcoidosis comprise a variety of skin lesions or conditions, either specific or non-specific (e.g., similar to several other skin conditions). Exemplary skin lesions or conditions associated with cutaneous sarcoidosis comprise papules (e.g., granulomatous rosacea, acne or benign appendageal tumors), skin plaques (e.g., psoriasis, lichen planus, nummular eczema, discoid lupus erythematosus, granuloma annulare, cutaneous T-cell lymphoma, Kaposi's sarcoma or secondary syphilis), lupus pernio (e.g., scar or discoid lupus erythematosus), erythema nodosum (e.g., raised, red, firm skin sores, cellulitis, furunculosis or other inflammatory panniculitis), maculopapular eruptions, nodular lesions deeper in the skin or infiltration of old scars. Other skin symptoms include, for example, skin rashes, old scars become more raised, skin lesions or hair loss.

Löfgren's syndrome—represents an acute presentation of systemic sarcoidosis, which is typically characterized by the triad of erythema nodosum, bilateral hilar denopathy and arthritis or arthralgias. It may also be accompanied by fever. In another embodiment, provided herein is a method of treating an individual having Löfgren's syndrome, comprising administering to the individual isolated placental cells, a population of isolated placental cells, or a population of cells comprising isolated placental cells, wherein said administration results in the detectable reduction of progression, detectable lessening of worsening, and/or detectable improvement, of one or more symptoms of said Löfgren's syndrome. In specific embodiments, the one or more symptoms comprise erythema nodosum, bilateral hilar denopathy, arthritis, arthralgias or fever.

Neurosarcoidosis or neurosarcoid—refers to sarcoidosis in which inflammation and abnormal deposits occur in the brain, spinal cord, and any other areas of the nervous system. In another embodiment, provided herein is a method of treating an individual having neurosarcoidosis, comprising administering to the individual isolated placental cells, a population of isolated placental cells, or a population of cells comprising isolated placental cells, wherein said administration results in the detectable reduction of progression, detectable lessening of worsening, and/or detectable improvement, of one or more symptoms of said neurosarcoidosis. Neurosarcoidosis may affect any part of the nervous system, for instance, nerves to the muscles of the face (cranial nerve VII), which may lead to symptoms of facial weakness (e.g., facial palsy), nerves in the eye or nerves that control taste, smell, or hearing.

In some embodiments, the symptoms of neurosarcoidosis comprise changes in menstrual periods, excessive tiredness (e.g., fatigue), headache, visual changes, retinopathy, radicular pain, loss of bowel or bladder control, carpal tunnel syndrome, and/or paraplegia, excessive thirst or high urine output. In other embodiments, the symptoms of neurosarcoidosis comprise confusion, disorientation, decreased hearing, dementia or delirium, dizziness or vertigo (e.g., abnormal sensation of movement), double vision or other vision problems, facial palsy (weakness, drooping), headache, loss of sense of smell or taste, abnormal tastes, psychiatric disturbances, seizures or speech impairment, muscle weakness or sensory losses, or in some occasions, hypopituiarism. In specific embodiments, the symptoms of neurosarcoidosis comprise formation of granulomas in the nervous system (e.g., brain, spinal cord, or facial and optic nerves), headache, confusion, malaise or facial paralysis.

Pulmonary sarcoidosis—refers to sarcoidosis that affects pulmonary tissues or organs (e.g., lungs). In another embodiment, provided herein is a method of treating an individual having pulmonary sarcoidosis, comprising administering to the individual isolated placental cells, a population of isolated placental cells, or a population of cells comprising isolated placental cells, wherein said administration results in the detectable reduction of progression, detectable lessening of worsening, and/or detectable improvement, of one or more symptoms of said pulmonary sarcoidosis. The symptoms of pulmonary sarcoidosis usually involve lung and/or chest symptoms, which can be determined by, for examples, lung gallium (Ga.) scan, chest X-ray, pulmonary function tests, exercise pulse oximetry, CT scan of chest, PET scan, CT-guided biopsy, mediastinoscopy, open lung biopsy or bronchoscopy with biopsy.

In certain embodiments, the symptoms of pulmonary sarcoidosis comprise granulomas in alveolar septa, bronchiolar, and bronchial walls, shortness of breath, cough, loss of lung volume and abnormal lung stiffness, abnormal or deteriorating lung function, decrease in lung volume, decreased compliance, scarring of lung tissue, or bleeding from the lung tissue. Other symptoms include, for example, limited amount of air drawn into the lungs, higher than normal expiratory flow ratios, decreased vital capacity (full breath in, to full breath out), increased $FEV_1/FVC$ ratio, obstructive lung changes, which can cause a decrease in the amount of air that can be exhaled, or enlarged lymph nodes in the chest, which can compress airways or when internal inflammation or nodules impede airflow, pulmonary hypertension, or pulmonary failure.

Without being bound by any theory, the Scadding criteria are the measures most commonly used for disease staging of patients who have pulmonary sarcoidosis. Birefly, the radiographic evidence for each stage can be described as follows: Stage I: bilateral hilar and/or mediastinal lymphadenopathy (enlarged lymph nodes); Stage II: bilateral hilar and/or mediastinal lymphadenopathy; evidence of pulmonary infiltrates; Stage III: alterations in the parenchymal tissue; no lymph node enlargement; and Stage IV: Evidence of pulmonary fibrosis. Thus, provided herein is a method of treating an individual having pulmonary sarcoidosis or disease, disorder or condition caused by, or relating to pulmonary sarcoidosis, comprising administering to the individual isolated placental cells, a population of isolated placental cells, or a population of cells comprising isolated placental cells, wherein said administration results in the detectable reduction of progression, detectable lessening of worsening, and/or detectable improvement, of one or more symptoms of said pulmonary sarcoidosis as determined by the Scadding criteria.

In some embodiments, pulmonary sarcoidosis can develop into pulmonary fibrosis (e.g., irreversible pulmonary fibrosis), which can distort the structure of the lungs and impair breathing or bronchiectasis, a lung disease characterized by destruction and widening of the large airways. Thus, in a specific embodiment, said disease or disorder is pulmonary fibrosis or bronchietasis. In a more specific embodiment, provided herein is a method of treating an individual having pulmonary fibrosis (e.g., irreversible pulmonary fibrosis) caused by, or relating to sarcoidosis, comprising administering to the individual isolated placental cells, a population of isolated placental cells, or a population of cells comprising isolated placental cells, wherein said administration results in the detectable reduction of progression, detectable lessening of worsening, and/or detectable improvement, of one or more symptoms of said pulmonary fibrosis (e.g., irreversible pulmonary fibrosis). In another specific embodiment, provided herein is a method of treating an individual having bronchiectasis caused by, or relating to sarcoidosis, comprising administering to the individual isolated placental cells, a population of isolated placental cells, or a population of cells comprising isolated placental cells, wherein said administration results in the detectable reduction of progression, detectable lessening of worsening, and/or detectable improvement, of one or more symptoms of said bronchiectasis.

In other embodiments, sarcoidosis can involve pulmonary lymphatic system such as hilar or mediastinal involvement, as determined by chest x-ray, and present with symptoms of nontender peripheral or cervical lymphadenopathy.

Cardiac sarcoidosis—refers to sarcoidosis with myocardial involvement. In another embodiment, provided herein is a method of treating an individual having cardiac sarcoidosis, comprising administering to the individual isolated placental cells, a population of isolated placental cells, or a population of cells comprising isolated placental cells, wherein said administration results in the detectable reduction of progression, detectable lessening of worsening, and/or detectable improvement, of one or more symptoms of said cardiac sarcoidosis.

In some embodiments, the one or more symptoms of cardiac sarcoidosis are similar to the symptoms of a disease or disorder of the circulatory system, for example, myocardial infarction, cardiomyopathy, aneurysm, angina, aortic stenosis, aortitis, arrhythmias, arteriosclerosis, arteritis, asymmetric septal hypertrophy (ASH), atherosclerosis, atrial fibrillation and flutter, bacterial endocarditis, Barlow's Syndrome (mitral valve prolapse), bradycardia, Buerger's Disease (thromboangiitis obliterans), cardiomegaly, carditis, carotid artery disease, coarctation of the aorta, congenital heart defects, congestive heart failure, coronary artery disease, Eisenmenger's Syndrome, embolism, endocarditis, erythromelalgia, fibrillation, fibromuscular dysplasia, heart block, heart murmur, hypertension, hypotension, idiopathic infantile arterial calcification, Kawasaki Disease (mucocutaneous lymph node syndrome, mucocutaneous lymph node disease, infantile polyarteritis), metabolic syndrome, microvascular angina, myocarditis, paroxysmal atrial tachycardia (PAT), periarteritis nodosa (polyarteritis, polyarteritis nodosa), pericarditis, peripheral vascular disease, critical limb ischemia, phlebitis, pulmonary valve stenosis (pulmonic stenosis), Raynaud's Disease, renal artery stenosis, renovascular hypertension, rheumatic heart disease, diabetic vasculopathy, septal defects, silent ischemia, syndrome X, tachycardia, Takayasu's Arteritis, Tetralogy of Fallot, transposition of the great vessels, tricuspid atresia, truncus arteriosus, valvular heart disease, varicose ulcers, varicose veins, vasculitis, ventricular septal defect, Wolff-Parkinson-White Syndrome, endocardial cushion defect, acute rheumatic fever, acute rheumatic pericarditis, acute rheumatic endocarditis, acute rheumatic myocarditis, chronic rheumatic heart diseases, diseases of the mitral valve, mitral stenosis, rheumatic mitral insufficiency, diseases of aortic valve, diseases of other endocardial structures, ischemic heart disease (acute and subacute), angina pectoris, acute pulmonary heart disease, pulmonary embolism, chronic pulmonary heart disease, kyphoscoliotic heart disease, myocarditis, endocarditis, endomyocardial fibrosis, endocardial fibroelastosis, atrioventricular block, cardiac dysrhythmias, myocardial degeneration, cerebrovascular disease, a disease of arteries, arterioles and capillaries, or a disease of veins and lymphatic vessels. Thus, in certain embodiments, improvement in an individual having sarcoidosis or a sarcoidosis-related disease or disorder, wherein the individual is administered the PDACs or therapeutic compositions provided herein, can be assessed or demonstrated by detectable improvement in one or more symptoms of said sarcoidosis or said sarcoidosis-related disease or disorder.

In certain embodiments, the method of comprises administering placental cells to said individual in an amount and for a time sufficient for detectable improvement of one or more indicia of cardiac function, wherein said indicia of cardiac function are chest cardiac output (CO), cardiac index (CI), pulmonary artery wedge pressure (PAWP), cardiac index (CI), % fractional shortening (% FS), ejection fraction (EF), left ventricular ejection fraction (LVEF); left ventricular end diastolic diameter (LVEDD), left ventricular end systolic diameter (LVESD), contractility (dP/dt), a decrease in atrial or ventricular functioning, an increase in pumping efficiency, a decrease in the rate of loss of pumping efficiency, a decrease in loss of hemodynamic functioning, or decrease in complications associated with cardiomyopathy, as compared to the individual prior to administration of said PDACs.

In specific embodiments of the methods of treatment provided herein, the PDACs are administered with stem cells (that is, stem cells that are not PDACs), myoblasts, myocytes, cardiomyoblasts, cardiomyocytes, or progenitors of myoblasts, myocytes, cardiomyoblasts, and/or cardiomyocytes.

In a specific embodiment, the methods of treatment provided herein comprise administering PDACs, e.g., a therapeutic composition comprising the cells, to a patient with sarcoidosis or a disease, disorder or condition caused by, or relating to, sarcoidosis; and evaluating the patient for improvements in cardiac function, wherein the therapeutic cell composition is administered as a matrix-cell complex. In certain embodiments, the matrix is a scaffold, preferably bioabsorbable, comprising at least the cells.

To this end, further provided herein are populations of PDACs contacted with, e.g., incubated or cultured in the presence of, one or more factors that stimulate stem or progenitor cell differentiation along a cardiogenic, angiogenic, hemangiogenic, or vasculogenic pathway. Such factors include, but are not limited to factors, such as growth factors, chemokines, cytokines, cellular products, demethylating agents, and other factors which are now known or later determined to stimulate differentiation, for example of stem cells, along cardiogenic, angiogenic, hemangiogenic, or vasculogenic pathways or lineages.

In certain embodiments, PDACs may be differentiated along cardiogenic, angiogenic, hemangiogenic, or vasculogenic pathways or lineages in vitro by culture of the cells in the presence of factors comprising at least one of a demethylation agent, a BMP (bone morphogenetic protein), FGF (fibroblast growth factor), Wnt factor protein, Hedgehog protein, and/or an anti-Wnt factor.

PDACs, and populations of such cells, can be provided therapeutically or prophylactically to an individual, e.g., an individual having a disease, disorder or condition of, or affecting, the heart or circulatory system relating to sarcoidosis. Such diseases, disorders or conditions can include congestive heart failure due to atherosclerosis, cardiomyopathy, or cardiac injury, e.g., an ischemic injury, such as from myocardial infarction or wound (acute or chronic).

Ocular Sarcoidosis—is sarcoidosis that affects the eye. In another embodiment, provided herein is a method of treating an individual having ocular sarcoidosis, comprising administering to the individual isolated placental cells, a population of isolated placental cells, or a population of cells comprising isolated placental cells, wherein said administration results in the detectable reduction of progression, detectable lessening of worsening, and/or detectable improvement, of one or more symptoms of said ocular sarcoidosis. In certain embodiments, the one or more symptoms of ocular sarcoidosis comprise uveitis (e.g., granulomatous uvetis), uveoparotitis, retinal inflammation, loss of visual acuity, blindness red, watery eyes, iris nodules, retinochoroiditis, conjunctivitis, lacrimal gland involvement or proptosis.

Sarcoidosis with Musculoskeletal, Hepatic, Hematologic, Psychiatric, Renal, Splenic, Nasal Sinus, Oral, Gastric or Intestinal, Endocrine, Pleural or Reproductive Involvement In certain embodiments, sarcoidosis can involve muscle, hepatic, joint, hematologic, psychiatric, renal, splenic, nasal sinus, bone, oral gastric or intestinal, endocrine, pleural or reproductive system and present with respective symptoms. In another embodiment, provided herein is a method of treating an individual having sarcoidosis with musculoskeletal, hepatic, joint, hematologic, psychiatric, renal, splenic, nasal sinus, oral gastric or intestinal, endocrine, pleural or reproductive involvement, comprising administering to the individual isolated placental cells, a population of isolated placental cells, or a population of cells comprising isolated placental cells, wherein said administration results in the detectable reduction of progression, detectable lessening of worsening, and/or detectable improvement, of one or more symptoms of said sarcoidosis.

In one embodiment, sarcoidosis with musculoskeletal involvement can be asymptomatic with or without enzyme elevations, or present with symptoms of, for example, insidious or acute myopathy with muscle weakness, arthritis (e g , ankle, knee, wrist, and elbow arthritis), chronic arthritis with Jaccoud's deformities or dactylitis, periarthritis, arthralgia, osteolytic or cystic lesions, osteopenia or Löfgren's syndrome. In another embodiment, sarcoidosis with hepatic involvement can be ayrmptomatic, or present with one or more symptoms such as mild elevations in liver function test results, hypolucent lesions on CT scans with radiopaque dye, hepatomegaly, changes in the liver enzyme levels, liver diseases, fever, malaise, fatigue, cholestasis, cirrhosis, or with symptoms similar to granulomatous hepatitis.

In another embodiment, patients with hematologic sarcoidosis have one or more symptoms of lymphopenia, anemia of chronic disease, anemia due to granulomatous infiltration of bone marrow, pancytopenia, splenic sequestration, thrombocytopenia or leucopenia. In another embodiment, patients with sarcoidosis can exhibit psychiatric symptoms (e.g., depression). In another embodiment, sarcoidosis with renal involvement can present with symptoms of asymptomatic hypercalciuria, interstitial nephritis, chronic renal failure caused by nephrolithiasis, or nephrocalcinosis. In another embodiment, sarcoidosis with splenic involvement can be asymptomatic, or present with symptoms of pain, thrombocytopenia or as determined by x-ray or CT scan. In another embodiment, sarcoidosis with nasal sinus involvement can present with symptoms of sinus mucosa with symptoms similar to common allergic and infectious sinusitis, or upus pernio. In another embodiment, sarcoidosis with oral involvement can present with symptoms of asymptomatic parotid swelling, parotitis with xerostomia, Heerfordt's syndrome, uveitis, bilateral parotid swelling, facial palsy, chronic fever, oral lupus pernio, or disfigured hard palate, cheek, tongue, and gums. In another embodiment, symptoms of sarcoidosis with gastric or intestinal, endocrine, pleural or reproductive involvement comprise gastric granulomas, mesenteric lymphadenopathy, abdominal pain, panhypopituitarism, thyroid infiltration, secondary hypoparathyroidism, hypercalcemia, or lymphocytic exudative effusions.

In another embodiment, provided herein is a method of treating an individual having sarcoidosis with the involvement of one or more tissues or organs other than pulmonary tissues or organs, comprising administering to the individual isolated placental cells, a population of isolated placental cells, or a population of cells comprising isolated placental cells, wherein said administration results in the detectable reduction of progression, detectable lessening of worsening, and/or detectable improvement, of one or more symptoms of said sarcoidosis. In another embodiment, provided herein is a method of treating an individual having sarcoidosis with the involvement of one or more tissues or organs other than the lungs, comprising administering to the individual isolated placental cells, a population of isolated placental cells, or a population of cells comprising isolated placental cells, wherein said administration results in the detectable reduction of progression, detectable lessening of worsening, and/or detectable improvement, of one or more symptoms of said sarcoidosis.

Other Diseases, Disorders or Conditions

In some embodiments, said sarcoidosis-related disease or disorder is a cancer (e.g., a cancer in an organ known to be affected in sarcoidosis). In another embodiment, provided herein is a method of treating an individual having sarcoidosis-related cancer, comprising administering to the individual isolated placental cells, a population of isolated placental cells, or a population of cells comprising isolated placental cells, wherein said administration results in the detectable reduction of progression, detectable lessening of worsening, and/or detectable improvement, of one or more symptoms of said sarcoidosis-related cancer.

Without being bound by any theory, patients with sarcoidosis can have an increased risk for cancers (e.g., lung cancer or malignant lymphonas). In certain embodiment, said cancer is a solid tumor. In some embodiments, said cancer is primary ductal carcinoma, leukemia, acute T cell leukemia, chronic myeloid lymphoma (CML), acute myelogenous leukemia, chronic myelogenous leukemia (CML), lung carcinoma, colon adenocarcinoma, histiocytic lymphoma, colorectal carcinoma, colorectal adenocarcinoma, or retinoblastoma. In a specific embodiments, the cancer is hairy cell leukemia, acute myeloid leukemia (acute myelogenous leukemia) or acute myeloblastic leukemia.

In other embodiments, said sarcoidosis-related disease or disorder comprises vitamin D dysregulation, hyperprolactinemia, thyroid diseases (e.g., hypothyroidism, hyperthyroidism and thyroid autoimmunity), autoimmune disorders or sarcoidosis-lymphoma syndrome and hypersensitivity (e.g., celiac disease, type IV hypersensitivity).

Typically, an individual presenting with one or more symptoms of sarcoidosis is assessed for sarcoidosis at least once before a final diagnosis of sarcoidosis, e.g., as a part of tests performed to arrive at a diagnosis of sarcoidosis. Also, typically, an individual diagnosed with sarcoidosis is assessed at least once, usually more than once, after a diagnosis of sarcoidosis, for symptoms of sarcoidosis to gauge progress of the disease. Such an assessment may comprise diagnosis of pulmonary functions or symptoms, e.g., chest imaging, chest X-ray, CT scan of chest, PET scan, CT-guided biopsy, mediastinoscopy, open lung biopsy, bronchoscopy with biopsy, endobronchial ultrasound or endoscopic ultrasound with FNA of mediastinal lymph nodes; tissue biopsy, e.g., tissue biopsy, angiotensin-converting enzyme blood; magnetic resonance imaging (MRI), e.g., to detect cardiac, neurological, or liver involvement, computerized tomography (CT) scanning, positron emission tomography (PET) scanning, electrocardiogram of affected tissues or organs; liver function tests; ocular examination; blood, ionize and urine calcium determination; serum phophorus determination; thyroid function tests; slit eye lamp exam to detec uveitis; or exclusion of other granulomatous disorders. Effectiveness of treatment of sarcoidosis, e.g., effectiveness of administering placental cells, can be assessed by any one, or more, of such symptoms of sarcoidosis. Effectiveness can also be assessed by monitoring the reduction of progression, detectable lessening of worsening, and/or detectable improvement of symptoms or functions of affected organs in said individual, before and after administration of said placental cells.

In one aspect, provided herein are methods for treating a patient with sarcoidosis or a sarcoidosis-related disease, disorder or condition comprising administering a therapeutic cell composition to a patient with sarcoidosis or a sarcoidosis-related disease, disorder or condition, and evaluating the patient for improvements in the symptoms of sarcoidosis, wherein said cell composition comprises PDACs as described herein.

In one embodiment, said methods can comprise determining, once or a plurality of times before said administering, and/or once or a plurality of times after said administering, one or more of (1) a number and/or degree of affected organs in said individual; (2) a number and/or degree of symptoms in said individual, (3) a number and/or degree of granulomas; or (4) the degree of inflammation in said individual.

In certain embodiments, said therapeutically effective amount of placental cells reduces, e.g., detectably reduces, the number of, or degree of severity of, or reduces the rate of increase in the number of, or degree of severity, said one or more symptoms in said individuals, and/or results in detectable improvement, of one or more symptoms of sarcoidosis or sarcoidosis-related diseases, disorders or conditions.

In one embodiment, said therapeutically effective amount is an amount that results in a detectable improvement in at least one symptom of said sarcoidosis or a sarcoidosis-related disease or disorder. In another embodiment, said therapeutically effective amount is an amount that results in modulation, e.g., suppression, of the activity, e.g., proliferation, of an immune cell, or plurality of immune cells. In a specific embodiment, said therapeutically effective amount is an amount that results in suppression of an inflammatory response, as determined by one or more inflammatory markers (e.g., C-reactive protein, IL-6, or as determined by PLAC test). In a specific embodiment, said modulation (e.g., suppression) is performed by contacting the immune cell(s) with a plurality of placental stem cells for a time sufficient for said placental stem cells to detectably modulate (e.g., suppress) an immune response. In another embodiment, said therapeutically effective amount is an amount that, when transplanted to an affected tissue or organ in said individual, allows the formation of colony-forming units in the affected tissue or organ.

In some embodiments, said therapeutically effective amount of placental cells results in, e.g., detectably results in, the lung functions, e.g., as determined by chest imaging, chest X-ray, CT scan of chest, PET scan or CT-guided biopsy. In other embodiments, said therapeutically effective amount of placental cells reduces the number and/or degree of skin lesions, e.g., as determined by excisional biopsy. In still other embodiments, when a cancer is involved, said placental cells reduce the number of cancerous cells, by at least, e.g., 10%, 15%, 20%, 25%, 30%, 35%, 40%, 45%, 50%, 55%, 60%, 65%, 70%, 75%, 80%, 85%, 90%, 95%, 98% or 99%, compared to the number of said cells prior to administration of said placental cells.

In another embodiment, treatment comprises treatment of an individual with sarcoidosis or a disease, disorder or condition cuased by, or relating to sarcoidosis, with a therapeutic cell composition comprising placental cells (e.g., PDACs), either with or without another cell type. In certain embodiments, the individual experiences benefits from the therapy, for example from the ability of the cells to support the growth of other cells, including stem cells or progenitor cells present in the heart, from the tissue ingrowth or vascularization of the tissue, and from the presence of beneficial cellular factors, chemokines, cytokines and the like, but the cells do not integrate or multiply in the individual. In another embodiment, the patient benefits from the therapeutic treatment with the cells, but the cells do not survive for a prolonged period in the patient. In one embodiment, the cells gradually decline in number, viability or biochemical activity, in other embodiments, the decline in cells may be preceded by a period of activity, for example growth, division, or biochemical activity. In other embodiments, senescent, nonviable or even dead cells are able to have a beneficial therapeutic effect.

Improvement in an individual having sarcoidosis or a disease, disorder or condition cuased by, or relating to sarcoidosis, wherein the individual is administered the PDACs or therapeutic compositions provided herein, can be assessed or demonstrated by detectable improvement in one or more symptoms of said sarcoidosis or said sarcoidosis-related disease or disorder.

Improvement in an individual receiving the PDACs, or therapeutic compositions comprising PDACs, provided herein can also be assessed by subjective metrics, e.g., the individual's self-assessment about his or her state of health following administration.

Success of administration of the cells is not, in certain embodiments, based on survival in the individual of the administered PDACs. Success is, instead, based on one or more metrics of improvement in one or more symptoms of sarcoidosis, as noted above. Thus, the cells need not integrate and beat with the patient's affected tissues or organs.

4.1.2 Administration of Placental Cells

In some embodiments, administration of placental cells (e.g., PDACs), or therapeutic compositions comprising such cells, to an individual in need thereof, can be accomplished, for local or systemic administration, by transplantation, implantation (e.g., of the cells themselves or the cells as part of a matrix-cell combination), injection (e.g., directly to the site of the disease or condition, for example, directly to one or more lesions or granulomas caused by, or relating to sarcoidosis), infusion, delivery via catheter, or any other means known in the art for providing cell therapy. In other embodiment, placental cells (e.g., PDACs), or therapeutic compositions comprising such cells can be delivered to an individual by intravenous, intraarterial, intraperitoneal, intrathecal, intraventricular, intraurethral, intrasternal, intracranial, intramuscular, intrasynovial, and subcutaneous administration.

In one embodiment, the therapeutic cell compositions are provided to an individual in need thereof, for example, by injection into one or more sites in the individual. In a specific embodiment, when there is cardiac involvment, the therapeutic cell compositions are provided by intracardiac injection, e.g., to an ischemic area in the heart. In other specific embodiments, the cells are injected onto the surface of the affected organ, into an adjacent area, or even to a more remote area. In preferred embodiments, the cells can home to the diseased or injured area.

In specific embodiments, the placental cells are administered intralesionally, e.g., directly into, or adjacent to (e.g., within 1-5 cm of) one or more lesions or granulomas caused by, or relating to sarcoidosis. In certain embodiments, the placental cells are administered in combination with a matrix, e.g., an injectable matrix. In certain other embodiments, placental cells are administered to an individual having sarcoidosis or a sarcoidosis-related disease or disorder in combination with a solid matrix, e.g., a bone substitute, a matrix or bone substitute described in Section 4.7.4, below.

In certain other embodiments, the placental cells are administered intravenously to the individual. The placental cells can be administered from any container, and by any delivery system, medically suitable for the delivery of fluids, e.g., fluids comprising cells, to an individual. Such containers can be, for example, a sterile plastic bag, flask, jar, or other container from which the placental cell population can be easily dispensed. For example, the container can be a blood bag or other plastic, medically-acceptable bag suitable for the intravenous administration of a liquid to a recipient.

Intralesional or intravenous administration can comprise, e.g., about, at least, or no more than $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more isolated placental cells in a single dose. The isolated placental cells may be administered once, or more than once, during a course of therapy. Preferably, the administered placental cells comprise 50% viable cells or more (that is, at least about 50% of the cells in the population are functional or living). Preferably, at least about 60% of the cells in the population are viable. More preferably, at least about 70%, 80%, 90%, 95%, or 99% of the cells in the population in the pharmaceutical composition are viable.

In certain embodiments, the individual is administered a therapeutically effective amount of PDACs, e.g., in a population of cells that comprise the PDACs. In a specific embodiment, the population comprises about 50% PDACs. In another specific embodiment, the population is a substantially homogeneous population of PDACs. In other embodiments the population comprises at least about 5%, 10%, 15%, 20%, 25%, 30%, 35%, 40%, 45%, 50%, 55%, 60%, 65%, 70%, 75%, 80%, 85% 90%, 95%, 98% or 99% PDACs.

An individual having sarcoidosis or a sarcoidosis-related disease or condition can be administered PDACs at any time the cells would be therapeutically beneficial. In certain embodiments, for example, the PDACs or therapeutic compositions of the invention are administered within 1, 2, 3, 4, 5, 6, 7, 8, 9, 10, 11, 12, 13, 14, 15, 16, 17, 18, 19, 20, 21, 22, 23, or 24 hours, or 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days of the myocardial infarction. Administration proximal in time to a myocardial infarction, e.g., within 1-3 or 1-7 days, is preferable to administration distal in time, e.g., after 3 or 7 days after a myocardial infarction. In other embodiments, the cells or therapeutic compositions of the invention are administered within 1, 2, 3, 4, 5, 6, 7, 8, 9, 10, 11, 12, 13, 14, 15, 16, 17, 18, 19, 20, 21, 22, 23, or 24 hours, or 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days of initial diagnosis of the disease or condition.

In certain embodiments, the individual to be treated is a mammal. In a specific embodiment the individual to be treated is a human of any age and/or at any clinical stage or sarcoidosis or a sarcoidosis-related disease, disorder or condition. In specific embodiments, the individual is a livestock animal or a domestic animal. In other specific embodiments, the individual to be treated is a horse, sheep, cow or steer, pig, dog or cat.

4.1.3 Combination Therapies

Treatment of sarcoidosis or a sarcoidosis-related disease or disorder, e.g., systemic sarcoidosis, can comprise administration of isolated placental cells, in particular, the isolated placental cells described in detail in Section 4.2, below (PDACs), in combination with one or more of a second therapy (e.g., second therapeutic agent), to the individual having sarcoidosis or a sarcoidosis-related disease or disorder.

The combination therapies provided herein do not restrict the order in which therapies are administered to a subject. For example, a first therapy can be administered before (e.g., 1 minute, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks), concurrently, or after (e.g., 1 minute, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks) the administration of a second therapy to a subject which had, has, or is susceptible to a given disease. Any additional therapy can be administered in any order with the other additional therapies.

In certain embodiments, the second therapeutic agent comprises TNF-α inhibitors (e.g., infliximab or adalimumab), antimalarials (e.g., chloroquine or hydroxychloroquine), thalidomide, azathioprine, mycophenolate, cyclophosphamide, chlorambucil, methotrexate, focalin, iloprost, methotrexate, nicotine, thalidomide, ambrisentan (e.g., letairis), bosentan, atorvastatin, pentoxifylline, adalimumab, rituximab, stelara (e.g., ustekinumab), aviptadil, apremilast, remicade, humira, growth factors, chemokines, cytokines, cellular products, demethylating agents, and other factors which are now known or later determined to stimulate differentiation of stem cells, insulin-like growth factor (IGF), platelet-derived growth factor (PDGF), epidermal growth factor (EGF), fibroblast growth factor (FGF), vascular endothelial growth factor (VEGF), hepatocyte growth factor (HGF), interleukin 18 (IL-8), an antithrombogenic agent (e.g., heparin, heparin derivatives, urokinase, or PPack (dextrophenylalanine proline arginine chloromethylketone), an antithrombin compound, a platelet receptor antagonist, an anti-thrombin antibody, an anti-platelet receptor antibody, aspirin, dipyridamole, protamine, hirudin, a prostaglandin inhibitor, and/or a platelet inhibitor), an antiapoptotic agent (e.g., erythropoietin (Epo), an Epo derivative or analog, or their salts, thrombopoietin (Tpo), IGF-I, IGF-II, hepatocyte growth factor (HGF), or a caspase inhibitor), an anti-inflammatory agent (e.g., a p38 MAP kinase inhibitor, a statin, in IL-6 inhibitor, an IL-1 inhibitor, Pemirolast, Tranilast, Remicade, Sirolimus, and/or a nonsteroidal anti-inflammatory compound (e.g., acetylsalicylic acid, ibuprofen, Tepoxalin, Tolmetin, or Suprofen)), an immunosuppressive or immunomodulatory agent (e.g., a calcineurin inhibitor, for example cyclosporine, Tacrolimus, an mTOR inhibitor such as Sirolimus or Everolimus; an antiproliferative such as azathioprine and/or mycophenolate mofetil; a corticosteroid, e.g., prednisone, prednisolone or hydrocortisone; a steroid-sparing agent such as azathioprine and methotrexate; an antibody such as a monoclonal anti-IL-2Rα receptor antibody, Basiliximab, Daclizuma, polyclonal anti-T-cell antibodies such as anti-thymocyte globulin (ATG), anti-lymphocyte globulin (ALG), and/or the monoclonal anti-T cell antibody OKT3, or adherent placental stem cells as described in U.S. Pat. No. 7,468,276, and U.S. Patent Application Publication No. and 2007/0275362, the disclosures of each of which are incorporated herein by reference in their entireties), and/or an antioxidant (e.g., probucol; vitamins A, C, and/or E, coenzyme Q-10, glutathione, L cysteine, N-acetylcysteine, or an antioxidant derivative, analog or salt of any of the foregoing). In certain embodiments, therapeutic compositions comprising the PDACs further comprise one or more additional cell types, e.g., adult cells (for example, fibroblasts or endodermal cells), stem cells and/or progenitor cells. Such therapeutic agents and/or one or more additional types of cells can be administered to an individual in need thereof individually or in combinations or two or more such compounds or agents.

In one embodiment, the second therapeutic agent is an anti-inflammatory agent, steroid, immune suppressant, and/or an antibiotic. Examples of anti-inflammatory drugs useful in the treatment of sarcoidosis or sarcoidosis-related diseases, disorders or conditions include, but are not limited to, mesalamine, 5-ASA (5-aminosalicylic acid) agents (e.g., ASACOL® (mesalamine, delayed-release), DIPENTUM (Osalazine), PENTASA® (mesalamine controlled-release)), sulfasalazine (a combination of 5-ASA and sulfapyridine), anti-inflammatory antibodies (e.g., Infliximab (REMICADE®)), and the like. Examples of steroids useful in the treatment of sarcoidosis or sarcoidosis-related diseases, disorders or conditions include, but are not limited to, cortisone, hydrocortisone, predisone, methylprednisone, and the like. Typically, as practiced in the art, the dosage of steroid is first delivered in a relatively large dose, followed by smaller dosages as inflammation subsides. Examples of immune suppressants useful in the treatment of sarcoidosis or sarcoidosis-related diseases include, but are not limited to, cyclosporine A, 6-mercaptopurine or azathioprine. Any antibiotic can be used in the treatment of Crohn's disease, including, e.g., ampicillin, sulfonamide, cephalosporin, tetracycline, and/or metronidazole. In another specific embodiment, the second therapy is an administration of porcine whipworms, e.g., ova of *Trichuris suis*.

In another embodiment, the second therapy provided herein is an anticancer therapy, e.g., to treat sarcoidosis-related cancers, e.g., one or more chemotherapies or chemotherapeutic compounds. Such other anticancer therapies can be administered to the individual at the same time as, during the same course of treatment as, or separately from, said administration of placental cells, e.g., PDACs. In a specific embodiment, the administration of said other anticancer therapies is administered sequentially with administration of said placental cells. In another specific embodiment, said other anticancer therapy or anticancer therapies are administered to said individual before administration of said placental cells; e.g., a course of such other anticancer therapies is administered to the individual, and completed, prior to administration to the individual of isolated placental cells. In another specific embodiment, said placental cells are administered to the individual before administration of said other anticancer therapies; e.g., a course of placental cells is administered to said individual before administration of said other anticancer therapies, and completed, prior to administration to the individual said other anticancer therapy or anticancer therapies.

In a specific embodiment, the anticancer agent is melphalan (also known as L-phenylalanine mustard or L-PAM; trade name Albertan). Thus, in one embodiment, the method of treating an individual having multiple myeloma comprises administering to said individual melphalan, e.g., a therapeutically effective dose or doses of melphalan. Administration is typically oral or intravenous. In another specific embodiment, the anticancer agent is thalidomide. In another specific embodiment, the anticancer agent is an amino-substituted thalidomide analog or an amino-substituted imidazole. In another specific embodiment, the anticancer agent is pomalidomide (sold under the trade name ACTIMID®); lenalidomide (sold under the trade name REVLIMID®); or lenalidomide in combination with dexamethasone. In another specific embodiment, the anticancer treatment is bortezomib (VELCADE®). In another specific embodiment, the anticancer agent comprises a combination of melphalan, prednisone, and thalidomide (administered separately or together). In another specific embodiment, the anticancer agent is the combination of bortezomib, melphalan and prednisone (administered separately or together).

Other anticancer agents are well-known in the art. Thus, in other specific embodiments, the anticancer agents include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidenmin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; hereguline; hexamethylene bisacetamide; hypericin; ibandronic acid; idarubicin; idoxifene; idramantone; ilmofosine; ilomastat; imatinib (e.g., GLEEVEC®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (GENASENSE®); $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

In another embodiment, the combination therapy comprises administration of placental cells in combination with bisphosphonates. In one embodiment, the bisphosphonates are clodronate and/or pamidronate.

In a specific embodiment, the combination therapy provided herein comprises administration of placental cells in combination with one or more TNF-α inhibitors (e.g., infliximab, adalimumab), coirticosteroids (e.g., prednisone), PDE-4 inhibitors (e.g., apremiliast), IL-12 inhibitors, IL-23 inhibitors, aviptadil, IFN-γ inhibitors, or antimalarials (e.g., chloroquine or hydroxychloroquine).

In a specific embodiment, said therapeutically effective amount of placental cells, optionally in combination with one or more of a second therapy (e.g., second therapeutic agent), reduces, e.g., detectably reduces, the number of, or degree of severity of, or reduces the rate of increase in the number of, or degree of severity, one or more granulomas in said individual.

In another specific embodiment, said therapeutically effective amount of placental cells, optionally in combination with one or more of a second therapy (e.g., second therapeutic agent), reduces, e.g., detectably reduces, the number of, or reduces the rate of increase in the number of, monocytes, macrophages, or activated T-lymphocytes, in combination with one or more of a second therapy (e.g., second therapeutic agent). In another specific embodiment, said therapeutically effective amount of placental cells, optionally in combination with one or more of a second therapy (e.g., second therapeutic agent), reduces, e.g., detectably reduces, the level of, or reduces the rate of increase in the level of, one or more TNF-α, IL-2, IL-12, IFN-γ, IL-1, IL-6, IL-15, or Th1 response in said individual, in combination with one or more of a second therapy (e.g., second therapeutic agent).

4.2 Isolated Placental Cells and Isolated Placental Cell Populations

The isolated placental cells, e.g., PDACs, useful in the treatment of individuals having sarcoidosis or a sarcoidosis-related disease or disorder, are cells, obtainable from a placenta or part thereof, that adhere to a tissue culture substrate and have characteristics of multipotent cells or stem cells, but are not trophoblasts. In certain embodiments, the isolated placental cells useful in the methods disclosed herein have the capacity to differentiate into non-placental cell types.

The isolated placental cells useful in the methods disclosed herein can be either fetal or maternal in origin (that is, can have the genotype of either the fetus or mother, respectively). Preferably, the isolated placental cells and populations of isolated placental cells are fetal in origin. As used herein, the phrase "fetal in origin" or "non-maternal in origin" indicates that the isolated placental cells or populations of isolated placental cells are obtained from the umbilical cord or placental structures associated with the fetus, i.e., that have the fetal genotype. As used herein, the phrase "maternal in origin" indicates that the cells or populations of cells are obtained from a placental structures associated with the mother, e.g., which have the maternal genotype. Isolated placental cells, e.g., PDACs, or populations of cells comprising the isolated placental cells, can comprise isolated placental cells that are solely fetal or maternal in origin, or can comprise a mixed population of isolated placental cells of both fetal and maternal origin. The isolated placental cells, and populations of cells comprising the isolated placental cells, can be identified and selected by the morphological, marker, and culture characteristics discussed below. In certain embodiments, any of the placental cells, e.g., placental stem cells or placental multipotent cells described herein, are autologous to a recipient, e.g., an individual who has sarcoidosis or a sarcoidosis-related disease or disorder. In certain other embodiments, any of the placental cells, e.g., placental stem cells or placental multipotent cells described herein, are heterologous to a recipient, e.g., an individual who has sarcoidosis or a sarcoidosis-related disease or disorder.

4.2.1 Physical and Morphological Characteristics

The isolated placental cells described herein (PDACs), when cultured in primary cultures or in cell culture, adhere to the tissue culture substrate, e.g., tissue culture container surface (e.g., tissue culture plastic), or to a tissue culture surface coated with extracellular matrix or ligands such as laminin, collagen (e.g., native or denatured), gelatin, fibronectin, ornithine, vitronectin, and extracellular membrane protein (e.g., MATRIGEL® (BD Discovery Labware, Bedford, Mass.)). The isolated placental cells in culture assume a generally fibroblastoid, stellate appearance, with a number of cytoplasmic processes extending from the central cell body. The cells are, however, morphologically distinguishable from fibroblasts cultured under the same conditions, as the isolated placental cells exhibit a greater number of such processes than do fibroblasts. Morphologically, isolated placental cells are also distinguishable from hematopoietic stem cells, which generally assume a more rounded, or cobblestone, morphology in culture.

In certain embodiments, the isolated placental cells useful in the methods disclosed herein, when cultured in a growth medium, develop embryoid-like bodies. Embryoid-like bodies are noncontiguous clumps of cells that can grow on top of an adherent layer of proliferating isolated placental cells. The term "embryoid-like" is used because the clumps of cells resemble embryoid bodies, clumps of cells that grow from cultures of embryonic stem cells. Growth medium in which embryoid-like bodies can develop in a proliferating culture of isolated placental cells includes medium comprising, e.g., DMEM-LG (e.g., from Gibco); 2% fetal calf serum (e.g., from Hyclone Labs.); 1× insulin-transferrin-selenium (ITS); 1× linoleic acid-bovine serum albumin (LA-BSA); $10^{-9}$ M dexamethasone (e.g., from Sigma); $10^{-4}$ M ascorbic acid 2-phosphate (e.g., from Sigma); epidermal growth factor 10 ng/mL (e.g., from R&D Systems); and platelet-derived growth factor (PDGF-BB) 10 ng/mL (e.g., from R&D Systems).

4.2.2 Cell Surface, Molecular and Genetic Markers

The isolated placental cells, e.g., isolated multipotent placental cells or isolated placental stem cells, and populations of such isolated placental cells, useful in the methods of disclosed herein, e.g., the methods of treatment of sarcoidosis or a sarcoidosis-related disease or disorder, are tissue culture plastic-adherent human placental cells that have characteristics of multipotent cells or stem cells, and express a plurality of markers that can be used to identify and/or isolate the cells, or populations of cells that comprise the stem cells. In certain embodiments, the PDACs are angiogenic, e.g., in vitro or in vivo. The isolated placental cells, and placental cell populations described herein (that is, two or more isolated placental cells) include placental cells and placental cell-containing cell populations obtained directly from the placenta, or any part thereof (e.g., chorion, placental cotyledons, or the like). Isolated placental cell populations also include populations of (that is, two or more) isolated placental cells in culture, and a population in a container, e.g., a bag. The isolated placental cells described herein are not bone marrow-derived mesenchymal cells, adipose-derived mesenchymal stem cells, or mesenchymal cells obtained from umbilical cord blood, placental blood, or peripheral blood. Placental cells, e.g., placental multipotent cells and placental cells, useful in the methods and compositions described herein are described herein and, e.g., in U.S. Pat. Nos. 7,311,904; 7,311,905; and 7,468,276; and in U.S. Patent Application Publication No. 2007/0275362, the disclosures of which are hereby incorporated by reference in their entireties.

In certain embodiments, the isolated placental cells are isolated placental stem cells. In certain other embodiments, the isolated placental cells are isolated placental multipotent cells. In one embodiment, the isolated placental cells, e.g., PDACs, are CD34$^-$, CD10$^+$ and CD105$^+$ as detected by flow cytometry. In another specific embodiment, the isolated CD34$^-$, CD10$^+$, CD105$^-$ placental cells have the potential to differentiate into cells of a neural phenotype, cells of an osteogenic phenotype, and/or cells of a chondrogenic phenotype. In another specific embodiment, the isolated CD34$^-$, CD10$^+$, CD105$^+$ placental cells are additionally CD200$^+$. In another specific embodiment, the isolated CD34$^-$, CD10$^-$, CD105$^+$ placental cells are additionally CD45$^-$ or CD90$^+$. In another specific embodiment, the isolated CD34$^-$, CD10$^+$, CD105$^+$ placental cells are additionally CD45$^-$ and CD90$^+$, as detected by flow cytometry. In another specific embodiment, the isolated CD34$^-$, CD10$^+$, CD105$^+$, CD200$^+$ placental cells are additionally CD90$^+$ or CD45$^-$, as detected by flow cytometry. In another specific embodiment, the isolated CD34$^-$, CD10$^+$, CD105$^+$, CD200$^+$ placental cells are additionally CD90$^+$ and CD45$^-$, as detected by flow cytometry, i.e., the cells are CD34$^-$, CD10$^+$, CD45$^-$, CD90$^+$, CD105$^-$ and CD200$^+$. In another specific embodiment, said CD34$^-$, CD10$^+$, CD45$^-$, CD90$^+$, CD105$^-$, CD200$^+$ cells are additionally CD80$^-$ and CD86$^-$.

In certain embodiments, said placental cells are CD34$^-$, CD10$^+$, CD105$^+$ and CD200$^+$, and one or more of CD38$^-$, CD45$^-$, CD80$^-$, CD86$^-$, CD133$^-$, HLA-DR,DP,DQ$^-$, SSEA3$^-$, SSEA4$^-$, CD29$^-$, CD44$^+$, CD73$^+$, CD90$^+$, CD105$^+$, HLA-A,B,C$^+$, PDL1$^+$, ABC-p$^+$, and/or OCT-4$^+$, as detected by flow cytometry. In other embodiments, any of the CD34$^-$, CD10$^+$, CD105$^+$ cells described above are additionally one or more of CD29$^+$, CD38$^-$, CD44$^+$, CD54$^+$, SH3$^-$ or SH4$^+$. In another specific embodiment, the cells are additionally CD44$^+$. In another specific embodiment of any of the isolated CD34$^-$, CD10$^-$, CD105$^+$ placental cells above, the cells are additionally one or more of CD117$^-$, CD133$^-$, KDR$^-$ (VEGFR2$^-$), HLA-A,B,C$^+$, HLA-DP,DQ,DR, or Programmed Death-1 Ligand (PDL1)$^+$, or any combination thereof.

In another embodiment, the CD34$^-$, CD10$^+$, CD105$^+$ cells are additionally one or more of CD13$^+$, CD29$^+$, CD33$^+$, CD38$^-$, CD44$^+$, CD45$^-$, CD54$^-$, CD62E$^-$, CD62L$^-$, CD62P$^-$, SH3$^+$ (CD73$^+$), SH4$^+$ (CD73$^+$), CD80$^-$, CD86$^-$, CD90$^+$, SH2$^+$ (CD105$^+$), CD106/VCAM$^-$, CD117$^-$, CD144/VE-cadherin$^{low}$, CD184/CXCR4$^-$, CD200$^+$, CD133$^-$, OCT-4$^+$, SSEA3$^-$, SSEA4, ABC-p$^+$, KDR (VEGFR2$^-$), HLA-A,B,C$^+$, HLA-DP,DQ,DR, HLA-G, or Programmed Death-1 Ligand (PDL1)$^+$, or any combination thereof. In a other embodiment, the CD34$^-$, CD10$^+$, CD105$^+$ cells are additionally CD13$^+$, CD29$^+$, CD33$^+$, CD38$^-$, CD44$^+$, CD45$^-$, CD54/ICAM$^+$, CD62E$^-$, CD62L$^-$, CD62P$^-$, SH3$^+$ (CD73$^-$), SH4$^+$ (CD73$^+$), CD80$^-$, CD86$^-$, CD90$^+$, SH2$^+$ (CD105$^+$), CD106/VCAM$^+$, CD116$^-$, CD144/VE-cadherin$^{low}$, CD184/CXCR4$^-$, CD200$^+$, CD133$^-$, OCT-4$^+$, SSEA3$^-$, SSEA4$^-$, ABC-p$^+$, KDR$^-$ (VEGFR2$^-$), HLA-A,B,C$^+$, HLA-DP,DQ,DR, HLA-G, and Programmed Death-1 Ligand (PDL1)$^+$.

In another specific embodiment, any of the placental cells described herein are additionally ABC-p$^+$, as detected by flow cytometry, or OCT-4$^+$ (POU5F1$^+$), as determined by RT-PCR, wherein ABC-p is a placenta-specific ABC transporter protein (also known as breast cancer resistance protein (BCRP) and as mitoxantrone resistance protein (MXR)), and OCT-4 is the Octamer-4 protein (POU5F1). In another specific embodiment, any of the placental cells described herein are additionally SSEA3$^-$ or SSEA4$^-$, as determined by flow cytometry, wherein SSEA3 is Stage Specific Embryonic Antigen 3, and SSEA4 is Stage Specific Embryonic Antigen 4. In another specific embodiment, any of the placental cells described herein are additionally SSEA3$^-$ and SSEA4$^-$.

In another specific embodiment, any of the placental cells described herein are additionally one or more of MHC-I$^+$ (e.g., HLA-A,B,C$^+$), MHC-II$^-$ (e.g., HLA-DP,DQ,DR$^-$) or HLA-G$^-$. In another specific embodiment, any of the placental cells described herein are additionally one or more of MHC-I$^+$ (e.g., HLA-A,B,C$^+$), MHC-II$^-$ (e.g., HLA-DP,DQ, DR$^-$) and HLA-G$^-$.

Also provided herein are populations of the isolated placental cells, or populations of cells, e.g., populations of placental cells, comprising, e.g., that are enriched for, the isolated placental cells, that are useful in the methods and compositions disclosed herein. Preferred populations of cells comprising the isolated placental cells, wherein the populations of cells comprise, e.g., at least 10%, 15%, 20%, 25%, 30%, 35%, 40%, 45%, 50%, 55%, 60%, 65%, 70%, 75%, 80%, 85%, 90%, 95% or 98% isolated CD10$^+$, CD105$^+$ and CD34$^-$ placental cells; that is, at least 10%, 15%, 20%, 25%, 30%, 35%, 40%, 45%, 50%, 55%, 60%, 65%, 70%, 75%, 80%, 85%, 90%, 95% or 98% of cells in said population are isolated CD10$^+$, CD105$^+$ and CD34$^-$ placental cells. In a specific embodiment, the isolated CD34$^-$, CD10$^+$, CD105$^+$ placental cells are additionally CD200$^+$. In another specific embodiment, the isolated CD34$^-$, CD10$^+$, CD105$^+$, CD200$^-$ placental cells are additionally CD90$^+$ or CD45$^-$, as detected by flow cytometry. In another specific embodiment, the isolated CD34$^-$, CD10$^+$, CD105$^+$, CD200$^+$ placental cells are additionally CD90$^+$ and CD45$^-$, as detected by flow cytometry. In another specific embodiment, any of the isolated CD34$^-$, CD10$^+$, CD105$^+$ placental cells described above are additionally one or more of CD29$^+$, CD38$^-$, CD44$^+$, CD54$^+$, SH3$^-$ or SH4$^+$. In another specific embodiment, the isolated CD34$^-$, CD10$^+$, CD105$^+$ placental cells, or isolated CD34$^-$, CD10$^+$, CD105$^+$, CD200$^+$ placental cells, are additionally CD44$^+$. In a specific embodiment of any of the populations of cells comprising isolated CD34$^-$, CD 10$^+$, CD105$^+$ placental cells above, the isolated placental cells are additionally one or more of CD13$^+$, CD29$^+$, CD33$^+$, CD38$^-$, CD44$^-$, CD45$^-$, CD54$^+$, CD62E, CD62L, CD62P$^-$, SH3$^+$ (CD73$^+$), SH4$^+$ (CD73$^+$), CD80$^-$, CD86$^-$, CD90$^-$, SH2$^+$ (CD105$^-$), CD106/VCAM$^-$, CD117$^-$, CD144/VE-cadherin$^{low}$, CD184/CXCR4$^-$, CD200$^-$, CD133$^-$, OCT-4$^+$, SSEA3$^-$, SSEA4$^-$, ABC-p$^+$, KDR$^-$ (VEGFR2$^-$), HLA-A,B,C$^+$, HLA-DP,DQ, DR$^-$, HLA-G$^-$, or Programmed Death-1 Ligand (PDL1)$^+$, or any combination thereof. In another specific embodiment, the CD34$^-$, CD10$^+$, CD105$^+$ cells are additionally CD13$^+$, CD29$^+$, CD33$^-$, CD38$^-$, CD44$^+$, CD45$^-$, CD54/ICAM$^+$, CD62E$^-$, CD62L$^-$, CD62P$^-$, SH3$^-$ (CD73$^+$), SH4$^+$ (CD73$^+$), CD80$^-$, CD86$^-$, CD90$^+$, SH2$^+$ (CD105$^+$), CD106/VCAM$^+$, CD117$^-$, CD144/VE-cadherin$^{low}$, CD184/CXCR4$^-$, CD200$^+$, CD133$^-$, OCT-4$^+$, SSEA3$^-$, SSEA4$^-$, ABC-p$^+$, KDR$^-$ (VEGFR2$^-$), HLA-A,B,C$^-$, HLA-DP,DQ,DR$^-$, HLA-G$^-$, and Programmed Death-1 Ligand (PDL1)$^+$.

In certain embodiments, the isolated placental cells useful in the methods and compositions described herein are one or more, or all, of CD10$^-$, CD29$^+$, CD34$^-$, CD38$^-$, CD44$^+$, CD45$^-$, CD54$^+$, CD90$^+$, SH2$^+$, SH3$^+$, SH4$^+$, SSEA3$^-$, SSEA4$^-$, OCT-4$^+$, and ABC-p$^+$, wherein said isolated placental cells are obtained by physical and/or enzymatic disruption of placental tissue. In a specific embodiment, the isolated placental cells are OCT-4$^+$ and ABC-p$^+$. In another specific embodiment, the isolated placental cells are OCT-4$^+$ and CD34⁻, wherein said isolated placental cells have at least one of the following characteristics: CD10⁺, CD29⁺, CD44⁺, CD45⁻, CD54⁺, CD90⁺, SH3⁺, SH4⁺, SSEA3⁻, and SSEA4⁻. In another specific embodiment, the isolated placental cells are OCT-4⁺, CD34⁻, CD10⁺, CD29⁺, CD44⁺, CD45⁻, CD54⁺, CD90⁺, SH3⁺, SH4⁺, SSEA3⁻, and SSEA4⁻. In another embodiment, the isolated placental cells are OCT-4⁺, CD34⁻, SSEA3⁻, and SSEA4⁻. In another specific embodiment, the isolated placental cells are OCT-4⁺ and CD34⁻, and is either SH2⁺ or SH3⁺. In another specific embodiment, the isolated placental cells are OCT-4⁺, CD34⁻, SH2⁺, and SH3⁺. In another specific embodiment, the isolated placental cells are OCT-4⁺, CD34⁻, SSEA3⁻, and SSEA4⁻, and are either SH2⁺ or SH3⁺. In another specific embodiment, the isolated placental cells are OCT-4⁺ and CD34⁻, and either SH2⁺ or SH3⁻, and is at least one of CD10⁺, CD29⁺, CD44⁺, CD45⁻, CD54⁺, CD90⁺, SSEA3⁻, or SSEA4⁻. In another specific embodiment, the isolated placental cells are OCT-4⁺, CD34⁻, CD10⁻, CD29⁺, CD44 ⁺, CD45⁻, , CD54⁺, CD90⁺, SSEA3⁻, and SSEA4⁻, and either SH2⁺ or SH3⁺.

In another embodiment, the isolated placental cells useful in the methods and compositions disclosed herein are SH2⁺, SH3⁺, SH4⁺ and OCT-4⁺. In another specific embodiment, the isolated placental cells are CD10⁺, CD29⁺, CD44⁺, CD54⁺, CD90⁺, CD34⁻, CD45⁻, , SSEA3, or SSEA4. In another embodiment, the isolated placental cells are SH2⁺, SH3⁺, SH4⁺, SSEA3⁻ and SSEA4⁻. In another specific embodiment, the isolated placental cells are SH2⁺, SH3⁺, SH4⁺, SSEA3⁻ and SSEA4⁻, CD10⁺, CD29⁺, CD44⁺, CD54⁻, CD90⁺, OCT-4⁺, CD34⁻ or CD45⁻.

In another embodiment, the isolated placental cells useful in the methods and compositions disclosed herein are CD10⁺, CD29⁻, CD34⁻, CD44⁺, CD45⁻, CD54⁻, CD90⁺, SH2⁺, SH3⁺, and SH4⁺; wherein said isolated placental cells are additionally one or more of OCT-4⁺, SSEA3⁻ or SSEA4⁻.

In certain embodiments, isolated placental cells useful in the methods and compositions disclosed herein are CD200⁺ or HLA-G⁻. In a specific embodiment, the isolated placental cells are CD200⁺ and HLA-G⁻. In another specific embodiment, the isolated placental cells are additionally CD73⁺ and CD105⁺. In another specific embodiment, the isolated placental cells are additionally CD34⁻, CD38⁻ or CD45⁻. In another specific embodiment, the isolated placental cells are additionally CD34⁻, CD38⁻ and CD45⁻. In another specific embodiment, said stem cells are CD34⁻, CD38⁻, CD45⁻, CD73⁺ and CD105⁺. In another specific embodiment, said isolated CD200⁺ or HLA-G⁻ placental cells facilitate the formation of embryoid-like bodies in a population of placental cells comprising the isolated placental cells, under conditions that allow the formation of embryoid-like bodies. In another specific embodiment, the isolated placental cells are isolated away from placental cells that are not stem or multipotent cells. In another specific embodiment, said isolated placental cells are isolated away from placental cells that do not display these markers.

In another embodiment, a cell population useful in the methods and compositions described herein is a population of cells comprising, e.g., that is enriched for, CD200⁺, HLA-G⁻ stem cells. In a specific embodiment, said population is a population of placental cells. In various embodiments, at least about 10%, at least about 20%, at least about 30%, at least about 40%, at least about 50%, or at least about 60% of cells in said cell population are isolated CD200⁺, HLA-G⁻ placental cells. Preferably, at least about 70% of cells in said cell population are isolated CD200⁺, HLA-G⁻ placental cells. More preferably, at least about 90%, 95%, or 99% of said cells are isolated CD200⁺, HLA-G⁻ placental cells. In a specific embodiment of the cell populations, said isolated CD200⁺, HLA-G⁻ placental cells are also CD73⁺ and CD105⁺. In another specific embodiment, said isolated CD200⁺, HLA-G⁻ placental cells are also CD34⁻, CD38⁻ or CD45⁻. In another specific embodiment, said isolated CD200⁺, HLA-G⁻ placental cells are also CD34⁻, CD38⁻, CD45⁻, CD73⁺ and CD105⁺. In another embodiment, said cell population produces one or more embryoid-like bodies when cultured under conditions that allow the formation of embryoid-like bodies. In another specific embodiment, said cell population is isolated away from placental cells that are not stem cells. In another specific embodiment, said isolated CD200⁺, HLA-G⁻ placental cells are isolated away from placental cells that do not display these markers.

In another embodiment, the isolated placental cells useful in the methods and compositions described herein are CD73⁻, CD105⁺, and CD200⁻. In another specific embodiment, the isolated placental cells are HLA-G⁻. In another specific embodiment, the isolated placental cells are CD34⁻, CD38⁻ or CD45⁻. In another specific embodiment, the isolated placental cells are CD34⁻, CD38⁻ and CD45⁻. In another specific embodiment, the isolated placental cells are CD34⁻, CD38⁻, CD45⁻, and HLA-G⁻. In another specific embodiment, the isolated CD73⁺, CD105⁺, and CD200⁺ placental cells facilitate the formation of one or more embryoid-like bodies in a population of placental cells comprising the isolated placental cells, when the population is cultured under conditions that allow the formation of embryoid-like bodies. In another specific embodiment, the isolated placental cells are isolated away from placental cells that are not the isolated placental cells. In another specific embodiment, the isolated placental cells are isolated away from placental cells that do not display these markers.

In another embodiment, a cell population useful in the methods and compositions described herein is a population of cells comprising, e.g., that is enriched for, isolated CD73⁺, CD105⁺, CD200⁺ placental cells. In various embodiments, at least about 10%, at least about 20%, at least about 30%, at least about 40%, at least about 50%, or at least about 60% of cells in said cell population are isolated CD73⁺, CD105⁻, CD200⁺ placental cells. In another embodiment, at least about 70% of said cells in said population of cells are isolated CD73⁺, CD105⁺, CD200⁺ placental cells. In another embodiment, at least about 90%, 95% or 99% of cells in said population of cells are isolated CD73⁻, CD105⁺, CD200⁺ placental cells. In a specific embodiment of said populations, the isolated placental cells are HLA-G⁻. In another specific embodiment, the isolated placental cells are additionally CD34⁻, CD38⁻ or CD45⁻. In another specific embodiment, the isolated placental cells are additionally CD34⁻, CD38⁻ and CD45⁻, . In another specific embodiment, the isolated placental cells are additionally CD34⁻, CD38⁻, CD45⁻, and HLA-G⁻. In another specific embodiment, said population of cells produces one or more embryoid-like bodies when cultured under conditions that allow the formation of embryoid-like bodies. In another specific embodiment, said population of placental cells is isolated away from placental cells that are not stem cells. In another specific embodiment, said population of placental cells is isolated away from placental cells that do not display these characteristics.

In certain other embodiments, the isolated placental cells are one or more of CD10⁺, CD29⁺, CD34⁻, CD38⁻, CD44⁺, CD45⁻, CD54⁺, CD90⁺, SH2⁺, SH3⁺, SH4⁺, SSEA3−, SSEA4⁻, OCT-4⁺, HLA-G⁻ or ABC-p⁻. In a specific embodiment, the isolated placental cells are CD10⁺, CD29⁺, CD34⁻, CD38⁻, CD44⁺, CD45⁻, CD54⁺, CD90⁺, SH2⁺, SH3⁺, SH4⁺, SSEA3−, SSEA4⁻, and OCT-4⁺. In another specific embodiment, the isolated placental cells are $CD10^+$, $CD29^+$, $CD34^-$, $CD38^-$, $CD45^-$, $CD54^+$, $SH2^+$, $SH3^+$, and $SH4^+$. In another specific embodiment, the isolated placental cells are $CD10^+$, $CD29^+$, $CD34^-$, $CD38^-$, $CD45^-$, $CD54^+$, $SH2^-$, $SH3^+$, $SH4^+$ and $OCT-4^+$. In another specific embodiment, the isolated placental cells are $CD10^+$, $CD29^+$, $CD34^-$, $CD38^-$, $CD44^+$, $CD45^-$, $CD54^+$, $CD90^+$, $HLA-G^-$, $SH2^+$, $SH3^+$, $SH4^+$. In another specific embodiment, the isolated placental cells are $OCT-4^+$ and $ABC-p^+$. In another specific embodiment, the isolated placental cells are $SH2^-$, $SH3^+$, $SH4^+$ and $OCT-4^+$. In another embodiment, the isolated placental cells are $OCT-4^+$, $CD34^-$, $SSEA3^-$, and $SSEA4^-$. In a specific embodiment, said isolated $OCT-4^+$, $CD34^-$, $SSEA3^-$, and $SSEA4^-$ placental cells are additionally $CD10^+$, $CD29^+$, $CD34^-$, $CD44^+$, $CD45^-$, $CD54^+$, $CD90^+$, $SH2^-$, $SH3^+$, and $SH4^+$. In another embodiment, the isolated placental cells are $OCT-4^+$ and $CD34^-$, and either $SH3^+$ or $SH4^+$. In another embodiment, the isolated placental cells are $CD34^-$ and either $CD10^+$, $CD29^+$, $CD44^+$, $CD54^+$, $CD90^+$, or $OCT-4^+$.

In another embodiment, the isolated placental cells useful in the methods and compositions described herein are $CD200^+$ and $OCT-4^+$. In a specific embodiment, the isolated placental cells are $CD73^+$ and $CD105^+$. In another specific embodiment, said isolated placental cells are $HLA-G^-$. In another specific embodiment, said isolated $CD200^+$, $OCT-4^+$ placental cells are $CD34^-$, $CD38^-$ or $CD45^-$, . In another specific embodiment, said isolated $CD200^+$, $OCT-4^+$ placental cells are $CD34^-$, $CD38^-$ and $CD45^-$. In another specific embodiment, said isolated $CD200^+$, $OCT-4^+$ placental cells are $CD34^-$, $CD38^-$, $CD45^-$, $CD73^+$, $CD105^-$ and $HLA-G^-$. In another specific embodiment, the isolated $CD200^-$, $OCT-4^+$ placental cells facilitate the production of one or more embryoid-like bodies by a population of placental cells that comprises the isolated cells, when the population is cultured under conditions that allow the formation of embryoid-like bodies. In another specific embodiment, said isolated $CD200^+$, $OCT-4^+$ placental cells are isolated away from placental cells that are not stem cells. In another specific embodiment, said isolated $CD200^+$, $OCT-4^+$ placental cells are isolated away from placental cells that do not display these characteristics.

In another embodiment, a cell population useful in the methods and compositions described herein is a population of cells comprising, e.g., that is enriched for, $CD200^+$, $OCT-4^+$ placental cells. In various embodiments, at least about 10%, at least about 20%, at least about 30%, at least about 40%, at least about 50%, or at least about 60% of cells in said cell population are isolated $CD200^-$, $OCT-4^+$ placental cells. In another embodiment, at least about 70% of said cells are said isolated $CD200^+$, $OCT-4^+$ placental cells. In another embodiment, at least about 80%, 90%, 95%, or 99% of cells in said cell population are said isolated $CD200^+$, $OCT-4^+$ placental cells. In a specific embodiment of the isolated populations, said isolated $CD200^+$, $OCT-4^+$ placental cells are additionally $CD73^+$ and $CD105^+$. In another specific embodiment, said isolated $CD200^+$, $OCT-4^+$ placental cells are additionally $HLA-G^-$. In another specific embodiment, said isolated $CD200^+$, $OCT-4^+$ placental cells are additionally $CD34^-$, $CD38^-$ and $CD45^-$. In another specific embodiment, said isolated $CD200^+$, $OCT-4^+$ placental cells are additionally $CD34^-$, $CD38^-$, $CD45^-$, $CD73^+$, $CD105^+$ and $HLA-G^-$. In another specific embodiment, the cell population produces one or more embryoid-like bodies when cultured under conditions that allow the formation of embryoid-like bodies. In another specific embodiment, said cell population is isolated away from placental cells that are not isolated $CD200^+$, $OCT-4^+$ placental cells. In another specific embodiment, said cell population is isolated away from placental cells that do not display these markers.

In another embodiment, the isolated placental cells useful in the methods and compositions described herein are $CD73^-$, $CD105^+$ and $HLA-G^-$. In another specific embodiment, the isolated $CD73^+$, $CD105^+$ and $HLA-G^-$ placental cells are additionally $CD34^-$, $CD38^-$ or $CD45^-$. In another specific embodiment, the isolated $CD73^+$, $CD105^+$, $HLA-G$ placental cells are additionally $CD34^-$, $CD38^-$ and $CD45^-$, . In another specific embodiment, the isolated $CD73^+$, $CD105^+$, $HLA-G^-$ placental cells are additionally $OCT-4^+$. In another specific embodiment, the isolated $CD73^+$, $CD105^+$, $HLA-G^-$ placental cells are additionally $CD200^+$. In another specific embodiment, the isolated $CD73^+$, $CD105^+$, $HLA-G^-$ placental cells are additionally $CD34^-$, $CD38^-$, $CD45^-$, $OCT-4^+$ and $CD200^+$. In another specific embodiment, the isolated $CD73^+$, $CD105^+$, $HLA-G^-$ placental cells facilitate the formation of embryoid-like bodies in a population of placental cells comprising said cells, when the population is cultured under conditions that allow the formation of embryoid-like bodies. In another specific embodiment, said the isolated $CD73^+$, $CD105^+$, $HLA-G^-$ placental cells are isolated away from placental cells that are not the isolated $CD73^+$, $CD105^-$, $HLA-G^-$ placental cells. In another specific embodiment, said the isolated $CD73^+$, $CD105^+$, $HLA-G^-$ placental cells are isolated away from placental cells that do not display these markers.

In another embodiment, a cell population useful in the methods and compositions described herein is a population of cells comprising, e.g., that is enriched for, isolated $CD73^+$, $CD105^+$ and $HLA-G^-$ placental cells. In various embodiments, at least about 10%, at least about 20%, at least about 30%, at least about 40%, at least about 50%, or at least about 60% of cells in said population of cells are isolated $CD73^+$, $CD105^+$, $HLA-G^-$ placental cells. In another embodiment, at least about 70% of cells in said population of cells are isolated $CD73^+$, $CD105^-$, $HLA-G^-$ placental cells. In another embodiment, at least about 90%, 95% or 99% of cells in said population of cells are isolated $CD73^-$, $CD105^+$, $HLA-G^-$ placental cells. In a specific embodiment of the above populations, said isolated $CD73^+$, $CD105^-$, $HLA-G^-$ placental cells are additionally $CD34^-$, $CD38^-$ or $CD45^-$. In another specific embodiment, said isolated $CD73^+$, $CD105^+$, $HLA-G^-$ placental cells are additionally $CD34^-$, $CD38^-$ and $CD45^-$. In another specific embodiment, said isolated $CD73^+$, $CD105^+$, $HLA-G^-$ placental cells are additionally $OCT-4^+$. In another specific embodiment, said isolated $CD73^+$, $CD105^-$, $HLA-G^-$ placental cells are additionally $CD200^+$. In another specific embodiment, said isolated $CD73^+$, $CD105^+$, $HLA-G^-$ placental cells are additionally $CD34^-$, $CD38^-$, $CD45^-$, $OCT-4^+$ and $CD200^-$. In another specific embodiment, said cell population is isolated away from placental cells that are not $CD73^-$, $CD105^+$, $HLA-G^-$ placental cells. In another specific embodiment, said cell population is isolated away from placental cells that do not display these markers.

In another embodiment, the isolated placental cells useful in the methods and compositions described herein are $CD73^-$ and $CD105^+$ and facilitate the formation of one or more embryoid-like bodies in a population of isolated placental cells comprising said $CD73^+$, $CD105^+$ cells when said population is cultured under conditions that allow formation of embryoid-like bodies. In another specific embodiment, said isolated $CD73^+$, $CD105^+$ placental cells are additionally $CD34^-$, $CD38^-$ or $CD45^-$. In another specific embodiment, said isolated $CD73^+$, $CD105^+$ placental cells are additionally CD34$^-$, CD38$^-$ and CD45$^-$. In another specific embodiment, said isolated CD73$^+$, CD105$^-$ placental cells are additionally OCT-4$^+$. In another specific embodiment, said isolated CD73$^+$, CD105$^+$ placental cells are additionally OCT-4$^+$, CD34$^-$, CD38$^-$ and CD45$^-$, . In another specific embodiment, said isolated CD73$^+$, CD105$^+$ placental cells are isolated away from placental cells that are not said cells. In another specific embodiment, said isolated CD73$^+$, CD105$^+$ placental cells are isolated away from placental cells that do not display these characteristics.

In another embodiment, a cell population useful in the methods and compositions described herein is a population of cells comprising, e.g., that is enriched for, isolated placental cells that are CD73$^-$, CD105$^+$ and facilitate the formation of one or more embryoid-like bodies in a population of isolated placental cells comprising said cells when said population is cultured under conditions that allow formation of embryoid-like bodies. In various embodiments, at least about 10%, at least about 20%, at least about 30%, at least about 40%, at least about 50%, or at least about 60% of cells in said population of cells are said isolated CD73$^+$, CD105$^+$ placental cells. In another embodiment, at least about 70% of cells in said population of cells are said isolated CD73$^+$, CD105$^-$ placental cells. In another embodiment, at least about 90%, 95% or 99% of cells in said population of cells are said isolated CD73$^+$, CD105$^+$ placental cells. In a specific embodiment of the above populations, said isolated CD73$^+$, CD105$^+$ placental cells are additionally CD34$^-$, CD38$^-$ or CD45$^-$. In another specific embodiment, said isolated CD73$^+$, CD105$^-$ placental cells are additionally CD34$^-$, CD38$^-$ and CD45$^-$. In another specific embodiment, said isolated CD73$^+$, CD105$^+$ placental cells are additionally OCT-4$^+$. In another specific embodiment, said isolated CD73$^+$, CD105$^-$ placental cells are additionally CD200$^-$. In another specific embodiment, said isolated CD73$^+$, CD105$^+$ placental cells are additionally CD34$^-$, CD38$^-$, CD45$^-$, OCT-4$^+$ and CD200$^+$. In another specific embodiment, said cell population is isolated away from placental cells that are not said isolated CD73$^-$, CD105$^+$ placental cells. In another specific embodiment, said cell population is isolated away from placental cells that do not display these markers.

In another embodiment, the isolated placental cells useful in the methods and compositions described herein are OCT-4$^+$ and facilitate formation of one or more embryoid-like bodies in a population of isolated placental cells comprising said cells when cultured under conditions that allow formation of embryoid-like bodies. In a specific embodiment, said isolated OCT-4$^+$ placental cells are additionally CD73$^+$ and CD105$^+$. In another specific embodiment, said isolated OCT-4$^+$ placental cells are additionally CD34$^-$, CD38$^-$, or CD45$^-$. In another specific embodiment, said isolated OCT-4$^+$ placental cells are additionally CD200$^+$. In another specific embodiment, said isolated OCT-4$^+$ placental cells are additionally CD73$^+$, CD105$^+$, CD200$^-$, CD34$^-$, CD38$^-$, and CD45$^-$, . In another specific embodiment, said isolated OCT-4$^+$ placental cells are isolated away from placental cells that are not OCT-4$^+$ placental cells. In another specific embodiment, said isolated OCT-4$^+$ placental cells are isolated away from placental cells that do not display these characteristics.

In another embodiment, a cell population useful in the methods and compositions described herein is a population of cells comprising, e.g., that is enriched for, isolated placental cells that are OCT-4$^+$ and facilitate the formation of one or more embryoid-like bodies in a population of isolated placental cells comprising said cells when said population is cultured under conditions that allow formation of embryoid-like bodies. In various embodiments, at least about 10%, at least about 20%, at least about 30%, at least about 40%, at least about 50%, or at least about 60% of cells in said population of cells are said isolated OCT-4$^+$ placental cells. In another embodiment, at least about 70% of cells in said population of cells are said isolated OCT-4$^+$ placental cells. In another embodiment, at least about 80%, 90%, 95% or 99% of cells in said population of cells are said isolated OCT-4$^+$ placental cells. In a specific embodiment of the above populations, said isolated OCT-4$^+$ placental cells are additionally CD34$^-$, CD38$^-$ or CD45$^-$. In another specific embodiment, said isolated OCT-4$^+$ placental cells are additionally CD34$^-$, CD38$^-$ and CD45$^-$. In another specific embodiment, said isolated OCT-4$^+$ placental cells are additionally CD73$^+$ and CD105$^+$. In another specific embodiment, said isolated OCT-4$^+$ placental cells are additionally CD200$^+$. In another specific embodiment, said isolated OCT-4$^+$ placental cells are additionally CD73$^+$, CD105$^+$, CD200$^+$, CD34$^-$, CD38$^-$, and CD45$^-$. In another specific embodiment, said cell population is isolated away from placental cells that are not said cells. In another specific embodiment, said cell population is isolated away from placental cells that do not display these markers.

In another embodiment, the isolated placental cells useful in the methods and compositions described herein are isolated HLA-A,B,C$^+$, CD45$^-$, CD133$^-$ and CD34$^-$ placental cells. In another embodiment, a cell population useful in the methods and compositions described herein is a population of cells comprising isolated placental cells, wherein at least about 70%, at least about 80%, at least about 90%, at least about 95% or at least about 99% of cells in said isolated population of cells are isolated HLA-A,B,C$^+$, CD45$^-$, CD133$^-$ and CD34$^-$ placental cells. In a specific embodiment, said isolated placental cell or population of isolated placental cells is isolated away from placental cells that are not HLA-A,B,C$^+$, CD45$^-$, CD133$^-$ and CD34$^-$ placental cells. In another specific embodiment, said isolated placental cells are non-maternal in origin. In another specific embodiment, said isolated population of placental cells are substantially free of maternal components; e.g., at least about 40%, 45%, 5-0%, 55%, 60%, 65%, 70%, 75%, 90%, 85%, 90%, 95%, 98% or 99% of said cells in said isolated population of placental cells are non-maternal in origin.

In another embodiment, the isolated placental cells useful in the methods and compositions described herein are isolated CD10$^+$, CD13$^+$, CD33$^-$, CD45$^-$, , CD117 and CD133$^-$ placental cells. In another embodiment, a cell population useful in the methods and compositions described herein is a population of cells comprising isolated placental cells, wherein at least about 70%, at least about 80%, at least about 90%, at least about 95% or at least about 99% of cells in said population of cells are isolated CD10$^+$, CD13$^+$, CD33$^+$, CD45$^-$, CD117$^-$ and CD133$^-$ placental cells. In a specific embodiment, said isolated placental cells or population of isolated placental cells is isolated away from placental cells that are not said isolated placental cells. In another specific embodiment, said isolated CD10$^+$, CD13$^+$, CD33$^+$, CD45$^-$, CD117$^-$ and CD133$^-$ placental cells are non-maternal in origin, i.e., have the fetal genotype. In another specific embodiment, at least about 40%, 45%, 50%, 55%, 60%, 65%, 70%, 75%, 90%, 85%, 90%, 95%, 98% or 99% of said cells in said isolated population of placental cells, are non-maternal in origin. In another specific embodiment, said isolated placental cells or population of isolated placental cells are isolated away from placental cells that do not display these characteristics.

In another embodiment, the isolated placental cells useful in the methods and compositions described herein are isolated CD10$^-$, CD33$^-$, CD44$^+$, CD45$^-$, and CD11$^{117-}$ placental cells. In another embodiment, a cell population useful for the in the methods and compositions described herein is a population of cells comprising, e.g., enriched for, isolated placental cells, wherein at least about 70%, at least about 80%, at least about 90%, at least about 95% or at least about 99% of cells in said population of cells are isolated CD10⁻, CD33⁻, CD44⁺, CD45⁻, and CD117⁻ placental cells. In a specific embodiment, said isolated placental cell or population of isolated placental cells is isolated away from placental cells that are not said cells. In another specific embodiment, said isolated placental cells are non-maternal in origin. In another specific embodiment, at least about 40%, 45%, 50%, 55%, 60%, 65%, 70%, 75%, 90%, 85%, 90%, 95%, 98% or 99% of said cells in said cell population are non-maternal in origin. In another specific embodiment, said isolated placental cell or population of isolated placental cells is isolated away from placental cells that do not display these markers.

In another embodiment, the isolated placental cells useful in the methods and compositions described herein are isolated CD10⁻, CD13⁻, CD33⁻, CD45⁻, and CD117⁻ placental cells. In another embodiment, a cell population useful for in the methods and compositions described herein is a population of cells comprising, e.g., enriched for, isolated CD10⁻, CD13⁻, CD33⁻, CD45⁻, and CD117⁻ placental cells, wherein at least about 70%, at least about 80%, at least about 90%, at least about 95% or at least about 99% of cells in said population are CD10⁻, CD13⁻, CD33⁻, CD45⁻, , and CD117⁻ placental cells. In a specific embodiment, said isolated placental cells or population of isolated placental cells are isolated away from placental cells that are not said cells. In another specific embodiment, said isolated placental cells are non-maternal in origin. In another specific embodiment, at least about 40%, 45%, 50%, 55%, 60%, 65%, 70%, 75%, 90%, 85%, 90%, 95%, 98% or 99% of said cells in said cell population are non-maternal in origin. In another specific embodiment, said isolated placental cells or population of isolated placental cells is isolated away from placental cells that do not display these characteristics.

In another embodiment, the isolated placental cells useful in the methods and compositions described herein are HLA A,B,C⁺, CD45⁻, CD34⁻, and CD133⁻, and are additionally CD10⁺, CD13⁺, CD38⁺, CD44⁺, CD90⁺, CD105⁺, CD200⁺ and/or HLA-G⁻, and/or negative for CD117. In another embodiment, a cell population useful in the methods described herein is a population of cells comprising isolated placental cells, wherein at least about 20%, 25%, 30%, 35%, 40%, 45%, 50%, 55%, 60%, 65%, 70%, 75%, 80%, 85%, 90%, 95%, 98% or about 99% of the cells in said population are isolated placental cells that are HLA A,B,C⁻, CD45⁻, CD34⁻, CD133⁻, and that are additionally positive for CD10, CD13, CD38, CD44, CD90, CD105, CD200, and/or negative for CD117 and/or HLA-G. In a specific embodiment, said isolated placental cells or population of isolated placental cells are isolated away from placental cells that are not said cells. In another specific embodiment, said isolated placental cells are non-maternal in origin. In another specific embodiment, at least about 40%, 45%, 50%, 55%, 60%, 65%, 70%, 75%, 90%, 85%, 90%, 95%, 98% or 99% of said cells in said cell population are non-maternal in origin. In another specific embodiment, said isolated placental cells or population of isolated placental cells are isolated away from placental cells that do not display these markers.

In another embodiment, the isolated placental cells useful in the methods and compositions described herein are isolated placental cells that are CD200⁺ and CD10⁺, as determined by antibody binding, and CD117⁻, as determined by both antibody binding and RT-PCR. In another embodiment, the isolated placental cells useful in the methods and compositions described herein are isolated placental cells, e.g., placental stem cells or placental multipotent cells, that are CD10⁺, CD29⁻, CD54⁺, CD200⁺, HLA-G⁻, MHC class I⁺ and β-2-microglobulin⁺. In another embodiment, isolated placental cells useful in the methods and compositions described herein are placental cells wherein the expression of at least one cellular marker is at least two-fold higher than for a mesenchymal stem cell (e.g., a bone marrow-derived mesenchymal stem cell). In another specific embodiment, said isolated placental cells are non-maternal in origin. In another specific embodiment, at least about 40%, 45%, 50%, 55%, 60%, 65%, 70%, 75%, 90%, 85%, 90%, 95%, 98% or 99% of said cells in said cell population are non-maternal in origin.

In another embodiment, the isolated placental cells useful in the methods and compositions described herein are isolated placental cells, e.g., placental stem cells or placental multipotent cells, that are one or more of CD10⁺, CD29⁺, CD44⁺, CD45⁻, CD54/ICAM⁻, CD62E⁻, CD62L⁻, CD62P⁻, CD80⁻, CD86⁻, CD103⁻, CD104⁻, CD105⁺, CD106/VCAM⁻, CD144/VE-cadherin$^{low}$, CD184/CXCR4⁻, β2-microglobulin$^{low}$, MHC-I$^{low}$, MHC-II⁻, HLA-G$^{low}$, and/or PDL1$^{low}$. In a specific embodiment, the isolated placental cells are at least CD29⁺ and CD54⁺. In another specific embodiment, the isolated placental cells are at least CD44⁺ and CD106⁺. In another specific embodiment, the isolated placental cells are at least CD29⁺.

In another embodiment, a cell population useful in the methods and compositions described herein comprises isolated placental cells, and at least 50%, 60%, 70%, 80%, 90%, 95%, 98% or 99% of the cells in said cell population are isolated placental cells that are one or more of CD10⁺, CD29⁺, CD44⁺, CD45⁻, CD54/ICAM⁺, CD62-E⁻, CD62-L⁻, CD62-P⁻, CD80⁻, CD86⁻, CD103⁻, CD104⁻, CD105⁺, CD106/VCAM⁺, CD144/VE-cadherin$^{dim}$, CD184/CXCR4⁻, β2-microglobulin$^{dim}$, HLA-I$^{dim}$, HLA-II⁻, HLA-G$^{dim}$, and/or PDL1$^{dim}$. In another specific embodiment, at least 50%, 60%, 70%, 80%, 90%, 95%, 98% or 99% of cells in said cell population are CD10⁺, CD29⁺, CD44⁺, CD45⁻, CD54/ICAM⁺, CD62-E⁻, CD62-L⁻, CD62-P⁻, CD80⁻, CD86⁻, CD103⁻, CD104⁻, CD105⁺, CD106/VCAM⁻, CD144/VE-cadherin$^{dim}$, CD184/CXCR4⁻, β2-microglobulin$^{dim}$, MHC-I$^{dim}$, MHC-II⁻, HLA-G$^{dim}$, and PDL1$^{dim}$.

In another embodiment, the isolated placental cells useful in the methods and compositions described herein are isolated placental cells that are one or more, or all, of CD10⁺, CD29⁺, CD34⁻, CD38⁻, CD44⁺, CD45⁻, CD54⁺, CD90⁺, SH2⁺, SH3⁺, SH4⁺, SSEA3⁻, SSEA4⁻, OCT-4⁻, and ABC-p⁺, where ABC-p is a placenta-specific ABC transporter protein (also known as breast cancer resistance protein (BCRP) and as mitoxantrone resistance protein (MXR)), wherein said isolated placental cells are obtained by perfusion of a mammalian, e.g., human, placenta that has been drained of cord blood and perfused to remove residual blood.

In another specific embodiment of any of the above characteristics, expression of the cellular marker (e.g., cluster of differentiation or immunogenic marker) is determined by flow cytometry; in another specific embodiment, expression of the marker is determined by RT-PCR.

Gene profiling confirms that isolated placental cells, and populations of isolated placental cells, are distinguishable from other cells, e.g., mesenchymal stem cells, e.g., bone marrow-derived mesenchymal stem cells. The isolated placental cells described herein can be distinguished from, e.g., mesenchymal stem cells on the basis of the expression of one or more genes, the expression of which is significantly higher in the isolated placental cells, or in certain isolated umbilical cord stem cells, in comparison to bone marrow-derived mesenchymal stem cells. In particular, the isolated placental cells, useful in the methods of treatment provided herein, can be distinguished from mesenchymal stem cells on the basis of the expression of one or more genes, the expression of which is significantly higher (that is, at least twofold higher) in the isolated placental cells than in an equivalent number of bone marrow-derived mesenchymal stem cells, wherein the one or more genes are ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, ZC3H12A, or a combination of any of the foregoing, when the cells are grown under equivalent conditions. See, e.g., U.S. Patent Application Publication No. 2007/0275362, the disclosure of which is incorporated herein by reference in its entirety. In certain specific embodiments, said expression of said one ore more genes is determined, e.g., by RT-PCR or microarray analysis, e.g, using a U133-A microarray (Affymetrix). In another specific embodiment, said isolated placental cells express said one or more genes when cultured for a number of population doublings, e.g., anywhere from about 3 to about 35 population doublings, in a medium comprising DMEM-LG (e.g., from Gibco); 2% fetal calf serum (e.g., from Hyclone Labs.); 1× insulin-transferrin-selenium (ITS); 1× linoleic acid-bovine serum albumin (LA-BSA); $10^{-9}$ M dexamethasone (e.g., from Sigma); $10^{-4}$ M ascorbic acid 2-phosphate (e.g., from Sigma); epidermal growth factor 10 ng/mL (e.g., from R&D Systems); and platelet-derived growth factor (PDGF-BB) 10 ng/mL (e.g., from R&D Systems). In another specific embodiment, the isolated placental cell-specific or isolated umbilical cord cell-specific gene is CD200.

Specific sequences for these genes can be found in GenBank at accession nos. NM_001615 (ACTG2), BC065545 (ADARB1), (NM_181847 (AMIGO2), AY358590 (ARTS-1), BC074884 (B4GALT6), BC008396 (BCHE), BC020196 (C11orf9), BC031103 (CD200), NM_001845 (COL4A1), NM_001846 (COL4A2), BC052289 (CPA4), BC094758 (DMD), AF293359 (DSC3), NM_001943 (DSG2), AF338241 (ELOVL2), AY336105 (F2RL1), NM_018215 (FLJ10781), AY416799 (GATA6), BC075798 (GPR126), NM_016235 (GPRC5B), AF340038 (ICAM1), BC000844 (IER3), BC066339 (IGFBP7), BC013142 (IL1A), BT019749 (IL6), BC007461 (IL18), (BC072017) KRT18, BC075839 (KRT8), BC060825 (LIPG), BC065240 (LRAP), BC010444 (MATN2), BC011908 (MEST), BC068455 (NFE2L3), NM_014840 (NUAK1), AB006755 (PCDH7), NM_014476 (PDLIM3), BC126199 (PKP-2), BC090862 (RTN1), BC002538 (SERPINB9), BC023312 (ST3GAL6), BC001201 (ST6GALNAC5), BC126160 or BC065328 (SLC12A8), BC025697 (TCF21), BC096235 (TGFB2), BC005046 (VTN), and BC005001 (ZC3H12A) as of March 2008.

In certain specific embodiments, said isolated placental cells express each of ACTG2, ADARB1, AMIGO2, ARTS-1, B4GALT6, BCHE, C11orf9, CD200, COL4A1, COL4A2, CPA4, DMD, DSC3, DSG2, ELOVL2, F2RL1, FLJ10781, GATA6, GPR126, GPRC5B, HLA-G, ICAM1, IER3, IGFBP7, IL1A, IL6, IL18, KRT18, KRT8, LIPG, LRAP, MATN2, MEST, NFE2L3, NUAK1, PCDH7, PDLIM3, PKP2, RTN1, SERPINB9, ST3GAL6, ST6GALNAC5, SLC12A8, TCF21, TGFB2, VTN, and ZC3H12A at a detectably higher level than an equivalent number of bone marrow-derived mesenchymal stem cells, when the cells are grown under equivalent conditions.

In specific embodiments, the placental cells express CD200 and ARTS1 (aminopeptidase regulator of type 1 tumor necrosis factor); ARTS-1 and LRAP (leukocyte-derived arginine aminopeptidase); IL6 (interleukin-6) and TGFB2 (transforming growth factor, beta 2); IL6 and KRT18 (keratin 18); IER3 (immediate early response 3), MEST (mesoderm specific transcript homolog) and TGFB2; CD200 and IER3; CD200 and IL6; CD200 and KRT18; CD200 and LRAP; CD200 and MEST; CD200 and NFE2L3 (nuclear factor (erythroid-derived 2)-like 3); or CD200 and TGFB2 at a detectably higher level than an equivalent number of bone marrow-derived mesenchymal stem cells (BM-MSCs) wherein said bone marrow-derived mesenchymal stem cells have undergone a number of passages in culture equivalent to the number of passages said isolated placental cells have undergone. In other specific embodiments, the placental cells express ARTS-1, CD200, IL6 and LRAP; ARTS-1, IL6, TGFB2, IER3, KRT18 and MEST; CD200, IER3, IL6, KRT18, LRAP, MEST, NFE2L3, and TGFB2; ARTS-1, CD200, IER3, IL6, KRT18, LRAP, MEST, NFE2L3, and TGFB2; or IER3, MEST and TGFB2 at a detectably higher level than an equivalent number of bone marrow-derived mesenchymal stem cells BM-MSCs, wherein said bone marrow-derived mesenchymal stem cells have undergone a number of passages in culture equivalent to the number of passages said isolated placental cells have undergone.

Expression of the above-referenced genes can be assessed by standard techniques. For example, probes based on the sequence of the gene(s) can be individually selected and constructed by conventional techniques. Expression of the genes can be assessed, e.g., on a microarray comprising probes to one or more of the genes, e.g., an Affymetrix GENECHIP® Human Genome U133A 2.0 array, or an Affymetrix GENECHIP® Human Genome U133 Plus 2.0 (Santa Clara, Calif.). Expression of these genes can be assessed even if the sequence for a particular GenBank accession number is amended because probes specific for the amended sequence can readily be generated using well-known standard techniques.

The level of expression of these genes can be used to confirm the identity of a population of isolated placental cells, to identify a population of cells as comprising at least a plurality of isolated placental cells, or the like. Populations of isolated placental cells, the identity of which is confirmed, can be clonal, e.g., populations of isolated placental cells expanded from a single isolated placental cell, or a mixed population of stem cells, e.g., a population of cells comprising solely isolated placental cells that are expanded from multiple isolated placental cells, or a population of cells comprising isolated placental cells, as described herein, and at least one other type of cell.

The level of expression of these genes can be used to select populations of isolated placental cells. For example, a population of cells, e.g., clonally-expanded cells, may be selected if the expression of one or more of the genes listed above is significantly higher in a sample from the population of cells than in an equivalent population of mesenchymal stem cells. Such selecting can be of a population from a plurality of isolated placental cell populations, from a plurality of cell populations, the identity of which is not known, etc.

Isolated placental cells can be selected on the basis of the level of expression of one or more such genes as compared to the level of expression in said one or more genes in, e.g., a mesenchymal stem cell control, for example, the level of expression in said one or more genes in an equivalent number of bone marrow-derived mesenchymal stem cells. In one embodiment, the level of expression of said one or more genes in a sample comprising an equivalent number of mesenchymal stem cells is used as a control. In another embodiment, the control, for isolated placental cells tested under certain conditions, is a numeric value representing the level of expression of said one or more genes in mesenchymal stem cells under said conditions.

The isolated placental cells described herein display the above characteristics (e.g., combinations of cell surface markers and/or gene expression profiles) in primary culture, or during proliferation in medium comprising, e.g., DMEM-LG (Gibco), 2% fetal calf serum (FCS) (Hyclone Laboratories), 1× insulin-transferrin-selenium (ITS), 1× lenolenic-acid-bovine-serum-albumin (LA-BSA), $10^{-9}$M dexamethasone (Sigma), $10^{-4}$M ascorbic acid 2-phosphate (Sigma), epidermal growth factor (EGF) 10 ng/ml (R&D Systems), platelet derived-growth factor (PDGF-BB) 10 ng/ml (R&D Systems), and 100 U penicillin/1000 U streptomycin.

In certain embodiments of any of the placental cells disclosed herein, the cells are human. In certain embodiments of any of the placental cells disclosed herein, the cellular marker characteristics or gene expression characteristics are human markers or human genes.

In another specific embodiment of said isolated placental cells or populations of cells comprising the isolated placental cells, said cells or population have been expanded, for example, passaged at least, about, or no more than, 1, 2, 3, 4, 5, 6, 7, 8, 9, 10, 11, 12, 13, 14, 15, 16, 17, 18, 19, or 20 times, or proliferated for at least, about, or no more than, 1, 2, 3, 4, 5, 6, 7, 8, 9, 10, 12, 14, 16, 18, 20, 22, 24, 26, 28, 30, 32, 34, 36, 38 or 40 population doublings. In another specific embodiment of said isolated placental cells or populations of cells comprising the isolated placental cells, said cells or population are primary isolates. In another specific embodiment of the isolated placental cells, or populations of cells comprising isolated placental cells, that are disclosed herein, said isolated placental cells are fetal in origin (that is, have the fetal genotype).

In certain embodiments, said isolated placental cells do not differentiate during culturing in growth medium, i.e., medium formulated to promote proliferation, e.g., during proliferation in growth medium. In another specific embodiment, said isolated placental cells do not require a feeder layer in order to proliferate. In another specific embodiment, said isolated placental cells do not differentiate in culture in the absence of a feeder layer, solely because of the lack of a feeder cell layer.

In another embodiment, cells useful in the methods and compositions described herein are isolated placental cells, wherein a plurality of said isolated placental cells are positive for aldehyde dehydrogenase (ALDH), as assessed by an aldehyde dehydrogenase activity assay. Such assays are known in the art (see, e.g., Bostian and Betts, *Biochem. J.*, 173, 787, (1978)). In a specific embodiment, said ALDH assay uses ALDEFLUOR® (Aldagen, Inc., Ashland, Oreg.) as a marker of aldehyde dehydrogenase activity. In a specific embodiment, said plurality is between about 3% and about 25% of cells in said population of cells. In another embodiment, provided herein is a population of isolated umbilical cord cells, e.g., multipotent isolated umbilical cord cells, wherein a plurality of said isolated umbilical cord cells are positive for aldehyde dehydrogenase, as assessed by an aldehyde dehydrogenase activity assay that uses ALDEFLUOR® as an indicator of aldehyde dehydrogenase activity. In a specific embodiment, said plurality is between about 3% and about 25% of cells in said population of cells. In another embodiment, said population of isolated placental cells or isolated umbilical cord cells shows at least three-fold, or at least five-fold, higher ALDH activity than a population of bone marrow-derived mesenchymal stem cells having about the same number of cells and cultured under the same conditions.

In certain embodiments of any of the populations of cells comprising the isolated placental cells described herein, the placental cells in said populations of cells are substantially free of cells having a maternal genotype; e.g., at least 40%, 45%, 50%, 55%, 60%, 65%, 70%, 75%, 80%, 85%, 90%, 95%, 98% or 99% of the placental cells in said population have a fetal genotype. In certain other embodiments of any of the populations of cells comprising the isolated placental cells described herein, the populations of cells comprising said placental cells are substantially free of cells having a maternal genotype; e.g., at least 40%, 45%, 50%, 55%, 60%, 65%, 70%, 75%, 80%, 85%, 90%, 95%, 98% or 99% of the cells in said population have a fetal genotype.

In a specific embodiment of any of the above isolated placental cells or cell populations of isolated placental cells, the karyotype of the cells, or at least about 95% or about 99% of the cells in said population, is normal. In another specific embodiment of any of the above placental cells or cell populations, the cells, or cells in the population of cells, are non-maternal in origin.

Isolated placental cells, or populations of isolated placental cells, bearing any of the above combinations of markers, can be combined in any ratio. Any two or more of the above isolated placental cell populations can be combined to form an isolated placental cell population. For example, an population of isolated placental cells can comprise a first population of isolated placental cells defined by one of the marker combinations described above, and a second population of isolated placental cells defined by another of the marker combinations described above, wherein said first and second populations are combined in a ratio of about 1:99, 2:98, 3:97, 4:96, 5:95, 10:90, 20:80, 30:70, 40:60, 50:50, 60:40, 70:30, 80:20, 90:10, 95:5, 96:4, 97:3, 98:2, or about 99:1. In like fashion, any three, four, five or more of the above-described isolated placental cells or isolated placental cells populations can be combined.

Isolated placental cells useful in the methods and compositions described herein can be obtained, e.g., by disruption of placental tissue, with or without enzymatic digestion (see Section 4.3.3) or perfusion (see Section 4.3.4). For example, populations of isolated placental cells can be produced according to a method comprising perfusing a mammalian placenta that has been drained of cord blood and perfused to remove residual blood; perfusing said placenta with a perfusion solution; and collecting said perfusion solution, wherein said perfusion solution after perfusion comprises a population of placental cells that comprises isolated placental cells; and isolating a plurality of said isolated placental cells from said population of cells. In a specific embodiment, the perfusion solution is passed through both the umbilical vein and umbilical arteries and collected after it exudes from the placenta. In another specific embodiment, the perfusion solution is passed through the umbilical vein and collected from the umbilical arteries, or passed through the umbilical arteries and collected from the umbilical vein.

In various embodiments, the isolated placental cells, contained within a population of cells obtained from perfusion of a placenta, are at least 50%, 60%, 70%, 80%, 90%, 95%, 99% or at least 99.5% of said population of placental cells. In another specific embodiment, the isolated placental cells collected by perfusion comprise fetal and maternal cells. In another specific embodiment, the isolated placental cells collected by perfusion are at least 50%, 60%, 70%, 80%, 90%, 95%, 99% or at least 99.5% fetal cells.

In another specific embodiment, provided herein is a composition comprising a population of the isolated placental cells, as described herein, collected by perfusion, wherein said composition comprises at least a portion of the perfusion solution used to collect the isolated placental cells.

Isolated populations of the isolated placental cells described herein can be produced by digesting placental tissue with a tissue-disrupting enzyme to obtain a population of placental cells comprising the cells, and isolating, or substantially isolating, a plurality of the placental cells from the remainder of said placental cells. The whole, or any part of, the placenta can be digested to obtain the isolated placental cells described herein. In specific embodiments, for example, said placental tissue can be a whole placenta, an amniotic membrane, chorion, a combination of amnion and chorion, or a combination of any of the foregoing. In other specific embodiment, the tissue-disrupting enzyme is trypsin or collagenase. In various embodiments, the isolated placental cells, contained within a population of cells obtained from digesting a placenta, are at least 50%, 60%, 70%, 80%, 90%, 95%, 99% or at least 99.5% of said population of placental cells.

The isolated populations of placental cells described above, and populations of isolated placental cells generally, can comprise about, at least, or no more than, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, $1\times10^{11}$ or more of the isolated placental cells. Populations of isolated placental cells useful in the methods of treatment described herein comprise at least 50%, 55%, 60%, 65%, 70%, 75%, 80%, 85%, 90%, 95%, 98%, or 99% viable isolated placental cells, e.g., as determined by, e.g., trypan blue exclusion

4.2.3 Growth in Culture

The growth of the isolated placental cells described herein in Section 4.4.2, as for any mammalian cell, depends in part upon the particular medium selected for growth. Under optimum conditions, the isolated placental cells typically double in number in about 1 day. During culture, the isolated placental cells described herein adhere to a substrate in culture, e.g. the surface of a tissue culture container (e.g., tissue culture dish plastic, fibronectin-coated plastic, and the like) and form a monolayer.

Populations of placental cells that comprise the isolated placental cells described herein, when cultured under appropriate conditions, can form embryoid-like bodies, that is, three-dimensional clusters of cells grow atop the adherent cell layer. Cells within the embryoid-like bodies can express markers associated with very early stem cells, e.g., OCT-4, Nanog, SSEA3 and SSEA4. Cells within the embryoid-like bodies are typically not adherent to the culture substrate, as are the isolated placental cells described herein, but tend to remain attached to the adherent cells during culture. Embryoid-like body cells are dependent upon the adherent isolated placental cells for viability, as embryoid-like bodies do not form in the absence of the adherent isolated placental cells. The adherent isolated placental cells thus facilitate the growth of one or more embryoid-like bodies in a population of placental cells that comprise the adherent isolated placental cells. Without wishing to be bound by theory, the cells of the embryoid-like bodies are thought to grow on the adherent isolated placental cells much as embryonic stem cells grow on a feeder layer of cells.

4.3 Methods of Obtaining Isolated Placental Cells
4.3.1 Stem Cell Collection Composition Further provided herein are methods of collecting and isolating placental cells, e.g., the isolated placental cells described in Section 4.2.2, above. Generally, such cells are obtained from a mammalian placenta using a physiologically-acceptable solution, e.g., a cell collection composition. An exemplary cell collection composition is described in detail in related U.S. Patent Application Publication No. 2007/0190042, entitled "Improved Medium for Collecting Placental Stem Cells and Preserving Organs," the disclosure of which is incorporated herein by reference in its entirety The cell collection composition can comprise any physiologically-acceptable solution suitable for the collection and/or culture of cells, e.g., the isolated placental cells described herein, for example, a saline solution (e.g., phosphate-buffered saline, Kreb's solution, modified Kreb's solution, Eagle's solution, 0.9% NaCl. etc.), a culture medium (e.g., DMEM, H.DMEM, etc.), and the like.

The cell collection composition can comprise one or more components that tend to preserve isolated placental cells, that is, prevent the isolated placental cells from dying, or delay the death of the isolated placental cells, reduce the number of isolated placental cells in a population of cells that die, or the like, from the time of collection to the time of culturing. Such components can be, e.g., an apoptosis inhibitor (e.g., a caspase inhibitor or JNK inhibitor); a vasodilator (e.g., magnesium sulfate, an antihypertensive drug, atrial natriuretic peptide (ANP), adrenocorticotropin, corticotropin-releasing hormone, sodium nitroprusside, hydralazine, adenosine triphosphate, adenosine, indomethacin or magnesium sulfate, a phosphodiesterase inhibitor, etc.); a necrosis inhibitor (e.g., 2-(1H-Indol-3-yl)-3-pentylamino-maleimide, pyrrolidine dithiocarbamate, or clonazepam); a TNF-α inhibitor; and/or an oxygen-carrying perfluorocarbon (e.g., perfluorooctyl bromide, perfluorodecyl bromide, etc.).

The cell collection composition can comprise one or more tissue-degrading enzymes, e.g., a metalloprotease, a serine protease, a neutral protease, an RNase, or a DNase, or the like. Such enzymes include, but are not limited to, collagenases (e.g., collagenase I, II, III or IV, a collagenase from *Clostridium histolyticum*, etc.); dispase, thermolysin, elastase, trypsin, LIBERASE, hyaluronidase, and the like.

The cell collection composition can comprise a bacteriocidally or bacteriostatically effective amount of an antibiotic. In certain non-limiting embodiments, the antibiotic is a macrolide (e.g., tobramycin), a cephalosporin (e.g., cephalexin, cephradine, cefuroxime, cefprozil, cefaclor, cefixime or cefadroxil), a clarithromycin, an erythromycin, a penicillin (e.g., penicillin V) or a quinolone (e.g., ofloxacin, ciprofloxacin or norfloxacin), a tetracycline, a streptomycin, etc. In a particular embodiment, the antibiotic is active against Gram (+) and/or Gram(−) bacteria, e.g., *Pseudomonas aeruginosa, Staphylococcus aureus*, and the like. In one embodiment, the antibiotic is gentamycin, e.g., about 0.005% to about 0.01% (w/v) in culture medium The cell collection composition can also comprise one or more of the following compounds: adenosine (about 1 mM to about 50 mM); D-glucose (about 20 mM to about 100 mM); magnesium ions (about 1 mM to about 50 mM); a macromolecule of molecular weight greater than 20,000 daltons, in one embodiment, present in an amount sufficient to maintain endothelial integrity and cellular viability (e.g., a synthetic or naturally occurring colloid, a polysaccharide such as dextran or a polyethylene glycol present at about 25 g/l to about 100 g/l, or about 40 g/l to about 60 g/l); an antioxidant (e.g., butylated hydroxyanisole, butylated hydroxytoluene, glutathione, vitamin C or vitamin E present at about 25 μM to about 100 μM); a reducing agent (e.g., N-acetylcysteine present at about 0.1 mM to about 5 mM); an agent that prevents calcium entry into cells (e.g., verapamil present at about 2 μM to about 25 μM); nitroglycerin (e.g., about 0.05 g/L to about 0.2 g/L); an anticoagulant, in one embodiment, present in an amount sufficient to help prevent clotting of residual blood (e.g., heparin or hirudin present at a concentration of about 1000 units/l to about 100,000 units/l); or an amiloride containing compound (e.g., amiloride, ethyl isopropyl amiloride, hexamethylene amiloride, dimethyl amiloride or isobutyl amiloride present at about 1.0 μM to about 5 μM).

4.3.2 Collection and Handling of Placenta

Generally, a human placenta is recovered shortly after its expulsion after birth. In a preferred embodiment, the placenta is recovered from a patient after informed consent and after a complete medical history of the patient is taken and is associated with the placenta. Preferably, the medical history continues after delivery. Such a medical history can be used to coordinate subsequent use of the placenta or the isolated placental cells harvested therefrom. For example, isolated human placental cells can be used, in light of the medical history, for personalized medicine for the infant associated with the placenta, or for parents, siblings or other relatives of the infant.

Prior to recovery of isolated placental cells, the umbilical cord blood and placental blood are preferably removed. In certain embodiments, after delivery, the cord blood in the placenta is recovered. The placenta can be subjected to a conventional cord blood recovery process. Typically a needle or cannula is used, with the aid of gravity, to exsanguinate the placenta (see, e.g., Anderson, U.S. Pat. No. 5,372,581; Hessel et al., U.S. Pat. No. 5,415,665). The needle or cannula is usually placed in the umbilical vein and the placenta can be gently massaged to aid in draining cord blood from the placenta. Such cord blood recovery may be performed commercially, e.g., LifeBank USA, Cedar Knolls, N.J. Preferably, the placenta is gravity drained without further manipulation so as to minimize tissue disruption during cord blood recovery.

Typically, a placenta is transported from the delivery or birthing room to another location, e.g., a laboratory, for recovery of cord blood and collection of stem cells by, e.g., perfusion or tissue dissociation. The placenta is preferably transported in a sterile, thermally insulated transport device (maintaining the temperature of the placenta between 20-28° C.), for example, by placing the placenta, with clamped proximal umbilical cord, in a sterile zip-lock plastic bag, which is then placed in an insulated container. In another embodiment, the placenta is transported in a cord blood collection kit substantially as described in pending U.S. Pat. No. 7,147,626, the disclosure of which is incorporated by reference herein. Preferably, the placenta is delivered to the laboratory four to twenty-four hours following delivery. In certain embodiments, the proximal umbilical cord is clamped, preferably within 4-5 cm (centimeter) of the insertion into the placental disc prior to cord blood recovery. In other embodiments, the proximal umbilical cord is clamped after cord blood recovery but prior to further processing of the placenta.

The placenta, prior to cell collection, can be stored under sterile conditions and at either room temperature or at a temperature of 5° C. to 25° C. The placenta may be stored for a period of for a period of four to twenty-four hours, up to forty-eight hours, or longer than forty eight hours, prior to perfusing the placenta to remove any residual cord blood. In one embodiment, the placenta is harvested from between about zero hours to about two hours post-expulsion. The placenta is preferably stored in an anticoagulant solution at a temperature of 5° C. to 25° C. Suitable anticoagulant solutions are well known in the art. For example, a solution of heparin or warfarin sodium can be used. In a preferred embodiment, the anticoagulant solution comprises a solution of heparin (e.g., 1% w/w in 1:1000 solution). The exsanguinated placenta is preferably stored for no more than 36 hours before placental cells are collected.

The mammalian placenta or a part thereof, once collected and prepared generally as above, can be treated in any art-known manner, e.g., can be perfused or disrupted, e.g., digested with one or more tissue-disrupting enzymes, to obtain isolated placental cells.

4.3.3 Physical Disruption and Enzymatic Digestion of Placental Tissue

In one embodiment, stem cells are collected from a mammalian placenta by physical disruption of part of all of the organ. For example, the placenta, or a portion thereof, may be, e.g., crushed, sheared, minced, diced, chopped, macerated or the like. The tissue can then be cultured to obtain a population of isolated placental cells. Typically, the placental tissue is disrupted using, e.g., culture medium, a saline solution, or a stem cell collection composition (see Section 4.5.1 and below).

The placenta can be dissected into components prior to physical disruption and/or enzymatic digestion and stem cell recovery. Isolated placental cells can be obtained from all or a portion of the amniotic membrane, chorion, umbilical cord, placental cotyledons, or any combination thereof, including from a whole placenta. Preferably, isolated placental cells are obtained from placental tissue comprising amnion and chorion. Typically, isolated placental cells can be obtained by disruption of a small block of placental tissue, e.g., a block of placental tissue that is about 1, 2, 3, 4, 5, 6, 7, 8, 9, 10, 20, 30, 40, 50, 60, 70, 80, 90, 100, 200, 300, 400, 500, 600, 700, 800, 900 or about 1000 cubic millimeters in volume. Any method of physical disruption can be used, provided that the method of disruption leaves a plurality, more preferably a majority, and more preferably at least 60%, 70%, 80%, 90%, 95%, 98%, or 99% of the cells in said organ viable, as determined by, e.g., trypan blue exclusion.

The isolated adherent placental cells can generally be collected from a placenta, or portion thereof, at any time within about the first three days post-expulsion, but preferably between about 8 hours and about 18 hours post-expulsion.

In a specific embodiment, the disrupted tissue is cultured in tissue culture medium suitable for the proliferation of isolated placental cells (see, e.g., Section 4.6, below, describing the culture of placental cells, e.g., PDACs).

In another specific embodiment, isolated placental cells are collected by physical disruption of placental tissue, wherein the physical disruption includes enzymatic digestion, which can be accomplished by use of one or more tissue-digesting enzymes. The placenta, or a portion thereof, may also be physically disrupted and digested with one or more enzymes, and the resulting material then immersed in, or mixed into, a cell collection composition.

A preferred cell collection composition comprises one or more tissue-disruptive enzyme(s). Enzymes that can be used to disrupt placenta tissue include papain, deoxyribonucleases, serine proteases, such as trypsin, chymotrypsin, collagenase, dispase or elastase. Serine proteases may be inhibited by alpha 2 microglobulin in serum and therefore the medium used for digestion is usually serum-free. EDTA and DNase are commonly used in enzyme digestion procedures to increase the efficiency of cell recovery. The digestate is preferably diluted so as to avoid trapping cells within the viscous digest.

Any combination of tissue digestion enzymes can be used. Typical concentrations for digestion using trypsin include, 0.1% to about 2% trypsin, e.g,. about 0.25% trypsin. Proteases can be used in combination, that is, two or more proteases in the same digestion reaction, or can be used sequentially in order to liberate placental cells, e.g., placental stem cells and placental multipotent cells. For example, in one embodiment, a placenta, or part thereof, is digested first with an appropriate amount of collagenase I at about 1 to about 2 mg/ml for, e.g., 30 minutes, followed by digestion with trypsin, at a concentration of about 0.25%, for, e.g., 10 minutes, at 37° C. Serine proteases are preferably used consecutively following use of other enzymes.

In another embodiment, the tissue can further be disrupted by the addition of a chelator, e.g., ethylene glycol bis(2-aminoethyl ether)-N,N,N'N'-tetraacetic acid (EGTA) or ethylenediaminetetraacetic acid (EDTA) to the stem cell collection composition comprising the stem cells, or to a solution in which the tissue is disrupted and/or digested prior to isolation of the stem cells with the stem cell collection composition.

Following digestion, the digestate is washed, for example, three times with culture medium, and the washed cells are seeded into culture flasks. The cells are then isolated by differential adherence, and characterized for, e.g., viability, cell surface markers, differentiation, and the like.

It will be appreciated that where an entire placenta, or portion of a placenta comprising both fetal and maternal cells (for example, where the portion of the placenta comprises the chorion or cotyledons), the placental cells isolated can comprise a mix of placental cells derived from both fetal and maternal sources. Where a portion of the placenta that comprises no, or a negligible number of, maternal cells (for example, amnion), the placental cells isolated therefrom will comprise almost exclusively fetal placental cells (that is, placental cells having the genotype of the fetus).

Placental cells, e.g., the placental cells described in Section 4.2.2, above, can be isolated from disrupted placental tissue by differential trypsinization (see Section 4.3.5, below) followed by culture in one or more new culture containers in fresh proliferation medium, optionally followed by a second differential trypsinization step.

4.3.4 Placental Perfusion

Placental cells, e.g., the placental cells described in Section 4.2.2, above, can also be obtained by perfusion of the mammalian placenta. Methods of perfusing mammalian placenta to obtain placental cells are disclosed, e.g., in Hariri, U.S. Pat. Nos. 7,045,148 and 7,255,729, in U.S. Patent Application Publication Nos. 2007/0275362 and 2007/0190042, the disclosures of each of which are incorporated herein by reference in their entireties.

Placental cells can be collected by perfusion, e.g., through the placental vasculature, using, e.g., a cell collection composition as a perfusion solution. In one embodiment, a mammalian placenta is perfused by passage of perfusion solution through either or both of the umbilical artery and umbilical vein. The flow of perfusion solution through the placenta may be accomplished using, e.g., gravity flow into the placenta. Preferably, the perfusion solution is forced through the placenta using a pump, e.g., a peristaltic pump. The umbilical vein can be, e.g., cannulated with a cannula, e.g., a TEFLON® or plastic cannula, that is connected to a sterile connection apparatus, such as sterile tubing. The sterile connection apparatus is connected to a perfusion manifold.

In preparation for perfusion, the placenta is preferably oriented (e.g., suspended) in such a manner that the umbilical artery and umbilical vein are located at the highest point of the placenta. The placenta can be perfused by passage of a perfusion fluid through the placental vasculature and surrounding tissue. The placenta can also be perfused by passage of a perfusion fluid into the umbilical vein and collection from the umbilical arteries, or passage of a perfusion fluid into the umbilical arteries and collection from the umbilical vein.

In one embodiment, for example, the umbilical artery and the umbilical vein are connected simultaneously, e.g., to a pipette that is connected via a flexible connector to a reservoir of the perfusion solution. The perfusion solution is passed into the umbilical vein and artery. The perfusion solution exudes from and/or passes through the walls of the blood vessels into the surrounding tissues of the placenta, and is collected in a suitable open vessel from the surface of the placenta that was attached to the uterus of the mother during gestation. The perfusion solution may also be introduced through the umbilical cord opening and allowed to flow or percolate out of openings in the wall of the placenta which interfaced with the maternal uterine wall. Placental cells that are collected by this method, which can be referred to as a "pan" method, are typically a mixture of fetal and maternal cells.

In another embodiment, the perfusion solution is passed through the umbilical veins and collected from the umbilical artery, or is passed through the umbilical artery and collected from the umbilical veins. Placental cells collected by this method, which can be referred to as a "closed circuit" method, are typically almost exclusively fetal.

It will be appreciated that perfusion using the pan method, that is, whereby perfusate is collected after it has exuded from the maternal side of the placenta, results in a mix of fetal and maternal cells. As a result, the cells collected by this method can comprise a mixed population of placental cells, e.g., placental stem cells or placental multipotent cells, of both fetal and maternal origin. In contrast, perfusion solely through the placental vasculature in the closed circuit method, whereby perfusion fluid is passed through one or two placental vessels and is collected solely through the remaining vessel(s), results in the collection of a population of placental cells almost exclusively of fetal origin.

The closed circuit perfusion method can, in one embodiment, be performed as follows. A post-partum placenta is obtained within about 48 hours after birth. The umbilical cord is clamped and cut above the clamp. The umbilical cord can be discarded, or can processed to recover, e.g., umbilical cord stem cells, and/or to process the umbilical cord membrane for the production of a biomaterial. The amniotic membrane can be retained during perfusion, or can be separated from the chorion, e.g., using blunt dissection with the fingers. If the amniotic membrane is separated from the chorion prior to perfusion, it can be, e.g., discarded, or processed, e.g., to obtain stem cells by enzymatic digestion, or to produce, e.g., an amniotic membrane biomaterial, e.g., the biomaterial described in U.S. Application Publication No. 2004/0048796, the disclosure of which is incorporated by reference herein in its entirety. After cleaning the placenta of all visible blood clots and residual blood, e.g., using sterile gauze, the umbilical cord vessels are exposed, e.g., by partially cutting the umbilical cord membrane to expose a cross-section of the cord. The vessels are identified, and opened, e.g., by advancing a closed alligator clamp through the cut end of each vessel. The apparatus, e.g., plastic tubing connected to a perfusion device or peristaltic pump, is then inserted into each of the placental arteries. The pump can be any pump suitable for the purpose, e.g., a peristaltic pump. Plastic tubing, connected to a sterile collection reservoir, e.g., a blood bag such as a 250 mL collection bag, is then inserted into the placental vein. Alternatively, the tubing connected to the pump is inserted into the placental vein, and tubes to a collection reservoir(s) are inserted into one or both of the placental arteries. The placenta is then perfused with a volume of perfusion solution, e.g., about 750 ml of perfusion solution. Cells in the perfusate are then collected, e.g., by centrifugation. In certain embodiments, the placenta is perfused with perfusion solution, e.g., 100-300 mL perfusion solution, to remove residual blood prior to perfusion to collect placental cells, e.g., placental stem cells and/or placental multipotent cells. In another embodiment, the placenta is not perfused with perfusion solution to remove residual blood prior to perfusion to collect placental cells.

In one embodiment, the proximal umbilical cord is clamped during perfusion, and more preferably, is clamped within 4-5 cm (centimeter) of the cord's insertion into the placental disc.

The first collection of perfusion fluid from a mammalian placenta during the exsanguination process is generally colored with residual red blood cells of the cord blood and/or placental blood. The perfusion fluid becomes more colorless as perfusion proceeds and the residual cord blood cells are washed out of the placenta. Generally from 30 to 100 ml (milliliter) of perfusion fluid is adequate to initially exsanguinate the placenta, but more or less perfusion fluid may be used depending on the observed results.

The volume of perfusion liquid used to isolate placental cells may vary depending upon the number of cells to be collected, the size of the placenta, the number of collections to be made from a single placenta, etc. In various embodiments, the volume of perfusion liquid may be from 50 mL to 5000 mL, 50 mL to 4000 mL, 50 mL to 3000 mL, 100 mL to 2000 mL, 250 mL to 2000 mL, 500 mL to 2000 mL, or 750 mL to 2000 mL. Typically, the placenta is perfused with 700-800 mL of perfusion liquid following exsanguination.

The placenta can be perfused a plurality of times over the course of several hours or several days. Where the placenta is to be perfused a plurality of times, it may be maintained or cultured under aseptic conditions in a container or other suitable vessel, and perfused with the cell collection composition, or a standard perfusion solution (e.g., a normal saline solution such as phosphate buffered saline ("PBS")) with or without an anticoagulant (e.g., heparin, warfarin sodium, coumarin, bishydroxycoumarin), and/or with or without an antimicrobial agent (e.g., β-mercaptoethanol (0.1 mM); antibiotics such as streptomycin (e.g., at 40-100 μg/ml), penicillin (e.g., at 40 U/ml), amphotericin B (e.g., at 0.5 μg/ml). In one embodiment, an isolated placenta is maintained or cultured for a period of time without collecting the perfusate, such that the placenta is maintained or cultured for 1, 2, 3, 4, 5, 6, 7, 8, 9, 10, 11, 12, 13, 14, 15, 16, 17, 18, 19, 20, 21, 22, 23, or 24 hours, or 2 or 3 or more days before perfusion and collection of perfusate. The perfused placenta can be maintained for one or more additional time(s), e.g., 1, 2, 3, 4, 5, 6, 7, 8, 9, 10, 11, 12, 13, 14, 15, 16, 17, 18, 19, 20, 21, 22, 23, 24 or more hours, and perfused a second time with, e.g., 700-800 mL perfusion fluid. The placenta can be perfused 1, 2, 3, 4, 5 or more times, for example, once every 1, 2, 3, 4, 5 or 6 hours. In a preferred embodiment, perfusion of the placenta and collection of perfusion solution, e.g., cell collection composition, is repeated until the number of recovered nucleated cells falls below 100 cells/ml. The perfusates at different time points can be further processed individually to recover time-dependent populations of cells, e.g., stem cells. Perfusates from different time points can also be pooled. In a preferred embodiment, placental cells are collected at a time or times between about 8 hours and about 18 hours post-expulsion.

Perfusion preferably results in the collection of significantly more placental cells than the number obtainable from a mammalian placenta not perfused with said solution, and not otherwise treated to obtain placental cells (e.g., by tissue disruption, e.g., enzymatic digestion). In this context, "significantly more" means at least 10% more. Perfusion yields significantly more placental cells than, e.g., the number of placental cells isolatable from culture medium in which a placenta, or portion thereof, has been cultured.

Placental cells can be isolated from placenta by perfusion with a solution comprising one or more proteases or other tissue-disruptive enzymes. In a specific embodiment, a placenta or portion thereof (e.g., amniotic membrane, amnion and chorion, placental lobule or cotyledon, umbilical cord, or combination of any of the foregoing) is brought to 25-37° C., and is incubated with one or more tissue-disruptive enzymes in 200 mL of a culture medium for 30 minutes. Cells from the perfusate are collected, brought to 4° C., and washed with a cold inhibitor mix comprising 5 mM EDTA, 2 mM dithiothreitol and 2 mM beta-mercaptoethanol. The placental cells are washed after several minutes with a cold (e.g., 4° C.) stem cell collection composition.

4.3.5 Isolation, Sorting, and Characterization of Placental Cells

The isolated placental cells, e.g., the cells described in Section 4.2.2, above, whether obtained by perfusion or physical disruption, e.g., by enzymatic digestion, can initially be purified from (i.e., be isolated from) other cells by Ficoll gradient centrifugation. Such centrifugation can follow any standard protocol for centrifugation speed, etc. In one embodiment, for example, cells collected from the placenta are recovered from perfusate by centrifugation at 5000×g for 15 minutes at room temperature, which separates cells from, e.g., contaminating debris and platelets. In another embodiment, placental perfusate is concentrated to about 200 ml, gently layered over Ficoll, and centrifuged at about 1100×g for 20 minutes at 22° C., and the low-density interface layer of cells is collected for further processing.

Cell pellets can be resuspended in fresh stem cell collection composition, or a medium suitable for cell maintenance, e.g., stem cell maintenance, for example, IMDM serum-free medium containing 2 U/ml heparin and 2 mM EDTA (GibcoBRL, NY). The total mononuclear cell fraction can be isolated, e.g., using Lymphoprep (Nycomed Pharma, Oslo, Norway) according to the manufacturer's recommended procedure.

Placental cells obtained by perfusion or digestion can, for example, be further, or initially, isolated by differential trypsinization using, e.g., a solution of 0.05% trypsin with 0.2% EDTA (Sigma, St. Louis Mo.). Differential trypsinization is possible because the isolated placental cells, which are tissue culture plastic-adherent, typically detach from the plastic surfaces within about five minutes whereas other adherent populations typically require more than 20-30 minutes incubation. The detached placental cells can be harvested following trypsinization and trypsin neutralization, using, e.g., Trypsin Neutralizing Solution (TNS, Cambrex). In one embodiment of isolation of adherent cells, aliquots of, for example, about 5-10×10$^6$ cells are placed in each of several T-75 flasks, preferably fibronectin-coated T75 flasks. In such an embodiment, the cells can be cultured with commercially available Mesenchymal Stem Cell Growth Medium (MSCGM) (Cambrex), and placed in a tissue culture incubator (37° C., 5% $CO_2$). After 10 to 15 days, non-adherent cells are removed from the flasks by washing with PBS. The PBS is then replaced by MSCGM. Flasks are preferably examined daily for the presence of various adherent cell types and in particular, for identification and expansion of clusters of fibroblastoid cells.

The number and type of cells collected from a mammalian placenta can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. For example, using antibodies to CD34, one can determine, using the techniques above, whether a cell comprises a detectable amount of CD34; if so, the cell is $CD34^+$. Likewise, if a cell produces enough OCT-4 RNA to be detectable by RT-PCR, or significantly more OCT-4 RNA than an adult cell, the cell is $OCT-4^+$. Antibodies to cell surface markers (e.g., CD markers such as CD34) and the sequence of stem cell-specific genes, such as OCT-4, are well-known in the art.

Placental cells, particularly cells that have been isolated by Ficoll separation, differential adherence, or a combination of both, may be sorted using a fluorescence activated cell sorter (FACS). Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In one sorting scheme, cells from placenta, e.g., PDACs are sorted on the basis of expression of one or more of the markers CD34, CD38, CD44, CD45, , CD73, CD105, OCT-4 and/or HLA-G. This can be accomplished in connection with procedures to select such cells on the basis of their adherence properties in culture. For example, tissue culture plastic adherence selection can be accomplished before or after sorting on the basis of marker expression. In one embodiment, for example, cells are sorted first on the basis of their expression of CD34; $CD34^-$ cells are retained, and $CD34^-$ cells that are additionally $CD200^+$ and $HLA-G^-$ are separated from all other $CD34^-$ cells. In another embodiment, cells from placenta are sorted based on their expression of markers CD200 and/or HLA-G; for example, cells displaying CD200 and lacking HLA-G are isolated for further use. Cells that express, e.g., CD200 and/or lack, e.g., HLA-G can, in a specific embodiment, be further sorted based on their expression of CD73 and/or CD105, or epitopes recognized by antibodies SH2, SH3 or SH4, or lack of expression of CD34, CD38 or CD45. For example, in another embodiment, placental cells are sorted by expression, or lack thereof, of CD200, HLA-G, CD73, CD105, CD34, CD38 and CD45, and placental cells that are $CD200^+$, $HLA-G^-$, $CD73^+$, $CD105^+$, $CD34^-$, $CD38^-$ and $CD45^-$ are isolated from other placental cells for further use.

In specific embodiments of any of the above embodiments of sorted placental cells, at least 50%, 60%, 70%, 80%, 90% or 95% of the cells in a cell population remaining after sorting are said isolated placental cells. Placental cells can be sorted by one or more of any of the markers described in Section 4.2.2, above.

In a specific embodiment, for example, placental cells that are (1) adherent to tissue culture plastic, and (2) $CD10^+$, $CD34^-$ and $CD105^+$ are sorted from (i.e., isolated from) other placental cells. In another specific embodiment, placental cells that are (1) adherent to tissue culture plastic, and (2) $CD10^+$, $CD34^-$, $CD105^+$ and $CD200^+$ are sorted from (i.e., isolated from) other placental cells. In another specific embodiment, placental cells that are (1) adherent to tissue culture plastic, and (2) $CD10^+$, $CD34^-$, $CD45^-$, , $CD90^+$, $CD105^+$ and $CD200^+$ are sorted from (i.e., isolated from) other placental cells.

With respect to nucleotide sequence-based detection of placental cells, sequences for the markers listed herein are readily available in publicly-available databases such as GenBank or EMBL.

With respect to antibody-mediated detection and sorting of placental cells, e.g., placental stem cells or placental multipotent cells, any antibody, specific for a particular marker, can be used, in combination with any fluorophore or other label suitable for the detection and sorting of cells (e.g., fluorescence-activated cell sorting). Antibody/fluorophore combinations to specific markers include, but are not limited to, fluorescein isothiocyanate (FITC) conjugated monoclonal antibodies against HLA-G (available from Serotec, Raleigh, N.C.), CD10 (available from BD Immunocytometry Systems, San Jose, Calif.), CD44 (available from BD Biosciences Pharmingen, San Jose, Calif.), and CD105 (available from R&D Systems Inc., Minneapolis, Minn.); phycoerythrin (PE) conjugated monoclonal antibodies against CD44, CD200, CD117, and CD13 (BD Biosciences Pharmingen); phycoerythrin-Cy7 (PE Cy7) conjugated monoclonal antibodies against CD33 and CD10 (BD Biosciences Pharmingen); allophycocyanin (APC) conjugated streptavidin and monoclonal antibodies against $CD38^-$ (BD Biosciences Pharmingen); and Biotinylated CD90 (BD Biosciences Pharmingen). Other antibodies that can be used include, but are not limited to, CD133-APC (Miltenyi), KDR-Biotin (CD309, Abcam), CytokeratinK-Fitc (Sigma or Dako), HLA ABC-Fitc (BD), HLA DR,DQ,DP-PE (BD), β-2-microglobulin-PE (BD), CD80-PE (BD) and CD86-APC (BD). Other antibody/label combinations that can be used include, but are not limited to, CD45-PerCP (peridin chlorophyll protein); CD44-PE; CD19-PE; CD10-F (fluorescein); HLA-G-F and 7-aminoactinomycin-D (7-AAD); HLA-ABC-F; and the like. This list is not exhaustive, and other antibodies from other suppliers are also commercially available.

The isolated placental cells provided herein can be assayed for CD117 or CD133 using, for example, phycoerythrin-Cy5 (PE Cy5) conjugated streptavidin and biotin conjugated monoclonal antibodies against CD117 or CD133; however, using this system, the cells can appear to be positive for CD117 or CD133, respectively, because of a relatively high background.

The isolated placental cells can be labeled with an antibody to a single marker and detected and/sorted. Placental cells can also be simultaneously labeled with multiple antibodies to different markers.

In another embodiment, magnetic beads can be used to separate cells. The cells may be sorted using a magnetic activated cell sorting (MACS) technique, a method for separating particles based on their ability to bind magnetic beads (0.5-100 μm diameter). A variety of useful modifications can be performed on the magnetic microspheres, including covalent addition of antibody that specifically recognizes a particular cell surface molecule or hapten. The beads are then mixed with the cells to allow binding. Cells are then passed through a magnetic field to separate out cells having the specific cell surface marker. In one embodiment, these cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

Isolated placental cells can also be characterized and/or sorted based on cell morphology and growth characteristics. For example, isolated placental cells can be characterized as having, and/or selected on the basis of, e.g., a fibroblastoid appearance in culture. The isolated placental cells can also be characterized as having, and/or be selected, on the basis of their ability to form embryoid-like bodies. In one embodiment, for example, placental cells that are fibroblastoid in shape, express CD73 and CD105, and produce one or more embryoid-like bodies in culture are isolated from other placental cells. In another embodiment, OCT-4$^+$ placental cells that produce one or more embryoid-like bodies in culture are isolated from other placental cells.

In another embodiment, isolated placental cells can be identified and characterized by a colony forming unit assay. Colony forming unit assays are commonly known in the art, such as MESENCULT™ medium (Stem Cell Technologies, Inc., Vancouver British Columbia).

The isolated placental cells can be assessed for viability, proliferation potential, and longevity using standard techniques known in the art, such as trypan blue exclusion assay, fluorescein diacetate uptake assay, propidium iodide uptake assay (to assess viability); and thymidine uptake assay, MTT (3-(4,5-Dimethylthiazol-2-yl)-2,5-diphenyltetrazolium bromide) cell proliferation assay (to assess proliferation). Longevity may be determined by methods well known in the art, such as by determining the maximum number of population doubling in an extended culture.

Isolated placental cells, e.g., the isolated placental cells described in Section 4.2.2, above, can also be separated from other placental cells using other techniques known in the art, e.g., selective growth of desired cells (positive selection), selective destruction of unwanted cells (negative selection); separation based upon differential cell agglutinability in the mixed population as, for example, with soybean agglutinin; freeze-thaw procedures; filtration; conventional and zonal centrifugation; centrifugal elutriation (counter-streaming centrifugation); unit gravity separation; countercurrent distribution; electrophoresis; and the like.

4.4 Culture of Isolated Placental Cells 4.4.1 Culture Media

Isolated placental cells, or populations of isolated placental cells, or cells or placental tissue from which placental cells grow out, can be used to initiate, or seed, cell cultures. Cells are generally transferred to sterile tissue culture vessels either uncoated or coated with extracellular matrix or ligands such as laminin, collagen (e.g., native or denatured), gelatin, fibronectin, ornithine, vitronectin, and extracellular membrane protein (e.g., MATRIGEL® (BD Discovery Labware, Bedford, Mass.)).

Isolated placental cells can be cultured in any medium, and under any conditions, recognized in the art as acceptable for the culture of cells, e.g., stem cells. Preferably, the culture medium comprises serum. The isolated placental cells can be cultured in, for example, DMEM-LG (Dulbecco's Modified Essential Medium, low glucose)/MCDB 201 (chick fibroblast basal medium) containing ITS (insulin-transferrin-selenium), LA+BSA (linoleic acid-bovine serum albumin), dexamethasone L-ascorbic acid, PDGF, EGF, IGF-1, and penicillin/streptomycin; DMEM-HG (high glucose) comprising 10% fetal bovine serum (FBS); DMEM-HG comprising 15% FBS; IMDM (Iscove's modified Dulbecco's medium) comprising 10% FBS, 10% horse serum, and hydrocortisone; M199 comprising 1% to 20% FBS, EGF, and heparin; α-MEM (minimal essential medium) comprising 10% FBS, GLUTAMAX™ and gentamicin; DMEM comprising 10% FBS, GLUTAMAX™ and gentamicin, etc.

Other media in that can be used to culture placental cells include DMEM (high or low glucose), Eagle's basal medium, Ham's F10 medium (F10), Ham's F-12 medium (F12), Iscove's modified Dulbecco's medium, Mesenchymal Stem Cell Growth Medium (MSCGM), Liebovitz's L-15 medium, MCDB, DMEM/F12, RPMI 1640, advanced DMEM (Gibco), DMEM/MCDB201 (Sigma), and CELL-GRO FREE.

The culture medium can be supplemented with one or more components including, for example, serum (e.g., fetal bovine serum (FBS), preferably about 2-15% (v/v); equine (horse) serum (ES); human serum (HS)); beta-mercaptoethanol (BME), preferably about 0.001% (v/v); one or more growth factors, for example, platelet-derived growth factor (PDGF), epidermal growth factor (EGF), basic fibroblast growth factor (bFGF), insulin-like growth factor-1 (IGF-1), leukemia inhibitory factor (LIF), vascular endothelial growth factor (VEGF), and erythropoietin (EPO); amino acids, including L-valine; and one or more antibiotic and/or antimycotic agents to control microbial contamination, such as, for example, penicillin G, streptomycin sulfate, amphotericin B, gentamicin, and nystatin, either alone or in combination.

The isolated placental cells can be cultured in standard tissue culture conditions, e.g., in tissue culture dishes or multiwell plates. The isolated placental cells can also be cultured using a hanging drop method. In this method, isolated placental cells are suspended at about 1×10$^4$ cells per mL in about 5 mL of medium, and one or more drops of the medium are placed on the inside of the lid of a tissue culture container, e.g., a 100 mL Petri dish. The drops can be, e.g., single drops, or multiple drops from, e.g., a multichannel pipetter. The lid is carefully inverted and placed on top of the bottom of the dish, which contains a volume of liquid, e.g., sterile PBS sufficient to maintain the moisture content in the dish atmosphere, and the stem cells are cultured.

In one embodiment, isolated placental cells are cultured in the presence of a compound that acts to maintain an undifferentiated phenotype in the isolated placental cells. In a specific embodiment, the compound is a substituted 3,4-dihydropyridimol[4,5-d]pyrimidine. In another specific embodiment, the compound is a compound having the following chemical structure:

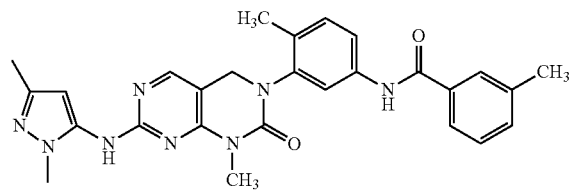

The compound can be contacted with isolated placental cells, or a population of isolated placental cells, at a concentration of, for example, between about 1 μM to about 10 μM.

4.4.2 Expansion and Proliferation of Placental Cells

Once an isolated placental cell, or population of isolated placental cells (e.g., a placental cell or population of placental cells separated from at least 50% of the placental cells with which the stem cell or population of stem cells is normally associated in vivo), the cell or population of cells can be proliferated and expanded in vitro. For example, a population of the isolated placental cells can be cultured in tissue culture containers, e.g., dishes, flasks, multiwell plates, or the like, for a sufficient time for the cells to proliferate to 70-90% confluence, that is, until the cells and their progeny occupy 70-90% of the culturing surface area of the tissue culture container.

The isolated placental cells can be seeded in culture vessels at a density that allows cell growth. For example, the cells may be seeded at low density (e.g., about 1,000 to about 5,000 cells/cm$^2$) to high density (e.g., about 50,000 or more cells/cm$^2$). In a preferred embodiment, the cells are cultured in the presence of about 0 to about 5 percent by volume $CO_2$ in air. In some preferred embodiments, the cells are cultured at about 2 to about 25 percent $O_2$ in air, preferably about 5 to about 20 percent $O_2$ in air. The cells preferably are cultured at about 25° C. to about 40° C., preferably 37° C. The cells are preferably cultured in an incubator. The culture medium can be static or agitated, for example, using a bioreactor. Placental cells, e.g., placental stem cells or placental multipotent cells, preferably are grown under low oxidative stress (e.g., with addition of glutathione, ascorbic acid, catalase, tocopherol, N-acetylcysteine, or the like).

Once confluence of less than 100%, for example, 70% to 90% is obtained, the cells may be passaged. For example, the cells can be enzymatically treated, e.g., trypsinized, using techniques well-known in the art, to separate them from the tissue culture surface. After removing the cells by pipetting and counting the cells, about 10,000-100,000 cells/cm$^2$ are passaged to a new culture container containing fresh culture medium. Typically, the new medium is the same type of medium from which the isolated placental cells were removed. The isolated placental cells can be passaged about, at least, or no more than 1, 2, 3, 4, 5, 6, 7, 8, 9, 10, 12, 14, 16, 18, or 20 times, or more.

4.4.3 Populations of Isolated Placental Cells

Also provided herein are populations of isolated placental cells, e.g., the isolated placental cells described in Section 4.2.2, above, useful in the methods and compositions described herein. Populations of isolated placental cells can be isolated directly from one or more placentas; that is, the cell population can be a population of placental cells comprising the isolated placental cells, wherein the isolated placental cells are obtained from, or contained within, perfusate, or obtained from, or contained within, disrupted placental tissue, e.g., placental tissue digestate (that is, the collection of cells obtained by enzymatic digestion of a placenta or part thereof). The isolated placental cells described herein can also be cultured and expanded to produce populations of the isolated placental cells. Populations of placental cells comprising the isolated placental cells can also be cultured and expanded to produce placental cell populations.

Placental cell populations useful in the methods of treatment provided herein comprise the isolated placental cells, for example, the isolated placental cells as described in Section 4.4.2 herein. In various embodiments, at least 10%, 20%, 30%, 40%, 50%, 60%, 70%, 80%, 90%, 95%, or 99% of the cells in a placental cell population are the isolated placental cells. That is, a population of the isolated placental cells can comprise, e.g., as much as 1%, 5%, 10%, 20%, 30%, 40%, 50%, 60%, 70%, 80%, 90% cells that are not the isolated placental cells.

Isolated placental cell populations useful in the methods and compositions described herein can be produced by, e.g., selecting isolated placental cells, whether derived from enzymatic digestion or perfusion, that express particular markers and/or particular culture or morphological characteristics. In one embodiment, for example, provided herein is a method of producing a cell population by selecting placental cells that (a) adhere to a substrate, and (b) express CD200 and lack expression of HLA-G; and isolating said cells from other cells to form a cell population. In another embodiment, a cell population is produced by selecting placental cells that express CD200 and lack expression of HLA-G, and isolating said cells from other cells to form a cell population. In another embodiment, a cell population is produced by selecting placental cells that (a) adhere to a substrate, and (b) express CD73, CD105, and CD200; and isolating said cells from other cells to form a cell population. In another embodiment, a cell population is produced by identifying placental cells that express CD73, CD105, and CD200, and isolating said cells from other cells to form a cell population. In another embodiment, a cell population is produced by selecting placental cells that (a) adhere to a substrate and (b) express CD200 and OCT-4; and isolating said cells from other cells to form a cell population. In another embodiment, a cell population is produced by selecting placental cells that express CD200 and OCT-4, and isolating said cells from other cells to form a cell population. In another embodiment, a cell population is produced by selecting placental cells that (a) adhere to a substrate, (b) express CD73 and CD105, and (c) facilitate the formation of one or more embryoid-like bodies in a population of placental cells comprising said stem cell when said population is cultured under conditions that allow for the formation of an embryoid-like body; and isolating said cells from other cells to form a cell population. In another embodiment, a cell population is produced by selecting placental cells that express CD73 and CD105, and facilitate the formation of one or more embryoid-like bodies in a population of placental cells comprising said stem cell when said population is cultured under conditions that allow for the formation of an embryoid-like body, and isolating said cells from other cells to form a cell population. In another embodiment, a cell population is produced by selecting placental cells that (a) adhere to a substrate, and (b) express CD73 and CD105, and lack expression of HLA-G; and isolating said cells from other cells to form a cell population. In another embodiment, a cell population is produced by selecting placental cells that express CD73 and CD105 and lack expression of HLA-G, and isolating said cells from other cells to form a cell population. In another embodiment, the method of producing a cell population comprises selecting placental cells that (a) adhere to a substrate, (b) express OCT-4, and (c) facilitate the formation of one or more embryoid-like bodies in a population of placental cells comprising said stem cell when said population is cultured under conditions that allow for the formation of an embryoid-like body; and isolating said cells from other cells to form a cell population. In another embodiment, a cell population is produced by selecting placental cells that express OCT-4, and facilitate the formation of one or more embryoid-like bodies in a population of placental cells comprising said stem cell when said population is cultured under conditions that allow for the formation of an embryoid-like body, and isolating said cells from other cells to form a cell population.

In another embodiment, a cell population is produced by selecting placental cells that (a) adhere to a substrate, and (b) express CD10 and CD105, and do not express CD34; and isolating said cells from other cells to form a cell population. In another embodiment, a cell population is produced by selecting placental cells that express CD10 and CD105, and do not express CD34, and isolating said cells from other cells to form a cell population. In another embodiment, a cell population is produced by selecting placental cells that (a) adhere to a substrate, and (b) express CD10$^+$, CD105, and CD200, and do not express CD34; and isolating said cells from other cells to form a cell population. In another embodiment, a cell population is produced by selecting placental cells that express CD10, CD105, and CD200, and do not express CD34, and isolating said cells from other cells to form a cell population. In another specific embodiment, a cell population is produced by selecting placental cells that (a) adhere to a substrate, and (b) express CD10, CD90, CD105 and CD200, and do not express CD34 and CD45; and isolating said cells from other cells to form a cell population. In another specific embodiment, a cell population is produced by selecting placental cells that express CD10, CD90, CD105 and CD200, and do not express CD34 and CD45, and isolating said cells from other cells to form a cell population.

Selection of cell populations comprising placental cells having any of the marker combinations described in Section 4.2.2, above, can be isolated or obtained in similar fashion.

In any of the above embodiments, selection of the isolated cell populations can additionally comprise selecting placental cells that express ABC-p (a placenta-specific ABC transporter protein; see, e.g., Allikmets et al., *Cancer Res.* 58(23): 5337-9 (1998)). The method can also comprise selecting cells exhibiting at least one characteristic specific to, e.g., a mesenchymal stem cell, for example, expression of CD44, expression of CD90, or expression of a combination of the foregoing.

In the above embodiments, the substrate can be any surface on which culture and/or selection of cells, e.g., isolated placental cells, can be accomplished. Typically, the substrate is plastic, e.g., tissue culture dish or multiwell plate plastic. Tissue culture plastic can be coated with a biomolecule, e.g., laminin or fibronectin.

Cells, e.g., isolated placental cells, can be selected for a placental cell population by any means known in the art of cell selection. For example, cells can be selected using an antibody or antibodies to one or more cell surface markers, for example, in flow cytometry or FACS. Selection can be accomplished using antibodies in conjunction with magnetic beads. Antibodies that are specific for certain stem cell-related markers are known in the art. For example, antibodies to OCT-4 (Abcam, Cambridge, Mass.), CD200 (Abcam), HLA-G (Abcam), CD73 (BD Biosciences Pharmingen, San Diego, Calif.), CD105 (Abcam; BioDesign International, Saco, Me.), etc. Antibodies to other markers are also available commercially, e.g., CD34, CD38 and CD45 are available from, e.g., StemCell Technologies or BioDesign International.

The isolated placental cell populations can comprise placental cells that are not stem cells, or cells that are not placental cells.

The isolated placental cell populations provided herein can be combined with one or more populations of non-stem cells or non-placental cells. For example, a population of isolated placental cells can be combined with blood (e.g., placental blood or umbilical cord blood), blood-derived stem cells (e.g., stem cells derived from placental blood or umbilical cord blood), umbilical cord stem cells, populations of blood-derived nucleated cells, bone marrow-derived mesenchymal cells, bone-derived stem cell populations, crude bone marrow, adult (somatic) stem cells, populations of stem cells contained within tissue, cultured stem cells, populations of fully-differentiated cells (e.g., chondrocytes, fibroblasts, amniotic cells, osteoblasts, muscle cells, cardiac cells, etc.) and the like. In a specific embodiment, a population of cells useful in the methods and compositions described herein comprises isolated placental cells and isolated umbilical cord cells. Cells in an isolated placental cell population can be combined with a plurality of cells of another type in ratios of about 100,000,000:1, 50,000,000:1, 20,000,000:1, 10,000,000:1, 5,000,000:1, 2,000,000:1, 1,000,000:1, 500,000:1, 200,000:1, 100,000:1, 50,000:1, 20,000:1, 10,000:1, 5,000:1, 2,000:1, 1,000:1, 500:1, 200:1, 100:1, 50:1, 20:1, 10:1, 5:1, 2:1, 1:1; 1:2; 1:5; 1:10; 1:100; 1:200; 1:500; 1:1,000; 1:2,000; 1:5,000; 1:10,000; 1:20,000; 1:50,000; 1:100,000; 1:500,000; 1:1,000,000; 1:2,000,000; 1:5,000,000; 1:10,000,000; 1:20,000,000; 1:50,000,000; or about 1:100,000,000, comparing numbers of total nucleated cells in each population. Cells in an isolated placental cell population can be combined with a plurality of cells of a plurality of cell types, as well.

In one embodiment, an isolated population of placental cells is combined with a plurality of hematopoietic stem cells. Such hematopoietic stem cells can be, for example, contained within unprocessed placental, umbilical cord blood or peripheral blood; in total nucleated cells from placental blood, umbilical cord blood or peripheral blood; in an isolated population of CD34$^+$ cells from placental blood, umbilical cord blood or peripheral blood; in unprocessed bone marrow; in total nucleated cells from bone marrow; in an isolated population of CD34$^+$ cells from bone marrow, or the like.

In other embodiments, a population of the placental cells described herein, e.g., the PDACs described in Section 4.2.2, above, are combined with osteogenic placental adherent cells (OPACs), e.g., the OPACs described in patent application Ser. No. 12/546,556, filed Aug. 24, 2009, entitled "Methods and Compositions for Treatment of Bone Defects With Placental Stem Cells," the disclosure of which is hereby incorporated by reference in its entirety.

4.5 Production of a Placental Cell Bank

Isolated cells from postpartum placentas, e.g., the isolated placental cells described in Section 4.2.2, above, can be cultured in a number of different ways to produce a set of lots, e.g., wherein a lot is a set of individually-administrable doses, of isolated placental cells. Such lots can, for example, be obtained from cells from placental perfusate or from cells from enzyme-digested placental tissue. Sets of lots of placental cells, obtained from a plurality of placentas, can be arranged in a bank of isolated placental cells for, e.g., long-term storage. Generally, tissue culture plastic-adherent placental cells are obtained from an initial culture of placental material to form a seed culture, which is expanded under controlled conditions to form populations of cells from approximately equivalent numbers of doublings. Lots are preferably derived from the tissue of a single placenta, but can be derived from the tissue of a plurality of placentas.

In one embodiment, placental cell lots are obtained as follows. Placental tissue is first disrupted, e.g., by mincing, digested with a suitable enzyme, e.g., trypsin or collagenase (see Section 4.3.3, above). The placental tissue preferably comprises, e.g., the entire amnion, entire chorion, or both, from a single placenta, but can comprise only a part of either the amnion or chorion. The digested tissue is cultured, e.g., for about 1-3 weeks, preferably about 2 weeks. After removal of non-adherent cells, high-density colonies that form are collected, e.g., by trypsinization. These cells are collected and resuspended in a convenient volume of culture medium, and are then used to seed expansion cultures. Expansion cultures can be any arrangement of separate cell culture apparatuses, e.g., a Cell Factory by NUNC™. Cells can be subdivided to any degree so as to seed expansion cultures with, e.g., $1 \times 10^3$, $2 \times 10^3$, $3 \times 10^3$, $4 \times 10^3$, $5 \times 10^3$, $6 \times 10^3$, $7 \times 10^3$, $8 \times 10^3$, $9 \times 10^3$, $1 \times 10^4$, $1 \times 10^4$, $2 \times 10^4$, $3 \times 10^4$, $4 \times 10^4$, $5 \times 10^4$, $6 \times 10^4$, $7 \times 10^4$, $8 \times 10^4$, $9 \times 10^4$, or $10 \times 10^4$ cell/cm$^2$. Preferably, from about $1 \times 10^3$ to about $1 \times 10^4$ cells/cm$^2$ are used to seed each expansion culture. The number of expansion cultures may be greater or fewer in number depending upon the particular placenta(s) from which the cells are obtained.

Expansion cultures are grown until the density of cells in culture reaches a certain value, e.g., about $1 \times 10^5$ cells/cm$^2$. Cells can either be collected and cryopreserved at this point, or passaged into new expansion cultures as described above. Cells can be passaged, e.g., 2, 3, 4, 5, 6, 7, 8, 9, 10, 11, 12, 13, 14, 15, 16, 17, 18, 19 or 20 times prior to use. A record of the cumulative number of population doublings is preferably maintained during expansion culture(s). The cells from a culture can be expanded for 2, 3, 4, 5, 6, 7, 8, 9, 10, 12, 14, 16, 18, 20, 22, 24, 26, 28, 30, 32, 34, 36, 38 or 40 doublings, or up to 60 doublings. Preferably, however, the number of population doublings, prior to dividing the population of cells into individual doses, is from about 15 to about 30. The cells can be culture continuously throughout the expansion process, or can be frozen at one or more points during expansion.

Cells to be used for individual doses can be frozen, e.g., cryopreserved for later use. Individual doses can comprise, e.g., about 1 million to about 50 million cells per ml, and can comprise between about $10^6$ and about $10^{10}$ cells in total.

In one embodiment, therefore, a placental cell bank can be made by a method comprising: expanding primary culture placental cells from a human post-partum placenta for a first plurality of population doublings; cryopreserving said placental cells to form a Master Cell Bank; expanding a plurality of placental cells from the Master Cell Bank for a second plurality of population doublings; cryopreserving said placental cells to form a Working Cell Bank; expanding a plurality of placental cells from the Working Cell Bank for a third plurality of population doublings; and cryopreserving said placental cells in individual doses, wherein said individual doses collectively compose a placental cell bank. Optionally, a plurality of placental cells from said third plurality of population doublings can be expanded for a fourth plurality of population doublings and cryopreserved in individual doses, wherein said individual doses collectively compose a placental cell bank.

In another specific embodiment, said primary culture placental cells comprise placental cells from placental perfusate. In another specific embodiment, said primary culture placental cells comprise placental cells from digested placental tissue. In another specific embodiment, said primary culture placental cells comprise placental cells from placental perfusate and from digested placental tissue. In another specific embodiment, all of said placental cells in said placental cell primary culture are from the same placenta. In another specific embodiment, the method further comprises the step of selecting CD200$^+$ or HLA-G$^-$ placental cells from said plurality of said placental cells from said Working Cell Bank to form individual doses. In another specific embodiment, said individual doses comprise from about $10^4$ to about $10^5$ placental cells. In another specific embodiment, said individual doses comprise from about $10^5$ to about $10^6$ placental cells. In another specific embodiment, said individual doses comprise from about $10^6$ to about $10^7$ placental cells. In another specific embodiment, said individual doses comprise from about $10^7$ to about $10^8$ placental cells. In another specific embodiment, said individual doses comprise from about $10^8$ to about $10^9$ placental cells. In another specific embodiment, said individual doses comprise from about $10^9$ to about $10^{10}$ placental cells.

In a preferred embodiment, the donor from which the placenta is obtained (e.g., the mother) is tested for at least one pathogen. If the mother tests positive for a tested pathogen, the entire lot from the placenta is discarded. Such testing can be performed at any time during production of placental cell lots, e.g., during expansion culture. Pathogens for which the presence is tested can include, without limitation, hepatitis A, hepatitis B, hepatitis C, hepatitis D, hepatitis E, human immunodeficiency virus (types I and II), cytomegalovirus, herpesvirus, and the like.

4.6 Preservation of Placental Cells

Isolated placental cells, e.g., the isolated placental cells described in Section 4.3.2, above, can be preserved, that is, placed under conditions that allow for long-term storage, or conditions that inhibit cell death by, e.g., apoptosis or necrosis.

Placental cells can be preserved using, e.g., a composition comprising an apoptosis inhibitor, necrosis inhibitor and/or an oxygen-carrying perfluorocarbon, as described in related U.S. Application Publication No. 2007/0190042, the disclosure of which is incorporated herein by reference in its entirety. In one embodiment, a method of preserving a population of cells, useful in the methods and compositions described herein, comprises contacting said population of cells with a cell collection composition comprising an inhibitor of apoptosis and an oxygen-carrying perfluorocarbon, wherein said inhibitor of apoptosis is present in an amount and for a time sufficient to reduce or prevent apoptosis in the population of cells, as compared to a population of cells not contacted with the inhibitor of apoptosis. In a specific embodiment, said inhibitor of apoptosis is a caspase inhibitor. In another specific embodiment, said inhibitor of apoptosis is a JNK inhibitor. In another specific embodiment, said JNK inhibitor does not modulate differentiation or proliferation of said cells. In another embodiment, said cell collection composition comprises said inhibitor of apoptosis and said oxygen-carrying perfluorocarbon in separate phases. In another embodiment, said cell collection composition comprises said inhibitor of apoptosis and said oxygen-carrying perfluorocarbon in an emulsion. In another embodiment, the cell collection composition additionally comprises an emulsifier, e.g., lecithin. In another embodiment, said apoptosis inhibitor and said perfluorocarbon are between about 0° C. and about 25° C. at the time of contacting the cells. In another specific embodiment, said apoptosis inhibitor and said perfluorocarbon are between about 2° C. and 10° C., or between about 2° C. and about 5° C., at the time of contacting the cells. In another specific embodiment, said contacting is performed during transport of said population of cells. In another specific embodiment, said contacting is performed during freezing and thawing of said population of cells.

Populations of placental cells can be preserved, e.g., by a method comprising contacting said population of cells with an inhibitor of apoptosis and an organ-preserving compound, wherein said inhibitor of apoptosis is present in an amount and for a time sufficient to reduce or prevent apoptosis in the population of cells, as compared to a population of cells not contacted with the inhibitor of apoptosis. In a specific embodiment, the organ-preserving compound is UW solution (described in U.S. Pat. No. 4,798,824; also known as ViaSpan; see also Southard et al., *Transplantation* 49(2):251-

257 (1990)) or a solution described in Stern et al., U.S. Pat. No. 5,552,267, the disclosures of which are hereby incorporated by reference in their entireties. In another embodiment, said organ-preserving compound is hydroxyethyl starch, lactobionic acid, raffinose, or a combination thereof. In another embodiment, the cell collection composition additionally comprises an oxygen-carrying perfluorocarbon, either in two phases or as an emulsion.

In another embodiment of the method, placental cells are contacted with a cell collection composition comprising an apoptosis inhibitor and oxygen-carrying perfluorocarbon, organ-preserving compound, or combination thereof, during perfusion. In another embodiment, said cells are contacted during a process of tissue disruption, e.g., enzymatic digestion. In another embodiment, placental cells are contacted with said cell collection compound after collection by perfusion, or after collection by tissue disruption, e.g., enzymatic digestion.

Typically, during placental cell collection, enrichment and isolation, it is preferable to minimize or eliminate cell stress due to hypoxia and mechanical stress. In another embodiment of the method, therefore, a cell, or population of cells, is exposed to a hypoxic condition during collection, enrichment or isolation for less than six hours during said preservation, wherein a hypoxic condition is a concentration of oxygen that is less than normal blood oxygen concentration. In another specific embodiment, said population of cells is exposed to said hypoxic condition for less than two hours during said preservation. In another specific embodiment, said population of cells is exposed to said hypoxic condition for less than one hour, or less than thirty minutes, or is not exposed to a hypoxic condition, during collection, enrichment or isolation. In another specific embodiment, said population of cells is not exposed to shear stress during collection, enrichment or isolation.

Placental cells can be cryopreserved, e.g., in cryopreservation medium in small containers, e.g., ampoules. Suitable cryopreservation medium includes, but is not limited to, culture medium including, e.g., growth medium, or cell freezing medium, for example commercially available cell freezing medium, e.g., C2695, C2639 or C6039 (Sigma). Cryopreservation medium preferably comprises DMSO (dimethylsulfoxide), at a concentration of about 2% to about 15% (v/v), e.g., about 10% (v/v). Cryopreservation medium may comprise additional agents, for example, methylcellulose and/or glycerol. Placental cells are preferably cooled at about 1° C./min during cryopreservation. A preferred cryopreservation temperature is about −80° C. to about −180° C., preferably about −125° C. to about −140° C. Cryopreserved cells can be transferred to liquid nitrogen prior to thawing for use. In some embodiments, for example, once the ampoules have reached about −90° C., they are transferred to a liquid nitrogen storage area. Cryopreservation can also be done using a controlled-rate freezer. Cryopreserved cells preferably are thawed at a temperature of about 25° C. to about 40° C., preferably to a temperature of about 37° C.

4.7 Compositions Comprising Isolated Placental Cells

The placental cells described herein, e.g., at Section 4.4.2, can be combined with any physiologically-acceptable or medically-acceptable compound, composition or device for use in the methods and compositions described herein. Compositions useful in the methods of treatment provided herein can comprise any one or more of the placental cells described herein (see Section 4.4.2, above). In certain embodiments, the composition is a pharmaceutically-acceptable composition, e.g., a composition comprising placental cells in a pharmaceutically-acceptable carrier. See Section 4.9.2, below.

In certain embodiments, a composition comprising the isolated placental cells additionally comprises a matrix, e.g., a decellularized matrix or a synthetic matrix. In another specific embodiment, said matrix is a three-dimensional scaffold. In another specific embodiment, said matrix comprises collagen, gelatin, laminin, fibronectin, pectin, ornithine, or vitronectin. In another ore specific embodiment, the matrix is an amniotic membrane or an amniotic membrane-derived biomaterial. In another specific embodiment, said matrix comprises an extracellular membrane protein. In another specific embodiment, said matrix comprises a synthetic compound. In another specific embodiment, said matrix comprises a bioactive compound. In another specific embodiment, said bioactive compound is a growth factor, cytokine, antibody, or organic molecule of less than 5,000 daltons.

In another embodiment, a composition useful in the methods of treatment provided herein comprises medium conditioned by any of the foregoing placental cells, or any of the foregoing placental cell populations.

4.7.1 Cryopreserved Isolated Placental Cells

The isolated placental cell populations useful in the methods and compositions described herein can be preserved, for example, cryopreserved for later use. Methods for cryopreservation of cells, such as stem cells, are well known in the art. Isolated placental cell populations can be prepared in a form that is easily administrable to an individual, e.g., an isolated placental cell population that is contained within a container that is suitable for medical use. Such a container can be, for example, a syringe, sterile plastic bag, flask, jar, or other container from which the isolated placental cell population can be easily dispensed. For example, the container can be a blood bag or other plastic, medically-acceptable bag suitable for the intravenous administration of a liquid to a recipient. The container is preferably one that allows for cryopreservation of the combined cell population.

The cryopreserved isolated placental cell population can comprise isolated placental cell derived from a single donor, or from multiple donors. The isolated placental cell population can be completely HLA-matched to an intended recipient, or partially or completely HLA-mismatched.

Thus, in one embodiment, isolated placental cells can be used in the methods and described herein in the form of a composition comprising a tissue culture plastic-adherent placental cell population in a container. In a specific embodiment, the isolated placental cells are cryopreserved. In another specific embodiment, the container is a bag, flask, or jar. In another specific embodiment, said bag is a sterile plastic bag. In another specific embodiment, said bag is suitable for, allows or facilitates intravenous administration of said isolated placental cell population, e.g., by intravenous infusion. The bag can comprise multiple lumens or compartments that are interconnected to allow mixing of the isolated placental cells and one or more other solutions, e.g., a drug, prior to, or during, administration. In another specific embodiment, the composition comprises one or more compounds that facilitate cryopreservation of the combined cell population. In another specific embodiment, said isolated placental cell population is contained within a physiologically-acceptable aqueous solution. In another specific embodiment, said physiologically-acceptable aqueous solution is a 0.9% NaCl solution. In another specific embodiment, said isolated placental cell population comprises placental cells that are HLA-matched to a recipient of said cell population. In another specific embodiment, said combined cell population comprises placental cells that are at least partially HLA-mismatched to a recipient of said cell population. In another specific embodiment, said isolated placental cells are derived from a plurality of donors.

In certain embodiments, the isolated placental cells in the container are isolated $CD10^+$, $CD34^-$, $CD105^+$ placental cells, wherein said cells have been cryopreserved, and are contained within a container. In a specific embodiment, said $CD10^+$, $CD34^-$, $CD105^+$ placental cells are also $CD200^+$. In another specific embodiment, said $CD10^+$, $CD34^-$, $CD105^+$, $CD200^+$ placental cells are also $CD45^-$ or $CD90^+$. In another specific embodiment, said $CD10^+$, $CD34^-$, $CD105^+$, $CD200^+$ placental cells are also $CD45^-$ and $CD90^+$. In another specific embodiment, the $CD34^-$, $CD10^+$, $CD105^+$ placental cells are additionally one or more of $CD13^-$, $CD29^+$, $CD33^+$, $CD38^-$, $CD44^+$, $CD45^-$, $CD54^+$, $CD62E^-$, $CD62L^-$, $CD62P^-$, $SH3^+$ ($CD73^+$), $SH4^+$ ($CD73^+$), $CD80^-$, $CD86^-$, $CD90^+$, $SH2^+$ ($CD105^+$), $CD106/VCAM^+$, $CD117^-$, $CD144/VE$-$cadherin^{dim}$, $CD184/CXCR4^-$, $CD200^+$, $CD133^-$, $OCT$-$4^+$, $SSEA3^-$, $SSEA4^-$, $ABC$-$p^+$, $KDR^-$ ($VEGFR2^-$), $HLA$-$A,B,C^+$, $HLA$-$DP,DQ,DR^-$, $HLA$-$G^-$, or Programmed Death-1 Ligand (PDL1)$^+$, or any combination thereof. In another specific embodiment, the $CD34^-$, $CD10^+$, $CD105^+$ placental cells are additionally $CD13^+$, $CD29^+$, $CD33^+$, $CD38^-$, $CD44^+$, $CD45^-$, $CD54/ICAM^+$, $CD62E^-$, $CD62L^-$, $CD62P^-$, $SH3^+$ ($CD73^+$), $SH4^+$ ($CD73^+$), $CD80^-$, $CD86^-$, $CD90^+$, $SH2^+$ ($CD105^+$), $CD106/VCAM^+$, $CD117^-$, $CD144/VE$-$cadherin^{dim}$, $CD184/CXCR4^-$, $CD200^+$, $CD133^-$, $OCT$-$4^+$, $SSEA3^-$, $SSEA4^-$, $ABC$-$p^-$, $KDR^-$ ($VEGFR2^-$), $HLA$-$A,B,C^+$, $HLA$-$DP,DQ,DR^-$, $HLA$-$G^-$, and Programmed Death-1 Ligand (PDL1)$^+$.

In certain other embodiments, the above-referenced isolated placental cells are isolated $CD200^+$, $HLA$-$G^-$ placental cells, wherein said cells have been cryopreserved, and are contained within a container. In another embodiment, the isolated placental cells are $CD73^+$, $CD105^-$, $CD200^+$ cells that have been cryopreserved, and are contained within a container. In another embodiment, the isolated placental cells are $CD200^+$, $OCT$-$4^-$ stem cells that have been cryopreserved, and are contained within a container. In another embodiment, the isolated placental cells are $CD73^+$, $CD105^+$ cells that have been cryopreserved, and are contained within a container, and wherein said isolated placental cells facilitate the formation of one or more embryoid-like bodies when cultured with a population of placental cells under conditions that allow for the formation of embryoid-like bodies. In another embodiment, the isolated placental cells are $CD73^+$, $CD105^+$, $HLA$-$G^-$ cells that have been cryopreserved, and are contained within a container. In another embodiment, the isolated placental cells are $OCT$-$4^+$ placental cells that have been cryopreserved, and are contained within a container, and wherein said cells facilitate the formation of one or more embryoid-like bodies when cultured with a population of placental cells under conditions that allow for the formation of embryoid-like bodies.

In another specific embodiment, the above-referenced isolated placental cells are placental stem cells or placental multipotent cells that are $CD34^-$, $CD10^+$ and $CD105^+$ as detected by flow cytometry (e.g., PDACs). In another specific embodiment, the isolated $CD34^-$, $CD10^+$, $CD105^+$ placental cells have the potential to differentiate into cells of a neural phenotype, cells of an osteogenic phenotype, or cells of a chondrogenic phenotype. In another specific embodiment, the isolated $CD34^-$, $CD10^+$, $CD105^{30}$ placental cells are additionally $CD200^+$. In another specific embodiment, the isolated $CD34^-$, $CD10^-$, $CD105^+$ placental cells are additionally $CD90^+$ or $CD45^-$, as detected by flow cytometry. In another specific embodiment, the isolated $CD34^-$, $CD10^+$, $CD105^+$ placental cells are additionally $CD90^+$ or $CD45^-$, as detected by flow cytometry. In another specific embodiment, the $CD34^-$, $CD10^+$, $CD105^+$, $CD200^+$ placental cells are additionally $CD90^+$ or $CD45^-$, as detected by flow cytometry. In another specific embodiment, the $CD34^-$, $CD10^+$, $CD105^+$, $CD200^-$ cells are additionally $CD90^+$ and $CD45^-$, as detected by flow cytometry. In another specific embodiment, the $CD34^-$, $CD10^+$, $CD105^+$, $CD200^+$, $CD90^+$, $CD45^-$ cells are additionally $CD80^-$ and $CD86^-$, as detected by flow cytometry. In another specific embodiment, the $CD34^-$, $CD10^+$, $CD105^+$ cells are additionally one or more of $CD29^+$, $CD38^-$, $CD44^+$, $CD54^+$, $CD80^-$, $CD86^-$, $SH3^+$ or $SH4^+$. In another specific embodiment, the cells are additionally $CD44^+$. In a specific embodiment of any of the isolated $CD34^-$, $CD10^-$, $CD105^+$ placental cells above, the cells are additionally one or more of $CD117^-$, $CD133^-$, $KDR^-$ ($VEGFR2^-$), $HLA$-$A,B,C^+$, $HLA$-$DP,DQ,DR^-$, and/or $PDL1^+$.

In a specific embodiment of any of the foregoing cryopreserved isolated placental cells, said container is a bag. In various specific embodiments, said container comprises about, at least, or at most $1 \times 10^6$ said isolated placental cells, $5 \times 10^6$ said isolated placental cells, $1 \times 10^7$ said isolated placental cells, $5 \times 10^7$ said isolated placental cells, $1 \times 10^8$ said isolated placental cells, $5 \times 10^8$ said isolated placental cells, $1 \times 10^9$ said isolated placental cells, $5 \times 10^9$ said isolated placental cells, $1 \times 10^{10}$ said isolated placental cells, or $1 \times 10^{10}$ said isolated placental cells. In other specific embodiments of any of the foregoing cryopreserved populations, said isolated placental cells have been passaged about, at least, or no more than 5 times, no more than 10 times, no more than 15 times, or no more than 20 times. In another specific embodiment of any of the foregoing cryopreserved isolated placental cells, said isolated placental cells have been expanded within said container.

4.7.2 Genetically Engineered Placental Cells

Further provided herein are placental cells, e.g., any of the placental multipotent cells or placental cells described in Section 4.2.2, above, or pharmaceutical compositions comprising such placental cells, wherein the placental cells have been genetically engineered to produce recombinant or exogenous cytokines.

Methods for genetically engineering cells, for example with retroviral vectors, adenoviral vectors, adeno-associated viral vectors, polyethylene glycol, or other methods known to those skilled in the art, can be used. These include using expression vectors which transport and express nucleic acid molecules in the cells. (See Geoddel; Gene Expression Technology: Methods in Enzymology 185, Academic Press, San Diego, Calif. (1990)). Vector DNA can be introduced into prokaryotic or eukaryotic cells via conventional transformation or transfection techniques. Suitable methods for transforming or transfecting host cells can be found in Sambrook et al. Molecular Cloning: A Laboratory Manual, 2nd Edition, Cold Spring Harbor Laboratory press (1989), and other laboratory textbooks.

Placental cells, e.g., the PDACs described in Section 4.2, above, can be genetically modified by introducing DNA or RNA into the cell, e.g., DNA or RNA encoding a protein of interest, by methods including viral transfer, including the use of DNA or RNA viral vectors, such as retroviruses (including lentiviruses), Simian virus 40 (SV40), adenovirus, Sindbis virus, and bovine papillomavirus for example; chemical transfer, including calcium phosphate transfection and DEAE dextran transfection methods; membrane fusion transfer, using DNA-loaded membrane vesicles such as liposomes, red blood cell ghosts, and protoplasts, for example; or physical transfer techniques, such as microinjection, electroporation, or naked DNA transfer. The placental cells can be genetically altered by insertion of exogenous DNA, or by substitution of a segment of the cellular genome with exogenous DNA. Insertion of exogenous DNA sequence(s) can be accomplished, e.g., by homologous recombination or by viral integration into the host cell genome, or by incorporating the DNA into the cell, particularly into its nucleus, using a plasmid expression vector and a nuclear localization sequence. The DNA can comprise one or more promoters that allow positive or negative induction of expression of the protein of interest using certain chemicals/drugs, e.g., tetracycline; the promoters can, in other embodiments, be constitutive.

Calcium phosphate transfection can be used to introduce, e.g., plasmid DNA containing a polynucleotide sequence encoding the protein of interest, into a cell. In certain embodiments, DNA is combined with a solution of calcium chloride, then added to a phosphate-buffered solution. Once a precipitate has formed, the solution is added directly to cultured cells. Treatment with DMSO or glycerol can be used to improve transfection efficiency, and levels of stable transfectants can be improved using bis-hydroxyethylamino ethanesulfonate (BES). Calcium phosphate transfection systems are commercially available (e.g., PROFECTION®, Promega Corp., Madison, Wis.). DEAE-dextran transfection may also be used.

Isolated placental cells may also be genetically engineered by microinjection. In certain embodiments, a glass micropipette is guided into the nucleus of cells under a light microscope to inject DNA or RNA.

Placental cells can also be genetically modified using electroporation. In certain embodiments, DNA or RNA is added to a suspension of cultured cells, and the DNA/RNA-cell suspension is placed between two electrodes and subjected to an electrical pulse, causing a transient permeability in the cell's outer membrane that is manifested by the appearance of pores across the membrane.

Liposomal delivery of DNA or RNA to genetically modify the cells can be performed using cationic liposomes, optionally including dioleoyl phosphatidylethanolamine (DOPE) or dioleoyl phosphatidylcholine (DOPC), e.g., LIPOFECTIN® (Life Technologies, Inc.). Other commercially-available delivery systems include EFFECTENE™ (Qiagen), DOTAP (Roche Molecular Biochemicals), FUGENE 6™. (Roche Molecular Biochemicals), and TRANSFECTAM® (Promega).

Viral vectors can be used to genetically alter placental cells by delivery of, e.g., target genes, polynucleotides, antisense molecules, or ribozyme sequences into the cells. Retroviral vectors are effective for transducing rapidly-dividing cells, although a number of retroviral vectors have been developed to effectively transfer DNA into non-dividing cells as well. Packaging cell lines for retroviral vectors are known to those of skill in the art. In certain embodiments, a retroviral DNA vector contains two retroviral LTRs such that a first LTR is located 5' to the SV40 promoter, which is operationally linked to the target gene sequence cloned into a multicloning site, followed by a 3' second LTR. Once formed, the retroviral DNA vector is transferred into a packaging cell line using calcium phosphate-mediated transfection, as previously described. Following approximately 48 hours of virus production, the viral vector, now containing the target gene sequence, is harvested. Methods of transfecting cells using lentiviral vectors, recombinant herpes viruses, adenoviral vectors, or alphavirus vectors are known in the art.

Successful transfection or transduction of target cells can be demonstrated using genetic markers, in a technique that is known to those of skill in the art. The green fluorescent protein of Aequorea victoria, for example, has been shown to be an effective marker for identifying and tracking genetically modified hematopoietic cells. Alternative selectable markers include the β-Gal gene, truncated nerve growth factor receptor, or drug selectable markers (including but not limited to NEO, MTX, or hygromycin).

4.7.3 Pharmaceutical Compositions

Populations of isolated placental cells, e.g., PDACs, or populations of cells comprising the isolated placental cells, can be formulated into pharmaceutical compositions for use in vivo, e.g., in the methods of treatment provided herein. Such pharmaceutical compositions comprise a population of isolated placental cells, or a population of cells comprising isolated placental cells, in a pharmaceutically-acceptable carrier, e.g., a saline solution or other accepted physiologically-acceptable solution for in vivo administration. Pharmaceutical compositions comprising the isolated placental cells described herein can comprise any, or any combination, of the isolated placental cell populations, or isolated placental cells, described elsewhere herein. The pharmaceutical compositions can comprise fetal, maternal, or both fetal and maternal isolated placental cells. The pharmaceutical compositions provided herein can further comprise isolated placental cells obtained from a single individual or placenta, or from a plurality of individuals or placentae.

The pharmaceutical compositions provided herein can comprise any number of isolated placental cells. For example, a single unit dose of isolated placental cells can comprise, in various embodiments, about, at least, or no more than $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$ or more isolated placental cells.

The pharmaceutical compositions provided herein comprise populations of cells that comprise 50% viable cells or more (that is, at least 50% of the cells in the population are functional or living). Preferably, at least 60% of the cells in the population are viable. More preferably, at least 70%, 80%, 90%, 95%, or 99% of the cells in the population in the pharmaceutical composition are viable.

The pharmaceutical compositions provided herein can comprise one or more compounds that, e.g., facilitate engraftment (e.g., anti-T-cell receptor antibodies, an immunosuppressant, or the like); stabilizers such as albumin, dextran 40, gelatin, hydroxyethyl starch, plasmalyte, and the like.

When formulated as an injectable solution, in one embodiment, the pharmaceutical composition comprises about 1% to 1.5% HSA and about 2.5% dextran. In a preferred embodiment, the pharmaceutical composition comprises from about $5 \times 10^6$ cells per milliliter to about $2 \times 10^7$ cells per milliliter in a solution comprising 5% HSA and 10% dextran, optionally comprising an immunosuppressant, e.g., cyclosporine A at, e.g., 10 mg/kg.

In other embodiments, the pharmaceutical composition, e.g., a solution, comprises a plurality of cells, e.g., isolated placental cells, for example, placental stem cells or placental multipotent cells, wherein said pharmaceutical composition comprises between about $1.0 \pm 0.3 \times 10^6$ cells per milliliter to about $5.0 \pm 1.5 \times 10^6$ cells per milliliter. In other embodiments, the pharmaceutical composition comprises between about $1.5 \times 10^6$ cells per milliliter to about $3.75 \times 10^6$ cells per milliliter. In other embodiments, the pharmaceutical composition comprises between about $1 \times 10^6$ cells/mL to about $50 \times 10^6$ cells/mL, about $1 \times 10^6$ cells/mL to about $40 \times 10^6$ cells/mL, about $1 \times 10^6$ cells/mL to about $30 \times 10^6$ cells/mL, about $1 \times 10^6$ cells/mL to about $20 \times 10^6$ cells/mL, about $1 \times 10^6$ cells/mL to about $15 \times 10^6$ cells/mL, or about $1 \times 10^6$ cells/mL to about $10 \times 10^6$ cells/mL. In certain embodiments, the pharmaceutical composition comprises no visible cell clumps (i.e., no macro cell clumps), or substantially no such visible clumps. As used herein, "macro cell clumps" means an aggregation of cells visible without magnification, e.g., visible to the naked eye, and generally refers to a cell aggregation larger than about 150 microns In some embodiments, the pharmaceutical composition comprises about 2.5%, 3.0%, 3.5%, 4.0%, 4.5%, 5.0%, 5.5%, 6.0%, 6.5%, 7.0%, 7.5% 8.0%, 8.5%, 9.0%, 9.5% or 10% dextran, e.g., dextran-40. In a specific embodiment, said composition comprises about 7.5% to about 9% dextran-40. In a specific embodiment, said composition comprises about 5.5% dextran-40. In certain embodiments, the pharmaceutical composition comprises from about 1% to about 15% human serum albumin (HSA). In specific embodiments, the pharmaceutical composition comprises about 1%, 2%, 3%, 4%, 5%, 65, 75, 8%, 9%, 10%, 11%, 12%, 13%, 14% or 15% HSA. In a specific embodiment, said cells have been cryopreserved and thawed. In another specific embodiment, said cells have been filtered through a 70 μM to 100 μM filter. In another specific embodiment, said composition comprises no visible cell clumps. In another specific embodiment, said composition comprises fewer than about 200 cell clumps per $10^6$ cells, wherein said cell clumps are visible only under a microscope, e.g., a light microscope. In another specific embodiment, said composition comprises fewer than about 150 cell clumps per $10^6$ cells, wherein said cell clumps are visible only under a microscope, e.g., a light microscope. In another specific embodiment, said composition comprises fewer than about 100 cell clumps per $10^6$ cells, wherein said cell clumps are visible only under a microscope, e.g., a light microscope.

In a specific embodiment, the pharmaceutical composition comprises about $1.0\pm0.3\times10^6$ cells per milliliter, about 5.5% dextran-40 (w/v), about 10% HSA (w/v), and about 5% DMSO (v/v).

In other embodiments, the pharmaceutical composition comprises a plurality of cells, e.g., a plurality of isolated placental cells in a solution comprising 10% dextran-40, wherein the pharmaceutical composition comprises between about $1.0\pm0.3\times10^6$ cells per milliliter to about $5.0\pm1.5\times10^6$ cells per milliliter, and wherein said composition comprises no cell clumps visible with the unaided eye (i.e., comprises no macro cell clumps). In some embodiments, the pharmaceutical composition comprises between about $1.5\times10^6$ cells per milliliter to about $3.75\times10^6$ cells per milliliter. In a specific embodiment, said cells have been cryopreserved and thawed. In another specific embodiment, said cells have been filtered through a 70 μM to 100 μM filter. In another specific embodiment, said composition comprises fewer than about 200 micro cell clumps (that is, cell clumps visible only with magnification) per $10^6$ cells. In another specific embodiment, the pharmaceutical composition comprises fewer than about 150 micro cell clumps per $10^6$ cells. In another specific embodiment, the pharmaceutical composition comprises fewer than about 100 micro cell clumps per $10^6$ cells. In another specific embodiment, the pharmaceutical composition comprises less than 15%, 14%, 13%, 12%, 11%, 10%, 9%, 8%, 7%, 6%, 5%, 4%, 3%, or 2% DMSO, or less than 1%, 0.9%, 0.8%, 0.7%, 0.6%, 0.5%, 0.4%, 0.3%, 0.2%, or 0.1% DMSO.

Further provided herein are compositions comprising cells, wherein said compositions are produced by one of the methods disclosed herein. For example, in one embodiment, the pharmaceutical composition comprises cells, wherein the pharmaceutical composition is produced by a method comprising filtering a solution comprising placental cells, e.g., placental stem cells or placental multipotent cells, to form a filtered cell-containing solution; diluting the filtered cell-containing solution with a first solution to about 1 to $50\times10^6$, 1 to $40\times10^6$, 1 to $30\times10^6$, 1 to $20\times10^6$, 1 to $15\times10^6$, or 1 to $10\times10^6$ cells per milliliter, e.g., prior to cryopreservation; and diluting the resulting filtered cell-containing solution with a second solution comprising dextran, but not comprising human serum albumin (HSA) to produce said composition. In certain embodiments, said diluting is to no more than about $15\times10^6$ cells per milliliter. In certain embodiments, said diluting is to no more than about $10\pm3\times10^6$ cells per milliliter. In certain embodiments, said diluting is to no more than about $7.5\times10^6$ cells per milliliter. In other certain embodiments, if the filtered cell-containing solution, prior to the dilution, comprises less than about $15\times10^6$ cells per milliliter, filtration is optional. In other certain embodiments, if the filtered cell-containing solution, prior to the dilution, comprises less than about $10\pm3\times10^6$ cells per milliliter, filtration is optional. In other certain embodiments, if the filtered cell-containing solution, prior to the dilution, comprises less than about $7.5\times10^6$ cells per milliliter, filtration is optional.

In a specific embodiment, the cells are cryopreserved between said diluting with a first dilution solution and said diluting with said second dilution solution. In another specific embodiment, the first dilution solution comprises dextran and HSA. The dextran in the first dilution solution or second dilution solution can be dextran of any molecular weight, e.g., dextran having a molecular weight of from about 10 kDa to about 150 kDa. In some embodiments, said dextran in said first dilution solution or said second solution is about 2.5%, 3.0%, 3.5%, 4.0%, 4.5%, 5.0%, 5.5%, 6.0%, 6.5%, 7.0%, 7.5% 8.0%, 8.5%, 9.0%, 9.5% or 10% dextran. In another specific embodiment, the dextran in said first dilution solution or said second dilution solution is dextran-40. In another specific embodiment, the dextran in said first dilution solution and said second dilution solution is dextran-40. In another specific embodiment, said dextran-40 in said first dilution solution is 5.0% dextran-40. In another specific embodiment, said dextran-40 in said first dilution solution is 5.5% dextran-40. In another specific embodiment, said dextran-40 in said second dilution solution is 10% dextran-40. In another specific embodiment, said HSA in said solution comprising HSA is 1 to 15% HSA. In another specific embodiment, said HSA in said solution comprising HSA is about 1%, 2%, 3%, 4%, 5%, 6%, 7%, 8%, 9%, 10%, 11%, 12%, 13%, 14% or 15% HSA. In another specific embodiment, said HSA in said solution comprising HSA is 10% HSA. In another specific embodiment, said first dilution solution comprises HSA. In another specific embodiment, said HSA in said first dilution solution is 10% HSA. In another specific embodiment, said first dilution solution comprises a cryoprotectant. In another specific embodiment, said cryoprotectant is DMSO. In another specific embodiment, said dextran-40 in said second dilution solution is about 10% dextran-40. In another specific embodiment, said composition comprising cells comprises about 7.5% to about 9% dextran. In another specific embodiment, the pharmaceutical composition comprises from about $1.0\pm0.3\times10^6$ cells per milliliter to about $5.0\pm1.5\times10^6$ cells per milliliter. In another specific embodiment, the pharmaceutical composition comprises from about $1.5\times10^6$ cells per milliliter to about $3.75\times10^6$ cells per milliliter.

In another embodiment, the pharmaceutical composition is made by a method comprising (a) filtering a cell-containing solution comprising placental cells, e.g., placental stem cells or placental multipotent cells, prior to cryopreservation to produce a filtered cell-containing solution; (b) cryopreserving the cells in the filtered cell-containing solution at about 1 to $50\times10^6$, 1 to $40\times10^6$, 1 to $30\times10^6$, 1 to $20\times10^6$, 1 to $15\times10^6$, or 1 to 10×10⁶ cells per milliliter; (c) thawing the cells; and (d) diluting the filtered cell-containing solution about 1:1 to about 1:11 (v/v) with a dextran-40 solution. In certain embodiments, if the number of cells is less than about 10±3×10⁶ cells per milliliter prior to step (a), filtration is optional. In another specific embodiment, the cells in step (b) are cryopreserved at about 10±3×10⁶ cells per milliliter. In another specific embodiment, the cells in step (b) are cryopreserved in a solution comprising about 5% to about 10% dextran-40 and HSA. In certain embodiments, said diluting in step (b) is to no more than about 15×10⁶ cells per milliliter.

In another embodiment, the pharmaceutical composition is made by a method comprising: (a) suspending placental cells, e.g., placental stem cells or placental multipotent cells, in a 5.5% dextran-40 solution that comprises 10% HSA to form a cell-containing solution; (b) filtering the cell-containing solution through a 70 μM filter; (c) diluting the cell-containing solution with a solution comprising 5.5% dextran-40, 10% HSA, and 5% DMSO to about 1 to 50×10⁶, 1 to 40×10⁶, 1 to 30×10⁶, 1 to 20×10⁶, 1 to 15×10⁶, or 1 to 10×10⁶ cells per milliliter; (d) cryopreserving the cells; (e) thawing the cells; and (f) diluting the cell-containing solution 1:1 to 1:11 (v/v) with 10% dextran-40. In certain embodiments, said diluting in step (c) is to no more than about 15×10⁶ cells per milliliter. In certain embodiments, said diluting in step (c) is to no more than about 10±3×10⁶ cells/mL. In certain embodiments, said diluting in step (c) is to no more than about 7.5×10⁶ cells/mL.

In another embodiment, the composition comprising cells is made by a method comprising: (a) centrifuging a plurality of cells to collect the cells; (b) resuspending the cells in 5.5% dextran-40; (c) centrifuging the cells to collect the cells; (d) resuspending the cells in a 5.5% dextran-40 solution that comprises 10% HSA; (e) filtering the cells through a 70 μM filter; (f) diluting the cells in 5.5% dextran-40, 10% HSA, and 5% DMSO to about 1 to 50×10⁶, 1 to 40×10⁶, 1 to 30×10⁶, 1 to 20×10⁶, 1 to 15×10⁶, or 1 to 10×10⁶ cells per milliliter; (g) cryopreserving the cells; (h) thawing the cells; and (i) diluting the cells 1:1 to 1:11 (v/v) with 10% dextran-40. In certain embodiments, said diluting in step (f) is to no more than about 15×10⁶ cells per milliliter. In certain embodiments, said diluting in step (f) is to no more than about 10±3×10⁶ cells/mL. In certain embodiments, said diluting in step (f) is to no more than about 7.5×10⁶ cells/mL. In other certain embodiments, if the number of cells is less than about 10±3×10⁶ cells per milliliter, filtration is optional.

The compositions, e.g., pharmaceutical compositions comprising the isolated placental cells, described herein can comprise any of the isolated placental cells described herein.

Other injectable formulations, suitable for the administration of cellular products, may be used.

In one embodiment, the pharmaceutical composition comprises isolated placental cells that are substantially, or completely, non-maternal in origin, that is, have the fetal genotype; e.g., at least about 90%, 95%, 98%, 99% or about 100% are non-maternal in origin. For example, in one embodiment a pharmaceutical composition comprises a population of isolated placental cells that are $CD200^+$ and $HLA-G^-$; $CD73^+$, $CD105^+$, and $CD200^+$; $CD200^+$ and $OCT-4^+$; $CD73^+$, $CD105^+$ and $HLA-G^-$; $CD73^+$ and $CD105^+$ and facilitate the formation of one or more embryoid-like bodies in a population of placental cells comprising said population of isolated placental cell when said population of placental cells is cultured under conditions that allow the formation of an embryoid-like body; or $OCT-4^+$ and facilitate the formation of one or more embryoid-like bodies in a population of placental cells comprising said population of isolated placental cell when said population of placental cells is cultured under conditions that allow the formation of an embryoid-like body; or a combination of the foregoing, wherein at least 70%, 80%, 90%, 95% or 99% of said isolated placental cells are non-maternal in origin. In another embodiment, a pharmaceutical composition comprises a population of isolated placental cells that are $CD10^+$, $CD105^+$ and $CD34^-$; $CD10^-$, $CD105^+$, $CD200^+$ and $CD34^-$; $CD10^+$, $CD105^+$, $CD200^+$, $CD34^-$ and at least one of $CD90^+$ or $CD45^-$; $CD10^+$, $CD90^+$, $CD105^+$, $CD200^+$, $CD34^-$ and $CD45^-$; $CD10^+$, $CD90^+$, $CD105^-$, $CD200^+$, $CD34^-$ and $CD45^-$; $CD200^+$ and $HLA-G^-$; $CD73^+$, $CD105^+$, and $CD200^+$; $CD200^+$ and $OCT-4^+$; $CD73^+$, $CD105^+$ and $HLA-G^-$; $CD73^+$ and $CD105^-$ and facilitate the formation of one or more embryoid-like bodies in a population of placental cells comprising said isolated placental cells when said population of placental cells is cultured under conditions that allow the formation of an embryoid-like body; $OCT-4^+$ and facilitate the formation of one or more embryoid-like bodies in a population of placental cells comprising said isolated placental cells when said population of placental cells is cultured under conditions that allow the formation of an embryoid-like body; or one or more of $CD117^-$, $CD133^-$, KDR, $CD80^-$, $CD86^-$, $HLA-A,B,C^+$, $HLA-DP,DQ,DR^-$ and/or $PDL1^+$; or a combination of the foregoing, wherein at least 70%, 80%, 90%, 95% or 99% of said isolated placental cells are non-maternal in origin. In a specific embodiment, the pharmaceutical composition additionally comprises a stem cell that is not obtained from a placenta.

Isolated placental cells in the compositions, e.g., pharmaceutical compositions, provided herein, can comprise placental cells derived from a single donor, or from multiple donors. The isolated placental cells can be completely HLA-matched to an intended recipient, or partially or completely HLA-mismatched.

4.7.4 Matrices Comprising Isolated Placental Cells

Further provided herein are compositions comprising matrices, hydrogels, scaffolds, and the like that comprise a placental cell, or a population of isolated placental cells. Such compositions can be used in the place of, or in addition to, cells in liquid suspension.

The isolated placental cells described herein can be seeded onto a natural matrix, e.g., a placental biomaterial such as an amniotic membrane material. Such an amniotic membrane material can be, e.g., amniotic membrane dissected directly from a mammalian placenta; fixed or heat-treated amniotic membrane, substantially dry (i.e., <20% $H_2O$) amniotic membrane, chorionic membrane, substantially dry chorionic membrane, substantially dry amniotic and chorionic membrane, and the like. Preferred placental biomaterials on which isolated placental cells can be seeded are described in Hariri, U.S. Application Publication No. 2004/0048796, the disclosure of which is incorporated herein by reference in its entirety.

The isolated placental cells described herein can be suspended in a hydrogel solution suitable for, e.g., injection. Suitable hydrogels for such compositions include self-assembling peptides, such as RAD16. In one embodiment, a hydrogel solution comprising the cells can be allowed to harden, for instance in a mold, to form a matrix having cells dispersed therein for implantation. Isolated placental cells in such a matrix can also be cultured so that the cells are mitotically expanded prior to implantation. The hydrogel is, e.g., an organic polymer (natural or synthetic) that is cross-linked via covalent, ionic, or hydrogen bonds to create a three-dimensional open-lattice structure that entraps water molecules to form a gel. Hydrogel-forming materials include polysaccharides such as alginate and salts thereof, peptides, polyphosphazines, and polyacrylates, which are crosslinked ionically, or block polymers such as polyethylene oxide-polypropylene glycol block copolymers which are crosslinked by temperature or pH, respectively. In some embodiments, the hydrogel or matrix is biodegradable.

In some embodiments, the formulation comprises an in situ polymerizable gel (see., e.g., U.S. Patent Application Publication 2002/0022676, the disclosure of which is incorporated herein by reference in its entirety; Anseth et al., *J. Control Release,* 78(1-3):199-209 (2002); Wang et al., *Biomaterials,* 24(22):3969-80 (2003).

In some embodiments, the polymers are at least partially soluble in aqueous solutions, such as water, buffered salt solutions, or aqueous alcohol solutions, that have charged side groups, or a monovalent ionic salt thereof. Examples of polymers having acidic side groups that can be reacted with cations are poly(phosphazenes), poly(acrylic acids), poly (methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

The isolated placental cells described herein or co-cultures thereof can be seeded onto a three-dimensional framework or scaffold and implanted in vivo. Such a framework can be implanted in combination with any one or more growth factors, cells, drugs or other components that, e.g., stimulate tissue formation.

Examples of scaffolds that can be used include nonwoven mats, porous foams, or self assembling peptides. Nonwoven mats can be formed using fibers comprised of a synthetic absorbable copolymer of glycolic and lactic acids (e.g., PGA/PLA) (VICRYL, Ethicon, Inc., Somerville, N.J.). Foams, composed of, e.g., poly(ϵ-caprolactone)/poly(glycolic acid) (PCL/PGA) copolymer, formed by processes such as freeze-drying, or lyophilization (see, e.g., U.S. Pat. No. 6,355,699), can also be used as scaffolds.

In another embodiment, isolated placental cells can be seeded onto, or contacted with, a felt, which can be, e.g., composed of a multifilament yarn made from a bioabsorbable material such as PGA, PLA, PCL copolymers or blends, or hyaluronic acid.

The isolated placental cells provided herein can, in another embodiment, be seeded onto foam scaffolds that may be composite structures. Such foam scaffolds can be molded into a useful shape, such as that of a portion of a specific structure in the body to be repaired, replaced or augmented. In some embodiments, the framework is treated, e.g., with 0.1M acetic acid followed by incubation in polylysine, PBS, and/or collagen, prior to inoculation of the cells in order to enhance cell attachment. External surfaces of a matrix may be modified to improve the attachment or growth of cells and differentiation of tissue, such as by plasma-coating the matrix, or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate, etc.), a cellular matrix, and/or other materials such as, but not limited to, gelatin, alginates, agar, agarose, and plant gums, and the like.

In some embodiments, the scaffold comprises, or is treated with, materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as EPTFE, and segmented polyurethaneurea silicones, such as PURSPAN™ (The Polymer Technology Group, Inc., Berkeley, Calif.). The scaffold can also comprise anti-thrombotic agents such as heparin; the scaffolds can also be treated to alter the surface charge (e.g., coating with plasma) prior to seeding with isolated placental cells.

The placental cells (e.g., PDACs) provided herein can also be seeded onto, or contacted with, a physiologically-acceptable ceramic material including, but not limited to, mono-, di-, tri-, alpha-tri-, beta-tri-, and tetra-calcium phosphate, hydroxyapatite, fluoroapatites, calcium sulfates, calcium fluorides, calcium oxides, calcium carbonates, magnesium calcium phosphates, biologically active glasses such as BIO-GLASS®, and mixtures thereof. Porous biocompatible ceramic materials currently commercially available include SURGIBONE® (CanMedica Corp., Canada), ENDOBON® (Merck Biomaterial France, France), CEROS® (Mathys, AG, Bettlach, Switzerland), and mineralized collagen bone grafting products such as HEALOS™ (DePuy, Inc., Raynham, Mass.) and VITOSS®, RHAKOSS™, and CORTOSS® (Orthovita, Malvern, Pa.). The framework can be a mixture, blend or composite of natural and/or synthetic materials.

In one embodiment, the isolated placental cells are seeded onto, or contacted with, a suitable scaffold at about $0.5\times10^6$ to about $8\times10^6$ cells/mL.

4.8 Immortalized Placental Cell Lines

Mammalian placental cells, e.g., PDACs, can be conditionally immortalized by transfection with any suitable vector containing a growth-promoting gene, that is, a gene encoding a protein that, under appropriate conditions, promotes growth of the transfected cell, such that the production and/or activity of the growth-promoting protein is regulatable by an external factor. In a preferred embodiment the growth-promoting gene is an oncogene such as, but not limited to, v-myc, N-myc, c-myc, p53, SV40 large T antigen, polyoma large T antigen, E1a adenovirus or E7 protein of human papillomavirus.

External regulation of the growth-promoting protein can be achieved by placing the growth-promoting gene under the control of an externally-regulatable promoter, e.g., a promoter the activity of which can be controlled by, for example, modifying the temperature of the transfected cells or the composition of the medium in contact with the cells. In one embodiment, a tetracycline (tet)-controlled gene expression system can be employed (see Gossen et al., *Proc. Natl. Acad. Sci. USA* 89:5547-5551, 1992; Hoshimaru et al., *Proc. Natl. Acad. Sci. USA* 93:1518-1523, 1996). In the absence of tet, a tet-controlled transactivator (tTA) within this vector strongly activates transcription from $ph_{CMV^{*}-1}$, a minimal promoter from human cytomegalovirus fused to tet operator sequences. tTA is a fusion protein of the repressor (tetR) of the transposon-10-derived tet resistance operon of *Escherichia coli* and the acidic domain of VP16 of herpes simplex virus. Low, non-toxic concentrations of tet (e.g., 0.01-1.0 µg/mL) almost completely abolish transactivation by tTA.

In one embodiment, the vector further contains a gene encoding a selectable marker, e.g., a protein that confers drug resistance. The bacterial neomycin resistance gene ($neo^R$) is one such marker that may be employed within the present methods. Cells carrying $neo^R$ may be selected by means known to those of ordinary skill in the art, such as the addition of, e.g., 100-200 µg/mL G418 to the growth medium.

Transfection can be achieved by any of a variety of means known to those of ordinary skill in the art including, but not limited to, retroviral infection. In general, a cell culture may be transfected by incubation with a mixture of conditioned medium collected from the producer cell line for the vector and DMEM/F12 containing N2 supplements. For example, a placental cell culture prepared as described above may be infected after, e.g., five days in vitro by incubation for about 20 hours in one volume of conditioned medium and two volumes of DMEM/F12 containing N2 supplements. Transfected cells carrying a selectable marker may then be selected as described above.

Following transfection, cultures are passaged onto a surface that permits proliferation, e.g., allows at least 30% of the cells to double in a 24 hour period. Preferably, the substrate is a polyornithine/laminin substrate, consisting of tissue culture plastic coated with polyornithine (10 μg/mL) and/or laminin (10 μg/mL), a polylysine/laminin substrate or a surface treated with fibronectin. Cultures are then fed every 3-4 days with growth medium, which may or may not be supplemented with one or more proliferation-enhancing factors. Proliferation-enhancing factors may be added to the growth medium when cultures are less than 50% confluent.

The conditionally-immortalized placental cell lines can be passaged using standard techniques, such as by trypsinization, when 80-95% confluent. Up to approximately the twentieth passage, it is, in some embodiments, beneficial to maintain selection (by, for example, the addition of G418 for cells containing a neomycin resistance gene). Cells may also be frozen in liquid nitrogen for long-term storage.

Clonal cell lines can be isolated from a conditionally-immortalized human placental cell line prepared as described above. In general, such clonal cell lines may be isolated using standard techniques, such as by limit dilution or using cloning rings, and expanded. Clonal cell lines may generally be fed and passaged as described above.

Conditionally-immortalized human placental cell lines, which may, but need not, be clonal, may generally be induced to differentiate by suppressing the production and/or activity of the growth-promoting protein under culture conditions that facilitate differentiation. For example, if the gene encoding the growth-promoting protein is under the control of an externally-regulatable promoter, the conditions, e.g., temperature or composition of medium, may be modified to suppress transcription of the growth-promoting gene. For the tetracycline-controlled gene expression system discussed above, differentiation can be achieved by the addition of tetracycline to suppress transcription of the growth-promoting gene. In general, 1 μg/mL tetracycline for 4-5 days is sufficient to initiate differentiation. To promote further differentiation, additional agents may be included in the growth medium.

4.9 Kits

In another aspect, provided herein are kits, suitable for the treatment of an individual who has sarcoidosis or a sarcoidosis-related disease or disorder, comprising, in a container separate from remaining kit contents, tissue culture plastic adherent multipotent placental cells, e.g., placental stem cells or placental multipotent cells, e.g., the cells described in Section 4.2, above (PDACs), and instructions for use. Ideally the kit can be used in the field, for example in a physician's office, or by an emergency care provider to be applied to a patient diagnosed as having sarcoidosis or a sarcoidosis-related disease or disorder. Preferably, the placental cells are provided in a pharmaceutically-acceptable solution, e.g., a solution suitable for intralesional administration or a solution suitable for intravenous administration. In certain embodiments, the placental stem cells or placental multipotent cells are any of the $CD10^+$, $CD34^-$, $CD105^+$ placental cells described herein, e.g., $CD10^+$, $CD34^-$, $CD105^+$, $CD200^+$ placental cells or $CD10^+$, $CD34^-$, $CD45^-$, $CD90^+$, $CD105^+$, $CD200^+$ placental cells.

In certain embodiments, the kits comprise one or more components that facilitate delivery of the placental cells to the individual. For example, in certain embodiments, the kit comprises components that facilitate intralesional delivery of the placental cells to the individual. In such embodiments, the kit can comprise, e.g., syringes and needles suitable for delivery of cells to the individual, and the like. In such embodiments, the placental cells may be contained in the kit in a bag, or in one or more vials. In certain other embodiments, the kit comprises components that facilitate intravenous or intra-arterial delivery of the placental cells to the individual. In such embodiments, the placental cells may be contained, e.g., within a bottle or bag (for example, a blood bag or similar bag able to contain up to about 1.5 L solution comprising the cells), and the kit additionally comprises tubing and needles suitable for the delivery of cells to the individual.

Additionally, the kit may comprise one or more compounds that reduce pain or inflammation in the individual (e.g., an analgesic, steroidal or non-steroidal anti-inflammatory compound, or the like. The kit may also comprise an antibacterial or antiviral compound (e.g., one or more antibiotics), a compound to reduce anxiety in the individual (e.g., alaprazolam), a compound that reduces an immune response in the individual (e.g., cyclosporine A), an antihistamine (diphenhydramine, loratadine, desloratadine, quetiapine, fexofenadine, cetirizine, promethazine, chlorepheniramine, levocetirizine, cimetidine, famotidine, ranitidine, nizatidine, roxatidine, lafutidine, or the like).

Additionally, the kit can comprise disposables, e.g., sterile wipes, disposable paper goods, gloves, or the like, which facilitate preparation of the individual for delivery, or which reduce the likelihood of infection in the individual as a result of the administration of the placental cells.

5. EXAMPLES 5.1 Example 1

Treatment of Systemic Sarcoidosis Using Placental Stem Cells

A male patient in his middle '40s reports symptoms of weakness, shortness of breath, exertional dyspnea, chest pain, moderate fever and ankle and knee discomfort, and undergoes physical examination. The chest X-ray and CT scans reveal bilateral hilar and mediastinal lymphadenopathy, parenchymal lesions in the right lung and a numbers of nodules. Systemic sarcoidosis and infectious arthritis are diagnosed. The individual is administered $1\times10^9$ to $5\times10^9$ $CD10^+$, $CD34^-$, $CD105^+$, $CD200^+$ PDACs intravenously in 450 mL 0.9% saline, and is monitored biweekly for the next three months. Therapeutic effectiveness is established if any of the symptoms described above improve during the monitoring period.

5.2 Example 2

Treatment of Cardiac Sarcoidosis Using Placental Stem Cells

An individual presents with breathlessness, swelling of the legs and ankles, and irregular heartbeats. After excluding other causes, and with a confirmatory electrocardiogram, a diagnosis of cardiac sarcoidosis y is made. After stabilization of the individual with nitroglycerin and streptokinase, the individual is administered $1\times10^8$ to $5\times10^8$ $CD10^+$, $CD34^-$, $CD105^+$, $CD200^+$ PDACs in 0.9% saline directly to the affected area using a cardiac syringe with local anesthetic.

The individual is monitored on an emergency basis for the next 72 hours. The individual is further monitored over the next three months port-treatment by electrocardiogram and/or dye visualization techniques. Therapeutic effectiveness is established if any of the symptoms described above improve during the monitoring period.

5.3 Example 3

Treatment of Cutaneous Sarcoidosis Using Placental Stem Cells

An individual presents with complaints of nodules developing in the lower legs. A shave biopsy is performed and histologic examination reveals granulomatous inflammation with polarizable foreign material. After excluding other causes, a diagnosis of cutaneous sarcoidosis is made. The individual is administered $1 \times 10^8$ to $5 \times 10^8$ CD10$^+$, CD34, CD105$^+$, CD200$^+$ PDACs in 0.9% saline directly to the skin lesions. The individual is monitored over the next three months for changes in the skin nodules. Therapeutic effectiveness is established for the individual if any of these sings show improvement during the monitoring period.

5.4 Example 4

Treatment of Neurosarcodosis Using Placental Stem Cells

A 50-year-old individual exhibits symptoms of leg numbness and muscle weakness. Imaging modalities shows an irregular contour and a mass-like lesion in the spinal cord. A biopsy reveal fibrosis and non-caseating granulomata in the spinal cord. A diagnosis of neurosarcoidosis is made. The individual is administered $1 \times 10^9$ to $5 \times 10^9$ CD10$^+$, CD34$^-$, CD105$^+$, CD200$^+$ PDACs intrathecally in 450 mL 0.9% saline, and is monitored biweekly for the next three months. Therapeutic effectiveness is established if any of the symptoms described above improve during the monitoring period.

Equivalents:

The present disclosure is not to be limited in scope by the specific embodiments described herein. Indeed, various modifications of the subject matter provided herein, in addition to those described, will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

What is claimed:

1. A method of treating an individual having sarcoidosis comprising administering to the individual a therapeutically effective amount of placental stem cells, wherein the therapeutically effective amount is an amount sufficient to cause a detectable improvement in one or more symptoms of said sarcoidosis and wherein said sarcoidosis is systemic sarcoidosis, cutaneous sarcoidosis, Löfgren's syndrome, neurosarcoidosis, cardiac sarcoidosis, or ocular sarcoidosis.

2. The method of claim 1, wherein said placental stem cells are CD10$^+$, CD34$^{31}$, CD105$^+$, CD200$^+$placental stem cells.

3. The method of claim 2, wherein said placental stem cells are additionally CD45$^-$or CD90$^+$.

4. The method of claim 2, wherein said placental stem cells are additionally one or more of CD38$^-$, CD45$^-$, CD80$^-$, CD86$^-$, CD133$^-$, HLA-DR,DP,DQ$^-$, SSEA3$^-$, SSEA4$^-$, CD29$^+$, CD44$^+$, CD73$^+$, CD90$^+$, HLA-A,B,C$^+$, PDL1$^+$, ABC-p$^+$,or OCT-4$^+$.

5. The method of claim 2, wherein said placental stem cells are additionally one or more of CD29$^+$, CD38$^+$, CD44$^+$, CD54$^+$, SH3$^+$or SH4$^+$.

6. The method of claim 2, wherein said placental stem cells are additionally CD44$^+$.

7. The method of claim 1, wherein said placental stem cells express CD200 and do not express HLA-G, or express CD73, CD 105, and CD200, or express CD200 and OCT-4, or express CD73 and CD 105 and do not express HLA-G, or express CD73 and CD105 and facilitate the formation of one or more embryoid-like bodies in a population of placental cells comprising said stem cell when said population is cultured under conditions that allow for the formation of an embryoid-like body, or express OCT-4 and facilitate the formation of one or more embryoid-like bodies in a population of placental cells comprising said stem cell when said population is cultured under conditions that allow for the formation of an embryoid-like body.

8. The method of claim 1, wherein said sarcoidosis is systemic sarcoidosis.

9. The method of claim 8, wherein said symptom is one or more of formation of granulomas, fatigue, weight loss, fever, aches, pains, arthritis, dry eyes, swelling of the knees, blurry vision, shortness of breath, cough and skin lesions.

10. The method of claim 1, wherein said sarcoidosis is cutaneous sarcoidosis.

11. The method of claim 10, wherein the cutaneous sarcoidosis comprises annular sarcoidosis, erythrodermic sarcoidosis, ichthyosiform sarcoidosis, hypopigmented sarcoidosis, morpheaform sarcoidosis, mucosal sarcoidosis, papular sarcoid, scar sarcoid, subcutaneous sarcoidosis or ulcerative sarcoidosis.

12. The method of claim 11, wherein said symptom is a skin lesion.

13. The method of claim 12, wherein the skin lesion is one or more of erythema nodosum, nummular eczema, erythema multiforme, calcinosis cutis and pruritus, lupus pernio, skin plaques, maculopapular eruptions, nodular lesions deeper in the skin or infiltration of old scars.

14. The method of claim 1, wherein said sarcoidosis is Löfgren's syndrome.

15. The method of claim 14, wherein said symptom is one or more of erythema nodosum, bilateral hilar denopathy, arthritis, arthralgias or fever.

16. The method of claim 1, wherein said sarcoidosis is neurosarcoidosis.

17. The method of claim 16, wherein said symptom is one or more of formation of granulomas in the nervous system, headache, confusion, malaise or facial paralysis.

18. The method of claim 1, wherein said sarcoidosis is cardiac sarcoidosis.

19. The method of claim 18, wherein said symptom is one or more of chest pain, palpitations, congestive heart failure, pericarditis or papillary muscle dysfunction, shortness of breath, ankle swelling, irregular heart beat or sudden death.

20. The method of claim 1, wherein said sarcoidosis is ocular sarcoidosis.

21. The method of claim 20, wherein said symptom is one or more of red or watery eyes, granulomatous uvetis, iris nodules, retinochoroiditis, conjunctivitis, lacrimal gland involvement or proptosis.

22. The method of claim 1, comprising administering a second therapeutic agent to said individual.

23. The method of claim 22, wherein said second therapeutic agent is an anti-inflammatory agent, a steroid, an immunosuppressant compound, or an antibiotic.

* * * * *